United States Patent
Gareau et al.

(10) Patent No.: US 6,242,493 B1
(45) Date of Patent: Jun. 5, 2001

(54) CARBOXYLIC ACIDS AND ACYLSULFONAMIDES, COMPOSITIONS CONTAINING SUCH COMPOUNDS AND METHODS OF TREATMENT

(75) Inventors: Yves Gareau; Marc LaBelle, both of Ile Perrot; Helene Juteau, Montreal; Michel Gallant, Montréal Quest; Nicolas LaChance; Michel Belley, both of Pierrefonds, all of (CA)

(73) Assignee: Merck Frosst Canada & Co., Kirkland (CA)

( * ) Notice: Subject to any disclaimer, the term of this patent is extended or adjusted under 35 U.S.C. 154(b) by 0 days.

(21) Appl. No.: 09/266,047

(22) Filed: Mar. 10, 1999

Related U.S. Application Data

(60) Provisional application No. 60/077,990, filed on Mar. 13, 1998.

(51) Int. Cl.[7] .......................... C07C 311/51; A61K 31/18
(52) U.S. Cl. ...................... 514/569; 514/604; 549/65; 562/400; 562/466; 562/490; 564/91
(58) Field of Search ..................... 562/460, 466, 562/490; 549/65; 564/91; 514/604, 569

(56) References Cited

U.S. PATENT DOCUMENTS

| | | | |
|---|---|---|---|
| 4,906,662 | * | 3/1990 | Hashimoto ........................ 514/524 |
| 4,996,214 | | 2/1991 | Cousins et al. |

FOREIGN PATENT DOCUMENTS

| | | |
|---|---|---|
| 0 028 063 | 5/1981 | (EP) . |
| 0 157 420 A2 | 10/1985 | (EP) . |
| 0 223 593 A2 | 5/1987 | (EP) . |
| 0 459 243 A2 | 12/1991 | (EP) . |
| 0 536 713 A1 | 4/1993 | (EP) . |
| 0 560 080 A1 | 9/1993 | (EP) . |
| 0 566 835 A1 | 10/1993 | (EP) . |
| 0 752 421 A1 | 1/1997 | (EP) . |
| WO 92/02495 | 2/1992 | (WO) . |
| WO 95/13262 | 5/1995 | (WO) . |
| WO 96/06822 | 3/1996 | (WO) . |
| WO 96/11902 | 4/1996 | (WO) . |
| WO 96/31505 | 10/1996 | (WO) . |
| WO 97/08934 | 3/1997 | (WO) . |
| WO 97/10246 | 3/1997 | (WO) . |
| WO 97/25328 | 7/1997 | (WO) . |

OTHER PUBLICATIONS

Chemical Abstracts, Columbus, Ohio, US vol. 109 (1988) 21–11 No. 21, pp. 691 (Katherine Buggle, et als.).
Chemical Abstracts, Columbus, Ohio, US vol. 107 (1987) 23–11, No. 21, pp. 43 (Yukihiro Goda, et als).
Chemical Abstracts, Columbus, Ohio, US vol. 117 (1992) 03–08 No. 5, pp. 20 (Chenfang Tseng, et als.).
Chemical Abstracts, Columbus, Ohio, US vol. 91 (1979) 17–12 No. 25, pp. 644 (Joseph E. Plevyak, et als.).
Chemical Abstracts, Columbus, Ohio, US vol. 95, (1981) 09–11 No. 19, pp.25 (Kinji, Iizuka, et als.).
Chemical Abstracts, Columbus, Ohio, US vol. 119 (1993) 09–08 No. 6, pp. 423 (Tomohiro Yokota, et als.).
Chemical Abstracts, Columbus, Ohio, US, vol. 99 (1983) 10–10 No. 15, pp. 21 (David Atkinson, et als.).
Ram, Indian J Chem Sect B 23B(12) 1261–7 CA 102:220700t, 1984.*

\* cited by examiner

*Primary Examiner*—Robert Gerstl
(74) *Attorney, Agent, or Firm*—Raynard Yuro; Richard C. Billups; David L. Rose

(57) ABSTRACT

Compounds of formula I:

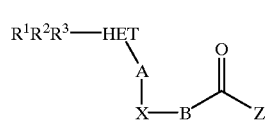

as well as pharmaceutically acceptable salts, hydrates and esters thereof, are disclosed.

The compounds are useful for treating or preventing prostaglandin mediated diseases. Pharmaceutical compositions containing such compounds and methods of treatment are also included.

16 Claims, No Drawings

US 6,242,493 B1

CARBOXYLIC ACIDS AND ACYLSULFONAMIDES, COMPOSITIONS CONTAINING SUCH COMPOUNDS AND METHODS OF TREATMENT

CROSS REFERENCE TO RELATED APPLICATIONS

This application is a non-provisional application related to U.S. application Ser. No. 60/077,990, filed on Mar. 13, 1998 priority of which is claimed hereunder.

BACKGROUND OF THE INVENTION

The present invention relates to compounds which are useful for treating or preventing prostaglandin mediated diseases, methods of treatment and pharmaceutical compositions containing such compounds. The compounds are structurally different from conventional NSAIDs and opiates, and are antagonists of the pain and inflammatory effects of E-type prostaglandins.

Two review articles describe the characterization and therapeutic relevance of the prostanoid receptors as well as the most commonly used selective agonists and antagonists: *Eicosanoids: From Biotechnology to Therapeutic Applications*, Folco, Samuelsson, Maclouf, and Velo eds, Plenum Press, New York, 1996, chap. 14, 137–154 and Journal of Lipid Mediators and Cell Signalling, 1996, 14, 83–87. An article from *The British Journal of Pharmacology* (1994, 112, 735–740) suggests that Prostaglandin $E_2$ ($PGE_2$) exerts allodynia through the $EP_1$ receptor subtype and hyperalgesia through $EP_2$ and $EP_3$ receptors in the mouse spinal cord.

Thus, selective prostaglandin ligands, agonists or antagonists, depending on which prostaglandin E receptor subtype is being considered, have anti-inflammatory, anti-pyretic and analgesic properties, and in addition inhibit hormone-induced uterine contractions. Moreover, the compounds have anti-cancer effects.

The compounds have a reduced potential for gastrointestinal toxicity, a reduced potential for renal side effects, a reduced effect on bleeding times and a lessened ability to induce asthma attacks in aspirin-sensitive asthmatic subjects.

SUMMARY OF THE INVENTION

The present invention relates to compounds represented by formula I:

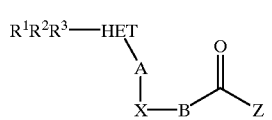

I as well as pharmaceutically acceptable salts, hydrates and esters thereof, wherein:

HET represents a 5–12 membered monocyclic or bicyclic aromatic ring system containing 0–3 heteroatoms selected from O, $S(O)_n$ and $N(O)_m$ wherein m is 0 or 1 and n is 0, 1 or 2;

A is a one or two atom moiety and is selected from the group consisting of: —W—, —C(O)—, —C($R^7$)$_2$—W—, —W—C($R^7$)$_2$—, —C$R^7$(O$R^{20}$)—, —C($R^7$)$_2$—, —C($R^7$)$_2$—C(O$R^{20}$)$R^7$—, —C($R^7$)$_2$—C($R^7$)$_2$— or —C$R^7$=C$R^7$—, wherein W represents O, $S(O)_n$ or $NR^{17}$, with n as previously defined and $R^{17}$ as defined below;

X represents a 5–10 membered monocyclic or bicyclic aryl or heteroaryl group having 1–3 heteroatoms selected from O, $S(O)_n$ and $N(O)_m$, and optionally substituted with $R^{14}$ and $R^{15}$, and A and B are attached to the aryl or heteroaryl group ortho relative to each other;

Y represents O, $S(O)_n$, $NR^{17}$, a bond or —$CR^{18}$=$CR^{18}$—;

B represents —(C($R^{18}$)$_2$)$_p$—Y—(C($R^{18}$)$_2$)$_q$— wherein p and q are independently 0–3, such that when Y represents O, $S(O)_n$, $NR^{17}$ or —$CR^{18}$=$CR^{18}$—, p+q=0–6, and when Y represents a bond, p+q is 1–6;

Z is OH or $NHS_2R^{19}$;

$R^1$ $R^2$ and $R^3$ independently represent H, halogen, lower alkyl, lower alkenyl, lower alkynyl, lower alkenyl-HET ($R^a$)$_{4-9}$, —(C($R^4$)$_2$)$_p$$SR^5$, —(C($R^4$)$_2$)$_p$$OR^8$, —(C($R^4$)$_2$)$_p$N($R^6$)$_2$, CN, $NO_2$, —(C($R^4$)$_2$)$_p$C($R^7$)$_3$, —$CO_2R^9$, —CON($R^6$)$_2$ or —(C($R^4$)$_2$)$_p$S(O)$_n$$R^{10}$, wherein n and p are as previously defined;

each $R^4$ is independently H, F, $CF_3$ or lower alkyl, or two $R^4$ groups are taken in conjunction and represent a ring of up to six atoms, optionally containing one heteroatom selected from O, $S(O)_n$ or $N(O)_m$;

each $R^5$ is independently lower alkyl, lower alkenyl, lower alkynyl, $CF_3$, lower alkyl-HET, lower alkenyl-HET or —(C($R^{18}$)$_2$)$_p$Ph($R^{11}$)$_{0-2}$;

each $R^6$ is independently H, lower alkyl, lower alkenyl, lower alkynyl, $CF_3$, Ph, Bn and when two $R^6$ groups are attached to N they may be taken in conjunction and represents a ring of up to 6 atoms, optionally containing an additional heteroatom selected from O, $S(O)_n$ or $N(O)_m$;

each $R^7$ is independently H, F, $CF_3$ or lower alkyl, and when two $R^7$ groups are presents, they may be taken in conjunction and represent an aromatic or aliphatic ring of 3 to 6 members containing from 0–2 heteroatoms selected from O, $S(O)_n$ and $N(O)_m$;

each $R^8$ represents H or $R^5$;

each $R^9$ is independently H, lower alkyl, lower alkenyl, lower alkynyl, Ph or Bn;

each $R^{10}$ is independently lower alkyl, lower alkenyl, lower alkynyl, $CF_3$, Ph($R^{11}$)$_{0-3}$, $CH_2$Ph($R^{11}$)$_{0-3}$ or $N(R^6)_2$;

each $R^{11}$ is independently lower alkyl, $SR^{20}$, $OR^{20}$, $N(R^6)_2$, —$CO_2R^{12}$, —CON($R^6$)$_2$, —C(O)$R^{12}$, CN, $CF_3$, $NO_2$ or halogen;

each $R^{12}$ is independently H, lower alkyl or benzyl;

each $R^{13}$ is independently H, halo, lower alkyl, O-lower alkenyl, S-lower alkyl, N($R^6$)$_2$, $CO_2R^{12}$, CN, $CF_3$ or $NO_2$;

$R^{14}$ and $R^{15}$ are independently lower alkyl, halogen, $CF_3$, $OR^{16}$, $S(O)_nR^{16}$ or $C(R^{16})_2OR^{17}$;

each $R^{16}$ is independently H, lower alkyl, lower alkenyl, Ph, Bn or $CF_3$;

each $R^{17}$ is independently H, lower alkyl or Bn;

each $R^{18}$ is independently H, F or lower alkyl, and when two $R^{18}$ groups are present, they may be taken in conjunction and represent a ring of 3 to 6 members comprising carbon atoms and optionally one heteroatom chosen from O, $S(O)_n$ or N;

each $R^{19}$ is lower alkyl, lower alkenyl, lower alkynyl, $CF_3$, HET($R^a$)$_{4-9}$, lower alkyl-HET($R^a$)$_{4-9}$ or lower alkenyl-HET($R^a$)$_{4-9}$;

each $R^{20}$ is independently H, lower alkyl, lower alkenyl, lower alkynyl, $CF_3$ or Ph($R^{13}$)$_2$ and each $R^a$ is independently selected from the group consisting of: H, OH, halo, CN, $NO_2$, amino, $C_{1-6}$alkyl, $C_{2-6}$alkenyl, $C_{2-6}$alkynyl, $C_{1-6}$ alkoxy, $C_{2-6}$alkenyloxy, $C_{2-6}$alkynyloxy, $C_{1-6}$alkylamino, di-$C_{1-6}$alkylamino, $CF_3$, $C(O)C_{1-6}$alkyl, $C(O)C_{2-6}$alkenyl, $C(O)C_{2-6}$alkynyl, $CO_2H$, $CO_2C_{1-6}$alkyl, $CO_2C_{2-6}$alkenyl, and $CO_2C_{2-6}$alkynyl, said alkyl, alkenyl, alkynyl and the alkyl portions of alkylamino and dialkylamino being optionally substituted with 1–3 of: hydroxy, halo, aryl, $C_{1-6}$ alkoxy, $C_{2-6}$alkenyloxy, $C_{2-6}$alkynyloxy, $CF_3$, $C(O)C_{1-6}$alkyl, $C(O)C_{2-6}$alkenyl, $C(O)C_{2-6}$alkynyl, $CO_2H$, $CO_2C_{1-6}$alkyl, $CO_2C_{2-6}$alkenyl, $CO_2C_{2-6}$alkynyl, $NH_2$, $NHC_{1-6}$alkyl and $N(C_{1-6}alkyl)_2$.

Pharmaceutical compositions are also included which are comprised of a compound of formula I in combination with a pharmaceutically acceptable carrier A method of treating or preventing a prostaglandin mediated disease is also included which is comprised of administering to a mammalian patient in need thereof, a compound of formula I in an amount which is effective for treating or preventing a prostaglandin mediated disease.

DETAILED DESCRIPTION OF THE INVENTION

The present invention relates to carboxylic acids and acylsulfonamides, which are ligands at prostaglandin receptors, as well as a method for treating or preventing a prostaglandin mediated disease comprising administering to a patient in need of such a treatment of an amount of compound of Formula I which is effective for treating or preventing a prostaglandin mediated disease.

The invention described in this patent application is described using the following definitions unless otherwise indicated.

HET represents a 5–12 membered aromatic ring system containing 0–3 heteroatoms selected from O, $S(O)_n$ and N wherein n is 0, 1 or 2. HET may be substituted with up to three substituents on the aromatic ring system, $R^1$, $R^2$ and $R^3$. "Aromatic ring systems" as used herein includes aryl and heteroaryl groups such as benzene, naphthalene, biphenyl, pyridine, quinoline, isoquinoline, furan, benzofuran, thiophene, benzothiophene, oxazole, thiazole, imidazole, benzothiazole, triazole, 1,2,5-thiadiazole, thienopyridine, indole, tetrazole, imidazole, benzoxazole, 1,2-methylenedioxybenzene and pyrrole.

$HET^2$ is a subset of HET and represents a member selected from the group consisting of: phenyl, thienyl, naphthyl, furanyl, thiazolyl, imidazolyl and indolyl.

Aryl refers to aromatic 6–10 membered groups having 1–2 rings and alternating (resonating) double bonds. Examples include phenyl, biphenyl and naphthyl.

Heteroaryl refers to aromatic 5–12 membered groups having alternating (resonating) double bonds and containing from 1–4 heteroatoms selected from O, $S(O)_n$ and N. Examples include the following:: quinoline, furan, benzofuran, thiophene, benzothiophene, thiazole, benzothiazole, 1,2,5-thiadiazole, thienopyridine, oxazole, indole, isoindole, pyridine, isoquinoline, imidazole, thiazole, triazole, 1,3-methylene dioxobenzene, pyrrole and naphthyridine, Heterocyclyl refers to non-aromatic 5–12 membered cyclic groups having 1–4 heteroatoms selected from O, $S(O)_n$ and N. Examples of heterocyclic groups are piperidine, piperazine, pyrrolidine, tetrahydrofuran, tetrahydropyran and morpholine.

X represents a 5–10 membered monocyclic or bicyclic aryl or heteroaryl group having 1–3 heteroatoms selected from O, $S(O)_n$ and $N(O)_m$, and optionally substituted with $R^{14}$ and $R^{15}$, and A and B are attached to the aryl or heteroaryl group X in positions which are ortho relative to each other. Examples are selected from the group consisting of: phenyl, naphthyl, biphenyl, quinoline, furan, benzofuran, pyridyl, pyrrole, thiophene, benzothiophene, thiazole, benzothiazole, 1,2,5-thiadiazole, triazole, 1,2-methylenedioxybenzene, thienopyridine, oxazole and indole.

The terms alkyl, alkenyl, and alkynyl mean linear, branched, and cyclic structures and combinations thereof.

"Lower alkyl" means alkyl groups of from 1 to 7 carbon atoms. Examples of lower alkyl groups include methyl, ethyl, propyl, cyclopropyl, isopropyl, butyl, s- and t-butyl, pentyl, cyclopentyl, hexyl, cyclohexyl, heptyl, and the like. When propyl and butyl are recited without the isomeric form being specified, these include all isomers thereof.

"Lower alkenyl" means alkenyl groups of 2 to 7 carbon atoms. Examples of lower alkenyl groups include vinyl, allyl, isopropenyl, pentenyl, hexenyl, heptenyl, 1-propenyl, 2-butenyl, 2-methyl-2-butenyl, cyclopropen-1-yl, cyclohexen-3-yl and the like. When cis or trans is not specified, both are intended in pure form as well as in the form of a mixture of isomers.

"Lower alkynyl" means alkynyl groups of 2 to 7 carbon atoms. Examples of lower alkynyl groups include ethynyl, propargyl, 3-methyl-1-pentynyl, 2-heptynyl, 2-(cyclopropyl)ethenyl, 3-(cyclobutyl)-1-propynyl and the like.

Halogen (halo) includes F, Cl, Br and I.

The following abbreviations have the indicated meanings:

AIBN=2.2'-azobisisobutyronitrile
B.P.=benzoyl peroxide
Bn=benzyl
$CCl_4$=carbon tetrachloride
D=—O(CH$_2$)$_3$O—
DAST=diethylamine sulfur trifluoride
DCC=dicyclohexyl carbodiimide
DCI=1-(3-dimethylaminopropyl)-3-ethyl carbodiimide
DEAD=diethyl azodicarboxylate
DIBAL=diisobutyl aluminum hydride
DME=ethylene glycol dimethylether
DMAP=4-(dimethylamino)pyridine
DMF=N,N-dimethylformamide
DMSO=dimethyl sulfoxide
$Et_3N$=triethylamine
LDA=lithium diisopropylamide
m-CPBA=metachloroperbenzoic acid
NBS=N-bromosuccinimide
NSAID=non-steroidal anti-inflammatory drug
PCC=pyridinium chlorochromate
PDC=pyridinium dichromate
Ph=phenyl
1,2-Ph=1,2-benzenediyl
Pyr=pyridinediyl
Qn=7-chloroquinolin-2-yl
$R^s$=—$CH_2SCH_2CH_2Ph$
r.t.=room temperature
rac.=racemic THF=tetrahydrofuran
THP=tetrahydropyran-2-yl
Alkyl Group Abbreviations
Me=methyl
Et=ethyl
n-Pr=normal propyl
i-Pr=isopropyl
n-Bu=normal butyl
i-Bu=isobutyl
s-Bu=secondary butyl
t-Bu=tertiary butyl
c-Pr=cyclopropyl
c-Bu=cyclobutyl
c-Pen=cyclopentyl
c-Hex=cyclohexyl It is intended that the definition of any substituent (e.g., $R^5$, $R^6$, etc.) in a particular molecule be independent of its definition elsewhere in the molecule. Thus, —N($R^6$)$_2$ represents —NHH, —NHCH$_3$, —NHC$_6$H$_5$, and the like.

In one aspect of the invention, the invention relates to a compound represented by formula I:

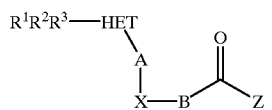

as well as pharmaceutically acceptable salts, hydrates and esters thereof, wherein:

HET represents a 5–12 membered monocyclic or bicyclic aromatic ring system containing 0–3 heteroatoms selected from O, S(O)$_n$ and N(O)$_m$ wherein m is 0 or 1 and n is 0, 1 or 2;

A is a one or two atom moiety and is selected from the group consisting of: —W—, —C(O)—, —C($R^7$)$_2$—W—, —W—C($R^7$)$_2$—, —C$R^7$(O$R^{20}$)—, —C($R^7$)$_2$—, —C($R^7$)$_2$—C(O$R^{20}$)$R^7$—, —C($R^7$)$_2$—C($R^7$)$_2$ or C$R^7$=C$R^7$, wherein W represents O, S(O)$_n$ or N$R^{17}$, with n as previously defined and $R^{17}$ as defined below;

X represents a 5–10 membered monocyclic or bicyclic aryl or heteroaryl group having 1–3 heteroatoms selected from O, S(O)$_n$ and N(O)$_m$, and optionally substituted with $R^{14}$ and $R^{15}$, and A and B are attached to the aryl or heteroaryl group ortho relative to each other;

Y represents O, S(O)$_n$, N$R^{17}$ a bond or —C$R^{18}$=C$R^{18}$—;

B represents —(C($R^{18}$)$_2$)$_p$—Y—(C($R^{18}$)$_2$)$_q$— wherein p and q are independently 0—3, such that when Y represents O, S(O)$_n$, N$R^{17}$ or —C$R^{18}$=C$R^{18}$—, p+q=0–6, and when Y represents a bond, p+q is 1–6;

Z is OH or NHSO$_2$$R^{19}$;

$R^1$ $R^2$ and $R^3$ independently represent H, halogen, lower alkyl, lower alkenyl, lower alkynyl, lower alkenyl-HET($R^a$)$_{4-9}$, —(C($R^4$)$_2$)$_p$S$R^5$, —(C($R^4$)$_2$)$_p$O$R^8$, —(C($R^4$)$_2$)$_p$N($R^6$)$_2$, CN, NO$_2$, —(C($R^4$)$_2$, —(C($R^4$)$_2$)$_p$C($R^7$)$_3$, —CO$_2$$R^9$, —CON($R^6$)$_2$ or —(C($R^4$)$_2$)$_p$S(O)$_n$$R^{10}$, wherein n and p are as previously defined;

each $R^4$ is independently H, F, CF$_3$ or lower alkyl, or two $R^4$ groups are taken in conjunction and represent a ring of up to six atoms, optionally containing one heteroatom selected from O, S(O)$_n$ or N(O)$_m$;

each $R^5$ is independently lower alkyl, lower alkenyl, lower alkynyl, CF$_3$, lower alkyl-HET, lower alkenyl-HET or —(C($R^{18}$)$_2$)$_p$Ph($R^{11}$)$_{0-2}$;

each $R^6$ is independently H, lower alkyl, lower alkenyl, lower alkynyl, CF$_3$, Ph, Bn and when two $R^6$ groups are attached to N they may be taken in conjunction and represents a ring of up to 6 atoms, optionally containing an additional heteroatom selected from O, S(O)$_n$ or N(O)$_m$;

each $R^7$ is independently H, F, CF$_3$ or lower alkyl, and when two $R^7$ groups are presents, they may be taken in conjunction and represent an aromatic or aliphatic ring of 3 to 6 members containing from 0–2 heteroatoms selected from O, S(O)$_n$ and N(O)$_m$;

each $R^8$ represents H or $R^5$;

each $R^9$ is independently H, lower alkyl, lower alkenyl, lower alkynyl, Ph or Bn;

each $R^{10}$ is independently lower alkyl, lower alkenyl, lower alkynyl, CF$_3$, Ph($R^{11}$)$_{0-3}$, CH$_2$Ph($R^{11}$)$_{0-3}$ or N($R^6$)$_2$;

each $R^{11}$ is independently lower alkyl, S$R^{20}$, O$R^{20}$, N($R^6$)$_2$, —CO$_2$$R^{12}$, —CON($R^6$)$_2$, —C(O)$R^{12}$, CN, CF$_3$, NO$_2$ or halogen;

each $R^{12}$ is independently H, lower alkyl or benzyl;

each $R^{11}$ is independently H, halo, lower alkyl, O-lower alkenyl, S-lower alkyl, N($R^6$)$_2$, CO$_2$$R^{12}$, CN, CF, or NO$_2$;

$R^{14}$ and $R^{15}$ are independently lower alkyl, halogen, CF$_3$, O$R^{16}$, S(O)$_n$$R^{16}$ or O($R^{16}$)$_2$O$R^{17}$;

each $R^{16}$ is independently H, lower alkyl, lower alkenyl, Ph, Bn or CF$_3$;

each $R^{17}$ is independently H, lower alkyl or Bn;

each $R^{18}$ is independently H, F or lower alkyl, and when two $R^{18}$ groups are present, they may be taken in conjunction and represent a ring of 3 to 6 members comprising carbon atoms and optionally one heteroatom chosen from O, S(O)$_n$ or N;

each $R^{19}$ is lower alkyl, lower alkenyl, lower alkynyl, CF$_3$, HET($R^a$)$_{4-9}$, lower alkyl-HET($R^a$)$_{4-9}$ or lower alkenyl-HET($R^a$)$_{4-9}$;

each $R^{20}$ is independently H, lower alkyl, lower alkenyl, lower alkynyl, CF$_3$ or Ph($R^{13}$)$_2$ and each $R^a$ is independently selected from the group consisting of: H, OH, halo, CN, NO$_2$, amino, C$_{1-6}$alkyl, C$_{2-6}$alkenyl, C$_{2-6}$alkynyl, C$_{1-6}$ alkoxy, C$_{2-6}$alkenyloxy, C$_{2-6}$alkynyloxy, C$_{1-6}$alkylamino, di-C$_{1-6}$alkylamino, CF$_3$, C(O)C$_{1-6}$alkyl, C(O)C$_{2-6}$alkenyl, C(O)C$_{2-6}$alkynyl, CO$_2$H, CO$_2$C$_{1-6}$alkyl, CO$_2$C$_{2-6}$alkenyl, and CO$_2$C$_{2-6}$alkynyl, said alkyl, alkenyl, alkynyl and the alkyl portions of alkylamino and dialkylamino being optionally substituted with 1–3 of: hydroxy, halo, aryl, C$_{1-6}$ alkoxy, C$_{2-6}$alkenyloxy, C$_{2-6}$alkynyloxy, CF$_3$, C(O)C$_{1-6}$alkyl, C(O)C$_{2-6}$alkenyl, C(O)C$_{2-6}$alkynyl, CO$_2$H, CO$_2$C$_{1-6}$ alkyl, CO$_2$C$_{2-6}$alkenyl, CO$_2$C$_{2-6}$alkynyl, NH$_2$, NHC$_{1-6}$ alkyl and N(C$_{1-6}$alkyl)$_2$.

In another embodiment of the invention, the invention relates to compounds represented by formula I:

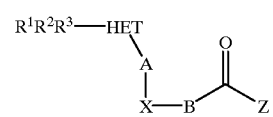

as well as pharmaceutically acceptable salts, hydrates and esters thereof, wherein:

HET represents a 5–12 membered monocyclic or bicyclic aromatic ring system containing 0–3 heteroatoms selected from O, $S(O)_n$ and $N(O)_m$ wherein m is 0 or 1 and n is 0, 1 or 2;

A is a one or two atom moiety and is selected from the group consisting of: —W—, —C(O)—, —C($R^7$)$_2$—W—, —W—C($R^7$)$_2$—, —C$R^7$(O$R^{20}$)—, —C($R^7$)$_2$—, —C($R^7$)$_2$—C(O$R^{20}$)$R^7$—, —C($R^7$)$_2$—C($R^7$)$_2$— or C$R^7$=C$R^7$, wherein W represents O, $S(O)_n$ or $NR^{17}$, with n as previously defined and $R^{17}$ as defined below;

X represents a 5–10 membered monocyclic or bicyclic aryl or heteroaryl group having 1–3 heteroatoms selected from O, $S(O)_n$ and $N(O)_m$, and optionally substituted with $R^{14}$ and $R^{15}$, and A and B are attached to the aryl or heteroaryl group ortho relative to each other;

Y represents O, $S(O)_n$, $NR^{17}$, a bond or —$CR^{18}$=$CR^{18}$—;

B represents —(C($R^{18}$)$_2$)$_p$—Y—(C($R^{18}$)$_2$)$_q$— wherein p and q are independently 0–3, such that when Y represents O, $S(O)_n$, $NR^{17}$ or —$CR^{18}$=$CR^{18}$—, p+q=0–6, and when Y represents a bond, p+q is 1–6;

Z is OH or $NHSO_2R^{19}$;

$R^1$ $R^2$ and $R^3$ independently represent H, halogen, lower alkyl, lower alkenyl, lower alkynyl, lower alkenyl-HET($R^a$)$_{4-9}$, —(C($R^4$)$_2$)$_p$S$R^5$, —(C($R^4$)$_2$)$_p$O$R^8$, —(C($R^4$)$_2$)$_p$N($R^6$)$_2$, CN, $NO_2$, —(C($R^4$)$_2$)$_p$C($R^7$)$_3$, —$CO_2R^9$, —CON($R^6$)$_2$ or —(C($R^4$)$_2$)$_p$S(O)$_n R^{10}$, wherein n and p are as previously defined;

each $R^4$ is independently H, F, CF, or lower alkyl, or two $R^4$ groups are taken in conjunction and represent a ring of up to six atoms, optionally containing one heteroatom selected from O, $S(O)_n$ or $N(O)_m$;

each $R^5$ is independently lower alkyl, lower alkenyl, lower alkynyl, $CF_3$, lower alkyl-HET, lower alkenyl-HET or —(C($R^{18}$)$_2$)$_p$Ph($R^{11}$)$_{0-2}$;

each $R^6$ is independently H, lower alkyl, lower alkenyl, lower alkynyl, $CF_3$, Ph, Bn and when two $R^6$ groups are attached to N they may be taken in conjunction and represents a ring of up to 6 atoms, optionally containing an additional heteroatom selected from O, $S(O)_n$ or $N(O)_m$;

each $R^7$ is independently H, F, $CF_3$ or lower alkyl, and when two $R^7$ groups are presents, they may be taken in conjunction and represent an aromatic or aliphatic ring of 3 to 6 members containing from 0–2 heteroatoms selected from O, $S(O)_n$ and $N(O)_m$;

each $R^8$ represents H or $R^5$;

each $R^9$ is independently H, lower alkyl, lower alkenyl, lower alkynyl, Ph or Bn;

each $R^{10}$ is independently lower alkyl, lower alkenyl, lower alkynyl, $CF_3$, Ph($R^{11}$)$_{0-3}$, $CH_2$Ph($R^{11}$)$_{0-3}$ or N($R^6$)$_2$;

each $R^{11}$ is independently lower alkyl, $SR^{20}$, $OR^{20}$, N($R^6$)$_2$, —$CO_2R^{12}$, —CON($R^6$)$_2$, —C(O)$R^{12}$, CN, $CF_3$, $NO_2$ or halogen;

each $R^{12}$ is independently H, lower alkyl or benzyl;

each $R^{13}$ is independently H, halo, lower alkyl, O-lower alkenyl, S-lower alkyl, N($R^6$)$_2$, $CO_2R^{12}$, CN, $CF_3$ or $NO_2$;

$R^{14}$ and $R^{15}$ are independently lower alkyl, halogen, $CF_3$, $OR^{16}$, $S(O)_n R^{16}$ or $C(R^{16})_2 OR^{17}$;

each $R^{16}$ is independently H, lower alkyl, lower alkenyl, Ph, Bn, $CHF_2$ or $CF_3$;

each $R^{17}$ is independently H, lower alkyl or Bn;

each $R^{18}$ is independently H, F or lower alkyl, and when two $R^{18}$ groups are present, they may be taken in conjunction and represent a ring of 3 to 6 members comprising carbon atoms and optionally one heteroatom chosen from O, $S(O)_n$ or N;

each $R^{19}$ is lower alkyl, lower alkenyl, lower alkynyl, $CF_3$, $HET^2(R^a)_{4-9}$, lower alkyl-$HET^2(R^a)_{4-9}$ or lower alkenyl-$HET^2(R^a)_{4-9}$, wherein $HET^2$ represents a member selected from the group consisting of: phenyl, thienyl, naphthyl, furanyl, thiazolyl, imidazolyl and indolyl;

each $R^{20}$ is independently H, lower alkyl, lower alkenyl, lower alkynyl, $CHF_2$, $CF_3$ or Ph($R^{13}$)$_2$ and each $R^a$ is independently selected from the group consisting of: H, OH, halo, CN, $NO_2$, amino, $C_{1-6}$alkyl, $C_{2-6}$alkenyl, $C_{2-6}$alkynyl, $C_{1-6}$ alkoxy, $C_{2-6}$alkenyloxy, $C_{2-6}$alkynyloxy, $C_{1-6}$alkylamino, di-$C_{1-6}$alkylamino, $CF_3$, C(O)$C_{1-6}$alkyl, C(O)$C_{2-6}$alkenyl, C(O)$C_{2-6}$alkynyl, $CO_2$H, $CO_2C_{1-6}$alkyl, $CO_2C_{2-6}$alkenyl, and $CO_2C_{2-6}$alkynyl, said alkyl, alkenyl, alkynyl and the alkyl portions of alkylamino and dialkylamino being optionally substituted with 1—3 of: hydroxy, halo, aryl, $C_{1-6}$ alkoxy, $C_{2-6}$alkenyloxy, $C_{2-6}$alkynyloxy, $CF_3$, C(O)$C_{1-6}$alkyl, C(O)$C_{2-6}$alkenyl, C(O)$C_{2-6}$alkynyl, $CO_2$H, $CO_2C_{1-6}$ alkyl, $CO_2C_{2-6}$alkenyl, $CO_2C_{2-6}$alkynyl, $NH_2$, $NHC_{1-6}$ alkyl and N($C_{1-6}$alkyl)$_2$.

An embodiment of the present invention which is of particular interest is represented by formula I wherein HET represents a member selected from the group consisting of: benzene, naphthalene, biphenyl, pyridine, quinoline, isoquinoline, furan, benzofuran, thiophene, benzothiophene, oxazole, thiazole, imidazole, benzothiazole, triazole, 1,2,5-thiadiazole, thienopyridine, indole, tetrazole, imidazole, benzoxazole, 1,2-methylenedioxybenzene and pyrrole.

More particularly, an embodiment of the present invention is represented by formula I wherein HET is selected from the group consisting of: benzene, biphenyl, naphthylene, indole, thiophene, benzofuran and quinoline. Within this subset of compounds of the invention, all other variables are as originally described with respect to formula I.

Another embodiment of the present invention that is of particular interest is represented by formula I wherein A represents a one or two atom moiety and is selected from the group consisting of: S, S(O), $SO_2$, $CH_2$, —C(O)—, —$OCH_2$—, —CHOH—, —C(OH)($CH_3$)— and —$CH_2$—O—. More particularly, A is selected from the group consisting of:: S, S(O), $SO_2$, $CH_2$, —C(O)—. Within this subset of compounds of the invention, all other variables are as originally described with respect to formula I.

Another embodiment of the present invention that is of particular interest is represented by formula I wherein X represents phenyl optionally substituted with $R^{14}$ and $R^{15}$. Within this subset of compounds of the invention, all other variables are as originally described with respect to formula I. More particularly, X represents phenyl and $R^{14}$ and $R^{15}$ are absent or represent halo. Within this subset of compounds of the invention, all other variables are as originally described with respect to formula I.

Another embodiment of the present invention that is of particular interest is represented by formula I wherein B is CH=CH or 1,2-cyclopropyl, and in particular, where B is CH=CH in the E-isomeric form. Within this subset of compounds of the invention, all other variables are as originally described with respect to formula I.

Another embodiment of the present invention that is of particular interest is represented by formula I wherein Z is $NHSO_2R^{19}$. Within this subset of compounds of the invention, all other variables are as originally described with respect to formula I.

Another embodiment of the present invention that is of particular interest is represented by formula I wherein Z is $NHSO_2R^{19}$ and $R^{19}$ represents a member selected from the group consisting of: lower alkyl and $HET(R^a)_3$. Within this aspect of the invention, HET is selected from the group consisting of: phenyl, thienyl, naphthyl, furanyl, thiazolyl, imidazolyl and indolyl.

Another embodiment of the present invention that is of particular interest is represented by formula I wherein Z is $NHSO_2R^{19}$ and $R^{19}$ represents benzene or thiophene, substituted with $R^1R^2R^3$.

Another embodiment of the present invention that is of particular interest is represented by formula I wherein Z represents OH. Within this subset, all other variables are as originally defined.

A subset of compounds that is of particular interest is defined with respect to formula I wherein:

HET represents a member selected from the group consisting of: phenyl, naphthalene, biphenyl, pyridine, quinoline, isoquinoline, furan, benzofuran, thiophene, benzothiophene, oxazole, thiazole, imidazole, benzothiazole, 1,2,5-thiadiazole, thienopyridine, indole, tetrazole, imidazole, benzoxazole and pyrrole;

A represents a one or two atom moiety and is selected from the group consisting of: S, S(O), $SO_2$, $CH_2$, —C(O)—, —$OCH_2$—, —CHOH—, —C(OH)(CH_3)— and —$CH_2$—O—;

X represents phenyl optionally substituted with $R^{14}$ and $R^{15}$;

B is CH=CH;

Z is $NHSO_2R^{19}$ and $R^{19}$ represents a member selected from the group consisting of: lower alkyl and $HET(R^a)_3$.

Examples of compounds of the present invention are shown in Tables I and II below.

TABLE I

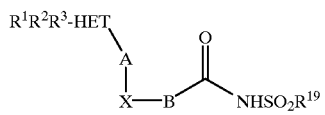

Ia (Compounds 1–323 and 347–454)

| $R^1R^2R^3$-Het | A | X | B | $R^{19}$ | Cpd |
|---|---|---|---|---|---|
| 1-naphthyl | $CH_2$ | 1,2-Ph | CH=CH | $Ph(F)_5$ | 1 |
| 2-naphthyl | $S(O)_2$ | 1,2-Ph | CH=CH | $Ph(F)_5$ | 2 |
| 3-methylindol-1-yl | $CH_2$ | 1,2-Ph | CH=CH | 2-thienyl | 3 |
| 2-naphthyl | $CH_2$ | 1,2-Ph | CH=CH | 2-thienyl | 4 |
| 2-naphthyl | $S(O)_2$ | 1,2-Ph | CH=CH | phenyl | 5 |
| 3-methylindol-1-yl | $S(O)_2$ | 1,2-Ph | CH=CH | 2-thienyl | 6 |
| 2-naphthyl | $S(O)_2$ | 1,2-Ph | CH=CH | 3,5-di-($CF_3$) phenyl | 7 |
| 3,4-dichloro phenyl | $CH_2$ | 1,2-Ph | CH=CH | 2-thienyl | 8 |
| 2-naphthyl | $S(O)_2$ | 1,2-Ph | CH=CH | 2-thienyl | 9 |
| 2,4-dichloro phenyl | $CH_2$ | 1,2-Ph | CH=CH | 2-thienyl | 10 |
| 1-naphthyl | $S(O)_2$ | 1,2-Ph | CH=CH | $Ph(F)_5$ | 11 |
| 1-naphthyl | $S(O)_2$ | 1,2-Ph | CH=CH | 3,5-di-($CF_3$) phenyl | 12 |
| 2-naphthyl | $S(O)_2$ | 1,2-Ph | 1,2-c-propyl | 2-thienyl | 13 |
| 3,4-chloro fluoro phenyl | $CH_2$ | 1,2-Ph | CH=CH | 2-thienyl | 14 |
| 1-naphthyl | $CH_2$ | 1,2-Ph | CH=CH | 2-thienyl | 15 |
| 3,4-dichloro phenyl | $S(O)_2$ | 1,2-Ph | CH=CH | 2-thienyl | 16 |
| 4-methylthio phenyl | $CH_2$ | 1,2-Ph | CH=CH | 2-thienyl | 17 |
| 4-chlorophenyl | $CH_2$ | 1,2-Ph | CH=CH | 2-thienyl | 18 |
| 2-naphthyl | S | 1,2-Ph | CH=CH | 2-thienyl | 19 |
| 2-naphthyl | O—$CH_2$ | 1,2-Ph | CH=CH | 2-thienyl | 20 |
| 2-naphthyl | S(O) | 1,2-Ph | CH=CH | 2-thienyl | 21 |
| 1-naphthyl | $S(O)_2$ | 1,2-Ph | CH=CH | phenyl | 22 |
| 2-benzofuranyl | $CH_2$ | 1,2-Ph | CH=CH | 2-thienyl | 23 |
| 3,5-dichloro phenyl | $CH_2$ | 1,2-Ph | CH=CH | 2-thienyl | 24 |
| 1-naphthyl | $S(O)_2$ | 1,2-Ph | CH=CH | 3,5-di-($CF_3$) phenyl | 25 |
| 1-naphthyl | $S(O)_2$ | 1,2-Ph | CH=CH | 2-thienyl | 26 |
| 3-(1,2-(methylene | $CH_2$ | 1,2-Ph | CH=CH | 2-thienyl | 27 |

TABLE I-continued $$\text{R}^1\text{R}^2\text{R}^3\text{-HET} \underset{\text{X—B}}{\overset{\text{A}}{\diagdown}} \overset{\text{O}}{\underset{}{\text{C}}} \text{NHSO}_2\text{R}^{19}$$

Ia (Compounds 1–323 and 347–454)

| $R^1R^2R^3$-Het | A | X | B | $R^{19}$ | Cpd |
|---|---|---|---|---|---|
| dioxy)benzene) | | | | | |
| 2-naphthyl | O | 1,2-Ph | CH=CH | 2-thienyl | 28 |
| $R^s$-2-phenyl | $CH_2$ | 1,2-Ph | $CH_2$—O | 2-thienyl | 29 |
| $R^s$-2-phenyl | $CH_2$ | 1,2-Ph | $CH_2$—$CH_2$ | 2-thienyl | 30 |
| 2-naphthyl | $S(O)_2$ | 1,2-Ph | $CH_2$—O | 2-thienyl | 31 |
| 3-((2-(Qn)vinyl))phenyl | $CH_2$ | 1,2-Ph | $CH_2$—O | 2-thienyl | 32 |
| 2-(6-benzyloxy)naphthyl | $CH_2$ | 1,2-Ph | CH=CH | 2-thienyl | 33 |
| 3-((2-(Qn)vinyl))phenyl | SO | 1,2-Ph | $CH_2$—O | 2-thienyl | 34 |
| 3-((2-(Qn)vinyl))phenyl | —CHOH— | 1,2-Ph | $CH_2$—O | 2-thienyl | 35 |
| 3-((2-(Qn)vinyl))phenyl | $S(O)_2$ | 1,2-Ph | $CH_2$—O | phenyl | 36 |
| 3-((2-(Qn)vinyl))phenyl | O—$CH_2$ | 1,2-Ph | $CH_2$—O | 2-thienyl | 37 |
| 3-tolyl-D-3-phenyl | O—$CH_2$ | 1,2-Ph | $CH_2$—O | 2-thienyl | 38 |
| 3-((2-(Qn)vinyl))phenyl | CH(OH)—$CH_3$— | 1,2-Ph | $CH_2$—O | phenyl | 39 |
| 3-((2-(Qn)vinyl))phenyl | S | 1,2-Ph | $CH_2$—O | 2-thienyl | 40 |
| 3-((2-(Qn)vinyl))phenyl | O | 1,2-Ph | $CH_2$—O | phenyl | 41 |
| 3-((2-(Qn)vinyl))phenyl | C=O | 1,2-Ph | $CH_2$—O | 2-thienyl | 42 |
| 3-((2-(Qn)vinyl))phenyl | O | 1,2-Ph | $C(CH_3)_2$—O | 2-thienyl | 43 |
| 3-((2-(Qn)vinyl))phenyl | O | 1,2-Ph | $CH_2$—O | 2-thienyl | 44 |
| 2-naphthyl | $CH_2$ | 1,2-Ph | 1,2-c-propyl | 2-thienyl | 45 |
| 2-(6-benzyloxy)naphthyl | $CH_2$ | 1,2-Ph | CH=CH | 2-methoxy-5-bromophenyl | 46 |
| 2-naphthyl | $CH_2$ | 1,2-Ph | 1,2-c-propyl | 3,4-dichloro phenyl | 47 |
| 2-naphthyl | $CH_2$ | 1,2-Ph | 1,2-c-propyl | 4-fluoro phenyl | 48 |
| 2-naphthyl | $CH_2$ | 1,2-Ph | 1,2-c-propyl | 4-chloro phenyl | 49 |
| 2-naphthyl | $CH_2$ | 1,2-Ph | 1,2-c-propyl | 4-propyl phenyl | 50 |
| 2-naphthyl | $CH_2$ | 1,2-Ph | 1,2-c-propyl | 2,5-dichloro thienyl | 51 |
| 2-naphthyl | $CH_2$ | 1,2-Ph | 1,2-c-propyl | styryl | 52 |
| 2-naphthyl | $CH_2$ | 1,2-Ph | 1,2-c-propyl | 3-chloro-4-fluorophenyl | 53 |
| 2-naphthyl | $CH_2$ | 1,2-Ph | 1,2-c-propyl | 4-methoxy phenyl | 54 |
| 2-naphthyl | $CH_2$ | 1,2-Ph | 1,2-c-propyl | 3-bromo phenyl | 55 |
| 2-naphthyl | $CH_2$ | 1,2-Ph | 1,2-c-propyl | 2,5-dimethyl phenyl | 56 |
| 2-naphthyl | $CH_2$ | 1,2-Ph | 1,2-c-propyl | 2-nitro-4-chloro phenyl | 57 |
| 2-naphthyl | $CH_2$ | 1,2-Ph | 1,2-c-propyl | 2-carbomethoxy phenyl | 58 |
| 2-naphthyl | $CH_2$ | 1,2-Ph | 1,2-c-propyl | 2,4-difluoro phenyl | 59 |
| 2-naphthyl | $CH_2$ | 1,2-Ph | 1,2-c-propyl | 4-butyl-phenyl | 60 |
| 2-naphthyl | $CH_2$ | 1,2-Ph | 1,2-c-propyl | butyl | 61 |
| 2-naphthyl | $CH_2$ | 1,2-Ph | 1,2-c-propyl | 2,5-dimethoxy phenyl | 62 |
| 2-naphthyl | $CH_2$ | 1,2-Ph | 1,2-c-propyl | 3-trifluoro methylphenyl | 63 |
| 2-naphthyl | $CH_2$ | 1,2-Ph | 1,2-c-propyl | 3,5-difluoro phenyl | 64 |
| 2-naphthyl | $CH_2$ | 1,2-Ph | 1,2-c-propyl | 3,5-dichloro | 65 |

TABLE I-continued $$\text{R}^1\text{R}^2\text{R}^3\text{-HET}-\overset{\displaystyle A}{\underset{\displaystyle X-B}{|}}-\overset{\displaystyle O}{\underset{\displaystyle \|}{C}}-\text{NHSO}_2\text{R}^{19} \qquad \text{Ia}$$

(Compounds 1–323 and 347–454)

| $R^1R^2R^3$-Het | A | X | B | $R^{19}$ | Cpd |
|---|---|---|---|---|---|
| 2-naphthyl | $CH_2$ | 1,2-Ph | 1,2-c-propyl | 4-((1-hydroxy-1-methyl)ethyl) phenyl | 66 |
| 2-naphthyl | $CH_2$ | 1,2-Ph | 1,2-c-propyl | 4-(hydroxy methyl)phenyl | 67 |
| 2-naphthyl | $CH_2$ | 1,2-Ph | 1,2-c-propyl | 3-(hydroxy methyl)phenyl | 68 |
| 2-naphthyl | $CH_2$ | 1,2-Ph | 1,2-c-propyl | 4-(methyl sulfonyl)phenyl | 69 |
| 2-naphthyl | $CH_2$ | 1,2-Ph | 1,2-c-propyl | 3-(methyl sulfonyl)phenyl | 70 |
| 2-naphthyl | $CH_2$ | 1,2-Ph | 1,2-c-propyl | 4-(propyl sulfonyl)phenyl | 71 |
| 2-naphthyl | $CH_2$ | 1,2-Ph | 1,2-c-propyl | 4-((bis-trifluoro-methyl)-hydroxy methyl)phenyl | 72 |
| 2-naphthyl | $CH_2$ | 1,2-Ph | 1,2-c-propyl | 4-(benzyloxy) phenyl | 73 |
| 2-naphthyl | $CH_2$ | 1,2-Ph | 1,2-c-propyl | 4-((1-methoxy-1-methyl) ethyl)phenyl | 74 |
| 2-naphthyl | $CH_2$ | 1,2-Ph | 1,2-c-propyl | 4-dimethyl aminophenyl | 75 |
| 2-naphthyl | $CH_2$ | 1,2-Ph | 1,2-c-propyl | cyclohexyl | 76 |
| 2-naphthyl | $CH_2$ | 1,2-Ph | 1,2-c-propyl | cyclopentyl | 77 |
| 2-naphthyl | $CH_2$ | 1,2-Ph | 1,2-c-propyl | 4-morpholinyl | 78 |
| 2-naphthyl | $CH_2$ | 1,2-Ph | 1,2-c-propyl | 2-naphthyl | 79 |
| 2-naphthyl | $CH_2$ | 1,2-Ph | 1,2-c-propyl | 2-thiazolyl | 80 |
| 2-naphthyl | $CH_2$ | 1,2-Ph | 1,2-c-propyl | 1-imidazolyl | 81 |
| 2-naphthyl | $CH_2$ | 1,2-Ph | 1,2-c-propyl | 2-furanyl | 82 |
| 2-naphthyl | $CH_2$ | 1,2-Ph | 1,2-c-propyl | 3-(2-chloro)-furanyl | 83 |
| 2-naphthyl | $CH_2$ | 1,2-Ph | 1,2-c-propyl | 2-pyridinyl | 84 |
| 2-naphthyl | $CH_2$ | 1,2-Ph | 1,2-c-propyl | 2-(4-chloro) pyridinyl | 85 |
| 2-naphthyl | $CH_2$ | 1,2-Ph | 1,2-c-propyl | 3-indolyl | 86 |
| 2-naphthyl | $CH_2$ | 1,2-Ph | 1,2-c-propyl | 4-nitrophenyl | 87 |
| 2-naphthyl | $CH_2$ | 1,2-Ph | 1,2-c-propyl | 4-cyanophenyl | 88 |
| 2-naphthyl | $S(O)_2$ | 1,2-Ph | 1,2-c-propyl | 4-((1-hydroxy-1-methyl)ethyl) phenyl | 89 |
| 2-naphthyl | $S(O)_2$ | 1,2-Ph | 1,2-c-propyl | 4-(hydroxy methyl)phenyl | 90 |
| 2-naphthyl | $S(O)_2$ | 1,2-Ph | 1,2-c-propyl | 3-(hydroxy methyl)phenyl | 91 |
| 2-naphthyl | $S(O)_2$ | 1,2-Ph | 1,2-c-propyl | 2,5-dimethyl phenyl | 92 |
| 2-naphthyl | $S(O)_2$ | 1,2-Ph | 1,2-c-propyl | 2-carbomethoxy phenyl | 93 |
| 2-naphthyl | $S(O)_2$ | 1,2-Ph | 1,2-c-propyl | 2,4-difluoro phenyl | 94 |
| 2-naphthyl | $S(O)_2$ | 1,2-Ph | 1,2-c-propyl | 4-(methyl sulfonyl)phenyl | 95 |
| 2-naphthyl | $S(O)_2$ | 1,2-Ph | 1,2-c-propyl | 3-(methyl sulfonyl)phenyl | 96 |
| 2-naphthyl | $S(O)_2$ | 1,2-Ph | 1,2-c-propyl | 4-(propyl sulfonyl)phenyl | 97 |
| 2-naphthyl | $S(O)_2$ | 1,2-Ph | 1,2-c-propyl | 4-butyl-phenyl | 98 |
| 2-naphthyl | $S(O)_2$ | 1,2-Ph | 1,2-c-propyl | 3,5-di-$(CF_3)$ phenyl | 99 |
| 2-naphthyl | $S(O)_2$ | 1,2-Ph | 1,2-c-propyl | 4-((bis-trifluoro methyl)-hydroxy methyl)phenyl | 100 |
| 2-naphthyl | $S(O)_2$ | 1,2-Ph | 1,2-c-propyl | 3-bromophenyl | 101 |
| 2-naphthyl | $S(O)_2$ | 1,2-Ph | 1,2-c-propyl | 4-(benzyloxy) phenyl | 102 |

TABLE I-continued $R^1R^2R^3$-HET-A-X-B-C(O)-NHSO$_2$R$^{19}$   Ia (Compounds 1–323 and 347–454)

| R$^1$R$^2$R$^3$-Het | A | X | B | R$^{19}$ | Cpd |
|---|---|---|---|---|---|
| 2-naphthyl | S(O)$_2$ | 1,2-Ph | 1,2-c-propyl | 2-nitro-4-chloro phenyl | 103 |
| 2-naphthyl | S(O)$_2$ | 1,2-Ph | 1,2-c-propyl | 4-isopropyl phenyl | 104 |
| 2-naphthyl | S(O)$_2$ | 1,2-Ph | 1,2-c-propyl | 4-((1-methoxy-1-methyl) ethyl)phenyl | 105 |
| 2-naphthyl | S(O)$_2$ | 1,2-Ph | 1,2-c-propyl | 4-methoxy phenyl | 106 |
| 2-naphthyl | S(O)$_2$ | 1,2-Ph | 1,2-c-propyl | 4-dimethyl aminophenyl | 107 |
| 2-naphthyl | S(O)$_2$ | 1,2-Ph | 1,2-c-propyl | 3,4-dichloro phenyl | 108 |
| 2-naphthyl | S(O)$_2$ | 1,2-Ph | 1,2-c-propyl | 3,4-difluoro phenyl | 109 |
| 2-naphthyl | S(O)$_2$ | 1,2-Ph | 1,2-c-propyl | 4-fluorophenyl | 110 |
| 2-naphthyl | S(O)$_2$ | 1,2-Ph | 1,2-c-propyl | cyclohexyl | 111 |
| 2-naphthyl | S(O)$_2$ | 1,2-Ph | 1,2-c-propyl | cyclopentyl | 112 |
| 2-naphthyl | S(O)$_2$ | 1,2-Ph | 1,2-c-propyl | 4-morpholinyl | 113 |
| 2-naphthyl | S(O)$_2$ | 1,2-Ph | 1,2-c-propyl | butyl | 114 |
| 2-naphthyl | S(O)$_2$ | 1,2-Ph | 1,2-c-propyl | 4-chlorophenyl | 115 |
| 2-naphthyl | S(O)$_2$ | 1,2-Ph | 1,2-c-propyl | 4-propylphenyl | 116 |
| 2-naphthyl | S(O)$_2$ | 1,2-Ph | 1,2-c-propyl | 2-naphthyl | 117 |
| 2-naphthyl | S(O)$_2$ | 1,2-Ph | 1,2-c-propyl | 2-thiazolyl | 118 |
| 2-naphthyl | S(O)$_2$ | 1,2-Ph | 1,2-c-propyl | 1-imidazolyl | 119 |
| 2-naphthyl | S(O)$_2$ | 1,2-Ph | 1,2-c-propyl | 2,5-dimethoxy phenyl | 120 |
| 2-naphthyl | S(O)$_2$ | 1,2-Ph | 1,2-c-propyl | 3-trifluoro methylphenyl | 121 |
| 2-naphthyl | S(O)$_2$ | 1,2-Ph | 1,2-c-propyl | 2,5-dichloro-3-thienyl | 122 |
| 2-naphthyl | S(O)$_2$ | 1,2-Ph | 1,2-c-propyl | 2-furanyl | 123 |
| 2-naphthyl | S(O)$_2$ | 1,2-Ph | 1,2-c-propyl | 3-(2-chloro)-furanyl | 124 |
| 2-naphthyl | S(O)$_2$ | 1,2-Ph | 1,2-c-propyl | 2-pyridinyl | 125 |
| 2-naphthyl | S(O)$_2$ | 1,2-Ph | 1,2-c-propyl | 2-styryl | 126 |
| 2-naphthyl | S(O)$_2$ | 1,2-Ph | 1,2-c-propyl | 3,5-difluoro-phenyl | 127 |
| 2-naphthyl | S(O)$_2$ | 1,2-Ph | 1,2-c-propyl | 3,5-dichloro-phenyl | 128 |
| 2-naphthyl | S(O)$_2$ | 1,2-Ph | 1,2-c-propyl | 2-(4-chloro) pyridinyl | 129 |
| 2-naphthyl | S(O)$_2$ | 1,2-Ph | 1,2-c-propyl | 3-indolyl | 130 |
| 2-naphthyl | S(O)$_2$ | 1,2-Ph | 1,2-c-propyl | 4-nitrophenyl | 131 |
| 2-naphthyl | S(O)$_2$ | 1,2-Ph | 1,2-c-propyl | 4-cyanophenyl | 132 |
| 2-naphthyl | S(O)$_2$ | 1,2-Ph | 1,2-c-propyl | 3-chloro-4-fluorophenyl | 133 |
| 3-methylindol-1-yl | CH$_2$ | 1,2-Ph | 1,2-c-propyl | 3,5-di-(CF$_3$)-phenyl | 134 |
| 3-methylindol-1-yl | CH$_2$ | 1,2-Ph | 1,2-c-propyl | 4-isopropyl phenyl | 135 |
| 3-methylindol-1-yl | CH$_2$ | 1,2-Ph | 1,2-c-propyl | 3,4-dichloro phenyl | 136 |
| 3-methylindol-1-yl | CH$_2$ | 1,2-Ph | 1,2-c-propyl | 3,4-difluoro phenyl | 137 |
| 3-methylindol-1-yl | CH$_2$ | 1,2-Ph | 1,2-c-propyl | 4-fluorophenyl | 138 |
| 3-methylindol-1-yl | CH$_2$ | 1,2-Ph | 1,2-c-propyl | 4-chlorophenyl | 139 |
| 3-methylindol-1-yl | CH$_2$ | 1,2-Ph | 1,2-c-propyl | 4-propylphenyl | 140 |
| 3-methylindol-1-yl | CH$_2$ | 1,2-Ph | 1,2-c-propyl | 2,5-dichloro-3-thienyl | 141 |
| 3-methylindol-1-yl | CH$_2$ | 1,2-Ph | 1,2-c-propyl | 2-styryl | 142 |
| 3-methylindol-1-yl | CH$_2$ | 1,2-Ph | 1,2-c-propyl | 3-chloro-4-fluoro phenyl | 143 |

TABLE I-continued

Ia

R¹R²R³-HET–A–X–B–C(=O)–NHSO₂R¹⁹

(Compounds 1–323 and 347–454)

| R¹R²R³-Het | A | X | B | R¹⁹ | Cpd |
|---|---|---|---|---|---|
| 3-methylindol-1-yl | CH₂ | 1,2-Ph | 1,2-c-propyl | 4-methoxy phenyl | 144 |
| 3-methylindol-1-yl | CH₂ | 1,2-Ph | 1,2-c-propyl | 3-bromophenyl | 145 |
| 3-methylindol-1-yl | CH₂ | 1,2-Ph | 1,2-c-propyl | 2,5-dimethyl phenyl | 146 |
| 3-methylindol-1-yl | CH₂ | 1,2-Ph | 1,2-c-propyl | 2-nitro-4-chloro phenyl | 147 |
| 3-methylindol-1-yl | CH₂ | 1,2-Ph | 1,2-c-propyl | 2-carbomethoxy phenyl | 148 |
| 3-methylindol-1-yl | CH₂ | 1,2-Ph | 1,2-c-propyl | 2,4-difluoro phenyl | 149 |
| 3-methylindol-1-yl | CH₂ | 1,2-Ph | 1,2-c-propyl | 4-butylphenyl | 150 |
| 3-methylindol-1-yl | CH₂ | 1,2-Ph | 1,2-c-propyl | n-butyl | 151 |
| 3-methylindol-1-yl | CH₂ | 1,2-Ph | 1,2-c-propyl | 2,5-dimethoxy phenyl | 152 |
| 3-methylindol-1-yl | CH₂ | 1,2-Ph | 1,2-c-propyl | 3-trifluoro methylphenyl | 153 |
| 3-methylindol-1-yl | CH₂ | 1,2-Ph | 1,2-c-propyl | 3,5-difluoro phenyl | 154 |
| 3-methylindol-1-yl | CH₂ | 1,2-Ph | 1,2-c-propyl | 3,5-dichloro phenyl | 155 |
| 3-methylindol-1-yl | CH₂ | 1,2-Ph | 1,2-c-propyl | 4-((1-hydroxy-1-methyl)ethyl) phenyl | 156 |
| 3-methylindol-1-yl | CH₂ | 1,2-Ph | 1,2-c-propyl | 4-(hydroxy methyl)phenyl | 157 |
| 3-methylindol-1-yl | CH₂ | 1,2-Ph | 1,2-c-propyl | 3-(hydroxy methyl)phenyl | 158 |
| 3-methylindol-1-yl | CH₂ | 1,2-Ph | 1,2-c-propyl | 4-(methyl sulfonyl)phenyl | 159 |
| 3-methylindol-1-yl | CH₂ | 1,2-Ph | 1,2-c-propyl | 3-(methyl sulfonyl)phenyl | 160 |
| 3-methylindol-1-yl | CH₂ | 1,2-Ph | 1,2-c-propyl | 4-(propyl sulfonyl)phenyl | 161 |
| 3-methylindol-1-yl | CH₂ | 1,2-Ph | 1,2-c-propyl | 4-((bis-trifluoro methyl)hydroxy methyl)phenyl | 162 |
| 3-methylindol-1-yl | CH₂ | 1,2-Ph | 1,2-c-propyl | 4-(benzyloxy) phenyl | 163 |
| 3-methylindol-1-yl | CH₂ | 1,2-Ph | 1,2-c-propyl | 4-((1-methoxy-1-methyl) ethyl)phenyl | 164 |
| 3-methylindol-1-yl | CH₂ | 1,2-Ph | 1,2-c-propyl | 4-dimethyl aminophenyl | 165 |
| 3-methylindol-1-yl | CH₂ | 1,2-Ph | 1,2-c-propyl | cyclohexyl | 166 |
| 3-methylindol-1-yl | CH₂ | 1,2-Ph | 1,2-c-propyl | cyclopentyl | 167 |
| 3-methylindol-1-yl | CH₂ | 1,2-Ph | 1,2-c-propyl | 4-morpholinyl | 168 |
| 3-methylindol-1-yl | CH₂ | 1,2-Ph | 1,2-c-propyl | 2-naphthyl | 169 |
| 3-methylindol-1-yl | CH₂ | 1,2-Ph | 1,2-c-propyl | 2-thiazolyl | 170 |
| 3-methylindol-1-yl | CH₂ | 1,2-Ph | 1,2-c-propyl | 1-imidazolyl | 171 |
| 3-methylindol-1-yl | CH₂ | 1,2-Ph | 1,2-c-propyl | 2-furanyl | 172 |
| 3-methylindol-1-yl | CH₂ | 1,2-Ph | 1,2-c-propyl | 3-(2-chloro)-furanyl | 173 |
| 3-methylindol-1-yl | CH₂ | 1,2-Ph | 1,2-c-propyl | 2-pyridinyl | 174 |
| 3-methylindol-1-yl | CH₂ | 1,2-Ph | 1,2-c-propyl | 2-(4-chloro) pyridinyl | 175 |

TABLE I-continued $$\underset{X-B}{\overset{R^1R^2R^3-HET}{\underset{A}{\diagdown}}}\overset{O}{\underset{}{\overset{\|}{C}}}NHSO_2R^{19}$$ Ia (Compounds 1–323 and 347–454)

| $R^1R^2R^3$-Het | A | X | B | $R^{19}$ | Cpd |
|---|---|---|---|---|---|
| 3-methylindol-1-yl | CH$_2$ | 1,2-Ph | 1,2-c-propyl | 3-indolyl | 176 |
| 3-methylindol-1-yl | CH$_2$ | 1,2-Ph | 1,2-c-propyl | 4-nitrophenyl | 177 |
| 3-methylindol-1-yl | CH$_2$ | 1,2-Ph | 1,2-c-propyl | 4-cyanophenyl | 178 |
| 3-methylindol-1-yl | SO$_2$ | 1,2-Ph | 1,2-c-propyl | 3,5-di-(CF$_3$) phenyl | 179 |
| 3-methylindol-1-yl | SO$_2$ | 1,2-Ph | 1,2-c-propyl | 4-isopropyl phenyl | 180 |
| 3-methylindol-1-yl | SO$_2$ | 1,2-Ph | 1,2-c-propyl | 3,4-dichloro phenyl | 181 |
| 3-methylindol-1-yl | SO$_2$ | 1,2-Ph | 1,2-c-propyl | 3,4-difluoro phenyl | 182 |
| 3-methylindol-1-yl | SO$_2$ | 1,2-Ph | 1,2-c-propyl | 4-fluorophenyl | 183 |
| 3-methylindol-1-yl | SO$_2$ | 1,2-Ph | 1,2-c-propyl | 4-chlorophenyl | 184 |
| 3-methylindol-1-yl | SO$_2$ | 1,2-Ph | 1,2-c-propyl | 4-propylphenyl | 185 |
| 3-methylindol-1-yl | SO$_2$ | 1,2-Ph | 1,2-c-propyl | 2,5-dichloro-3-thienyl | 186 |
| 3-methylindol-1-yl | SO$_2$ | 1,2-Ph | 1,2-c-propyl | 2-styryl | 187 |
| 3-methylindol-1-yl | SO$_2$ | 1,2-Ph | 1,2-c-propyl | 3-chloro-4-fluorophenyl | 188 |
| 3-methylindol-1-yl | SO$_2$ | 1,2-Ph | 1,2-c-propyl | 4-methoxy phenyl | 189 |
| 3-methylindol-1-yl | SO$_2$ | 1,2-Ph | 1,2-c-propyl | 3-bromo phenyl | 190 |
| 3-methylindol-1-yl | SO$_2$ | 1,2-Ph | 1,2-c-propyl | 2,5-dimethyl phenyl | 191 |
| 3-methylindol-1-yl | SO$_2$ | 1,2-Ph | 1,2-c-propyl | 2-nitro-4-chloro phenyl | 192 |
| 3-methylindol-1-yl | SO$_2$ | 1,2-Ph | 1,2-c-propyl | 2-carbomethoxy phenyl | 193 |
| 3-methylindol-1-yl | SO$_2$ | 1,2-Ph | 1,2-c-propyl | 2,4-difluoro phenyl | 194 |
| 3-methylindol-1-yl | SO$_2$ | 1,2-Ph | 1,2-c-propyl | 4-butylphenyl | 195 |
| 3-methylindol-1-yl | SO$_2$ | 1,2-Ph | 1,2-c-propyl | n-butyl | 196 |
| 3-methylindol-1-yl | SO$_2$ | 1,2-Ph | 1,2-c-propyl | 2,5-dimethoxy phenyl | 197 |
| 3-methylindol-1-yl | SO$_2$ | 1,2-Ph | 1,2-c-propyl | 3-trifluoromethyl phenyl | 198 |
| 3-methylindol-1-yl | SO$_2$ | 1,2-Ph | 1,2-c-propyl | 3,5-difluoro phenyl | 199 |
| 1-(3-methyl)indolyl | SO$_2$ | 1,2-Ph | 1,2-c-propyl | 3,5-dichloro phenyl | 200 |
| 3-methylindol-1-yl | SO$_2$ | 1,2-Ph | 1,2-c-propyl | 4-((1-hydroxy-1-methyl)ethyl) phenyl | 201 |
| 3-methylindol-1-yl | SO$_2$ | 1,2-Ph | 1,2-c-propyl | 4-(hydroxy methyl)phenyl | 202 |
| 3-methylindol-1-yl | SO$_2$ | 1,2-Ph | 1,2-c-propyl | 3-(hydroxy methyl)phenyl | 203 |
| 3-methylindol-1-yl | SO$_2$ | 1,2-Ph | 1,2-c-propyl | 4-(methyl sulfonyl)phenyl | 204 |
| 3-methylindol-1-yl | SO$_2$ | 1,2-Ph | 1,2-c-propyl | 3-(methyl sulfonyl)phenyl | 205 |
| 3-methylindol-1-yl | SO$_2$ | 1,2-Ph | 1,2-c-propyl | 4-(propyl sulfonyl)phenyl | 206 |
| 3-methylindol-1-yl | SO$_2$ | 1,2-Ph | 1,2-c-propyl | 4-((bis-trifluoro methyl)hydroxy methyl)phenyl | 207 |
| 3-methylindol-1-yl | SO$_2$ | 1,2-Ph | 1,2-c-propyl | 4-(benzyloxy) | 208 |

TABLE I-continued $$\text{R}^1\text{R}^2\text{R}^3\text{-HET} - \underset{\underset{X-B}{A}}{\phantom{X}} - \underset{\underset{\text{NHSO}_2\text{R}^{19}}{\parallel}}{C} = O \qquad \text{Ia}$$

(Compounds 1–323 and 347–454)

| R¹R²R³-Het | A | X | B | R¹⁹ | Cpd |
|---|---|---|---|---|---|
| 1-yl | | | | phenyl | |
| 3-methylindol-1-yl | SO$_2$ | 1,2-Ph | 1,2-c-propyl | 4-((1-methoxy-1-methyl)ethyl)-phenyl | 209 |
| 3-methylindol-1-yl | SO$_2$ | 1,2-Ph | 1,2-c-propyl | 4-dimethyl aminophenyl | 210 |
| 3-methylindol-1-yl | SO$_2$ | 1,2-Ph | 1,2-c-propyl | cyclohexyl | 211 |
| 3-methylindol-1-yl | SO$_2$ | 1,2-Ph | 1,2-c-propyl | cyclopentyl | 212 |
| 3-methylindol-1-yl | SO$_2$ | 1,2-Ph | 1,2-c-propyl | 4-morpholinyl | 213 |
| 3-methylindol-1-yl | SO$_2$ | 1,2-Ph | 1,2-c-propyl | 2-naphthyl | 214 |
| 3-methylindol-1-yl | SO$_2$ | 1,2-Ph | 1,2-c-propyl | 2-thiazolyl | 215 |
| 3-methylindol-1-yl | SO$_2$ | 1,2-Ph | 1,2-c-propyl | 1-imidazolyl | 216 |
| 3-methylindol-1-yl | SO$_2$ | 1,2-Ph | 1,2-c-propyl | 2-furanyl | 217 |
| 3-methylindol-1-yl | SO$_2$ | 1,2-Ph | 1,2-c-propyl | 3-(2-chloro-furanyl | 218 |
| 3-methylindol-1-yl | SO$_2$ | 1,2-Ph | 1,2-c-propyl | 2-pyridinyl | 219 |
| 3-methylindol-1-yl | SO$_2$ | 1,2-Ph | 1,2-c-propyl | 2-(4-chloro) pyridinyl | 220 |
| 3-methylindol-1-yl | SO$_2$ | 1,2-Ph | 1,2-c-propyl | 3-indolyl | 221 |
| 3-methylindol-1-yl | SO$_2$ | 1,2-Ph | 1,2-c-propyl | 4-nitrophenyl | 222 |
| 3-methylindol-1-yl | SO$_2$ | 1,2-Ph | 1,2-c-propyl | 4-cyanophenyl | 223 |
| 2-naphthyl | CH$_2$ | 1,2-Ph | CH=CH | 3,5-di-(CF$_3$) phenyl | 224 |
| 2-naphthyl | CH$_2$ | 1,2-Ph | CH=CH | 4-isopropyl phenyl | 225 |
| 2-naphthyl | CH$_2$ | 1,2-Ph | CH=CH | 2,3-dichloro phenyl | 226 |
| 2-naphthyl | CH$_2$ | 1,2-Ph | CH=CH | 3,4-difluoro phenyl | 227 |
| 2-naphthyl | CH$_2$ | 1,2-Ph | CH=CH | 4-chlorophenyl | 228 |
| 2-naphthyl | CH$_2$ | 1,2-Ph | CH=CH | 4-fluorophenyl | 229 |
| 2-naphthyl | CH$_2$ | 1,2-Ph | CH=CH | 2,5-dichloro-3-thienyl | 230 |
| 2-naphthyl | CH$_2$ | 1,2-Ph | CH=CH | 3-chloro-4-fluoro phenyl | 231 |
| 2-naphthyl | CH$_2$ | 1,2-Ph | CH=CH | 4-methoxy phenyl | 232 |
| 2-naphthyl | CH$_2$ | 1,2-Ph | CH=CH | butyl | 233 |
| 2-naphthyl | CH$_2$ | 1,2-Ph | CH=CH | 3-trifluoro methylphenyl | 234 |
| 2-naphthyl | CH$_2$ | 1,2-Ph | CH=CH | 4-((1-hydroxy-1-methyl)ethyl) phenyl | 235 |
| 2-naphthyl | CH$_2$ | 1,2-Ph | CH=CH | 4-(methyl sufonyl)phenyl | 236 |
| 2-naphthyl | CH$_2$ | 1,2-Ph | CH=CH | 4-(benzyloxy) phenyl | 237 |
| 2-naphthyl | CH$_2$ | 1,2-Ph | CH=CH | cyclohexyl | 238 |
| 2-naphthyl | CH$_2$ | 1,2-Ph | CH=CH | 4-morpholinyl | 239 |
| 2-naphthyl | CH$_2$ | 1,2-Ph | CH=CH | 2-thiazolyl | 240 |
| 2-naphthyl | CH$_2$ | 1,2-Ph | CH=CH | 2-furanyl | 241 |
| 2-naphthyl | CH$_2$ | 1,2-Ph | CH=CH | 2-pyridinyl | 242 |
| 2-naphthyl | CH$_2$ | 1,2-Ph | CH=CH | 4-cyanophenyl | 243 |
| 2-naphthyl | SO$_2$ | 1,2-Ph | CH=CH | 3,5-di-(CF$_3$) phenyl | 244 |
| 2-naphthyl | SO$_2$ | 1,2-Ph | CH=CH | 4-isopropyl | 245 |

TABLE I-continued

Ia $$R^1R^2R^3\text{-HET}-A-X-B-\underset{\underset{NHSO_2R^{19}}{\|}}{C}=O$$

(Compounds 1–323 and 347–454)

| $R^1R^2R^3$-Het | A | X | B | $R^{19}$ | Cpd |
|---|---|---|---|---|---|
| 2-naphthyl | SO₂ | 1,2-Ph | CH=CH | 2,3-dichloro phenyl | 246 |
| 2-naphthyl | SO₂ | 1,2-Ph | CH=CH | 3,4-difluoro phenyl | 247 |
| 2-naphthyl | SO₂ | 1,2-Ph | CH=CH | 4-chlorophenyl | 248 |
| 2-naphthyl | SO₂ | 1,2-Ph | CH=CH | 4-fluorophenyl | 249 |
| 2-naphthyl | SO₂ | 1,2-Ph | CH=CH | 2,5-dichloro-3-thienyl | 250 |
| 2-naphthyl | SO₂ | 1,2-Ph | CH=CH | 3-chloro-4-fluorophenyl | 251 |
| 2-naphthyl | SO₂ | 1,2-Ph | CH=CH | 4-methoxy phenyl | 252 |
| 2-naphthyl | SO₂ | 1,2-Ph | CH=CH | butyl | 253 |
| 2-naphthyl | SO₂ | 1,2-Ph | CH=CH | 3-trifluoro methylphenyl | 254 |
| 2-naphthyl | SO₂ | 1,2-Ph | CH=CH | 4-((1-hydroxy-1-methyl)ethyl)phenyl | 255 |
| 2-naphthyl | SO₂ | 1,2-Ph | CH=CH | 4-(methyl sufonyl)phenyl | 256 |
| 2-naphthyl | SO₂ | 1,2-Ph | CH=CH | 4-(benzyloxy) phenyl | 257 |
| 2-naphthyl | SO₂ | 1,2-Ph | CH=CH | cyclohexyl | 258 |
| 2-naphthyl | SO₂ | 1,2-Ph | CH=CH | 4-morpholinyl | 259 |
| 2-naphthyl | SO₂ | 1,2-Ph | CH=CH | 2-thiazolyl | 260 |
| 2-naphthyl | SO₂ | 1,2-Ph | CH=CH | 2-furanyl | 261 |
| 2-naphthyl | SO₂ | 1,2-Ph | CH=CH | 2-pyridinyl | 262 |
| 2-naphthyl | SO₂ | 1,2-Ph | CH=CH | 4-cyanophenyl | 263 |
| 2-naphthyl | CH₂—O | 1,2-Ph | CH=CH | 3,5-di-(CF₃) phenyl | 264 |
| 2-naphthyl | CH₂—O | 1,2-Ph | CH=CH | 4-isopropyl phenyl | 265 |
| 2-naphthyl | CH₂—O | 1,2-Ph | CH=CH | 2,3-dichloro phenyl | 266 |
| 2-naphthyl | CH₂—O | 1,2-Ph | CH=CH | 3,4-difluoro phenyl | 267 |
| 2-naphthyl | O—CH₂ | 1,2-Ph | CH=CH | 3,5-di-(CF₃) phenyl | 268 |
| 2-naphthyl | O—CH₂ | 1,2-Ph | CH=CH | 4-isopropyl phenyl | 269 |
| 2-naphthyl | O—CH₂ | 1,2-Ph | CH=CH | 2,3-dichloro phenyl | 270 |
| 2-naphthyl | O—CH₂ | 1,2-Ph | CH=CH | 3,4-difluoro phenyl | 271 |
| 2-naphthyl | S | 1,2-Ph | CH=CH | 3,5-di-(CF₃) phenyl | 272 |
| 2-naphthyl | S | 1,2-Ph | CH=CH | 4-isopropyl phenyl | 273 |
| 2-naphthyl | S | 1,2-Ph | CH=CH | 2,3-dichloro phenyl | 274 |
| 2-naphthyl | S | 1,2-Ph | CH=CH | 3,4-difluoro phenyl | 275 |
| 2-(6-benzyloxy) naphthyl | SO₂ | 1,2-Ph | CH=CH | 2-thienyl | 276 |
| 2-(6-benzyloxy) naphthyl | S | 1,2-Ph | CH=CH | 2-thienyl | 277 |
| 2-(6-benzyloxy) naphthyl | SO₂ | 1,2-Ph | 1,2-c-propyl | 2-thienyl | 278 |
| 2-(6-benzyloxy) naphthyl | S | 1,2-Ph | 1,2-c-propyl | 2-thienyl | 279 |
| 2-(5-benzyloxy) naphthyl | SO₂ | 1,2-Ph | CH=CH | 2-thienyl | 280 |
| 2-(5-benzyloxy) naphthyl | S | 1,2-Ph | CH=CH | 2-thienyl | 281 |
| 2-(5-benzyloxy) naphthyl | SO₂ | 1,2-Ph | 1,2-c-propyl | 2-thienyl | 282 |

TABLE I-continued $$\text{R}^1\text{R}^2\text{R}^3\text{-HET}\diagdown\underset{\text{X}-\text{B}}{\text{A}}\diagdown\overset{\text{O}}{\underset{\|}{\text{C}}}-\text{NHSO}_2\text{R}^{19}$$

Ia (Compounds 1–323 and 347–454)

| $R^1R^2R^3$-Het | A | X | B | $R^{19}$ | Cpd |
|---|---|---|---|---|---|
| 2-(5-benzyloxy)naphthyl | S | 1,2-Ph | 1,2-c-propyl | 2-thienyl | 283 |
| 2-(6-(4-trifluoromethyl)benzyloxy))naphthyl | SO₂ | 1,2-Ph | CH=CH | 2-thienyl | 284 |
| 2-(6-(4-trifluoromethyl)benzyloxy))naphthyl | CH₂ | 1,2-Ph | CH=CH | 2-thienyl | 285 |
| 2-(6-(4-trifluoromethyl)benzyloxy))naphthyl | CH₂ | 1,2-Ph | 1,2-c-propyl | 2-thienyl | 286 |
| 2-(6-(4-trifluoromethyl)benzyloxy))naphthyl | CH₂ | 1,2-Ph | 1,2-c-propyl | 2-thienyl | 287 |
| 1-(6-benzyloxy)naphthyl | SO₂ | 1,2-Ph | CH=CH | 2-thienyl | 288 |
| 1-(6-benzyloxy)naphthyl | CH₂ | 1,2-Ph | CH=CH | 2-thienyl | 289 |
| 2-(6-(3,4-difluorobenzyloxy))naphthyl | SO₂ | 1,2-Ph | CH=CH | 2-thienyl | 290 |
| 2-(6-(3,4-difluorobenzyloxy))naphthyl | CH₂ | 1,2-Ph | CH=CH | 2-thienyl | 291 |
| 2-(6-(4-fluorobenzyloxy))naphthyl | CH₂ | 1,2-Ph | 1,2-c-propyl | 2-thienyl | 292 |
| 2-(7-benzyloxy)naphthyl | SO₂ | 1,2-Ph | CH=CH | 2-thienyl | 293 |
| 2-(6-(3,4-difluorobenzyloxy))naphthyl | SO₂ | 1,2-Ph | CH=CH | 3,4-difluorophenyl | 294 |
| 2-(6-(3,4-difluorobenzyloxy))naphthyl | CH₂ | 1,2-Ph | CH=CH | 3,4-difluorophenyl | 295 |
| 2-(6-(4-fluorobenzyloxy))naphthyl | CH₂ | 1,2-Ph | 1,2-c-propyl | 3,4-difluorophenyl | 296 |
| 2-(7-benzyloxy)naphthyl | SO₂ | 1,2-Ph | CH=CH | 3,5-di-(CF₃)phenyl | 297 |
| 2-(6-(3,4-difluorobenzyloxy))naphthyl | SO₂ | 1,2-Ph | CH=CH | 3,5-di-(CF₃)phenyl | 298 |
| 2-(6-(3,4-difluorobenzyloxy))naphthyl | CH₂ | 1,2-Ph | CH=CH | 3,5-di-(CF₃)phenyl | 299 |
| 2-(7-benzyloxy)naphthyl | SO₂ | 1,2-Ph | 1,2-c-propyl | 3,4-difluorophenyl | 300 |
| 2-naphthyl | CH₂ | 1,2-Ph | CH=CH | 2-methoxy-5-bromophenyl | 301 |
| 2-naphthyl | CH₂ | 4-Cl-1,2-Ph | CH=CH | 2-methoxy-5-bromophenyl | 302 |
| 2-naphthyl | CH₂ | 4-Cl-1,2-Ph | CH=CH | 2-thienyl | 303 |
| 2-naphthyl | SO | 1,2-Ph | CH=CH | 2-methoxy-5-bromophenyl | 304 |
| 2-naphthyl | SO₂ | 1,2-Ph | CH=CH | 2-methoxy-5-bromophenyl | 305 |
| 2-naphthyl | O | 1,2-Ph | CH=CH | 2-methoxy-5-bromophenyl | 306 |
| 2-(5-benzyloxy)naphthyl | CH₂ | 1,2-Ph | CH=CH | 2-methoxy-5-bromophenyl | 307 |
| 2-(5-benzyloxy)naphthyl | SO₂ | 1,2-Ph | CH=CH | 2-methoxy-5-bromophenyl | 308 |
| 2-(5-benzyloxy)naphthyl | S | 1,2-Ph | CH=CH | 2-methoxy-5-bromophenyl | 309 |
| 2-naphthyl | CH₂ | 1,2-Ph | 1,2-c-propyl | 2-methoxy-5-bromophenyl | 310 |

TABLE I-continued

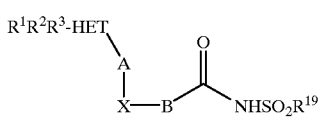

(Compounds 1–323 and 347–454)

| $R^1R^2R^3$-Het | A | X | B | $R^{19}$ | Cpd |
|---|---|---|---|---|---|
| 1,2-Ph | SO$_2$ | 1,2-Ph | 1,2-c-propyl | 2-methoxy-5-bromophenyl | 311 |
| 2-naphthyl | S | 1,2-Ph | 1,2-c-propyl | 2-methoxy-5-bromophenyl | 312 |
| 2-naphthyl | CH$_2$—O | 1,2-Ph | CH=CH | 2-methoxy-5-bromophenyl | 313 |
| 2-naphthyl | S | 1,2-Ph | CH=CH | 2-methoxy-5-bromophenyl | 314 |
| 3-methyl indol-1-yl | SO$_2$ | 1,2-Ph | 1,2-c-propyl | 2-methoxy-5-bromophenyl | 315 |
| 3-methyl indol-1-yl | S | 1,2-Ph | 1,2-c-propyl | 2-methoxy-5-bromophenyl | 316 |
| 3-methyl indol-1-yl | CH$_2$—O | 1,2-Ph | CH=CH | 2-methoxy-5-bromophenyl | 317 |
| 3-methyl indol-1-yl | S | 1,2-Ph | CH=CH | 2-methoxy-5-bromophenyl | 318 |
| 3-methyl indol-1-yl | O—CH$_2$ | 1,2-Ph | 1,2-c-propyl | 2-methoxy-5-bromophenyl | 319 |
| 3-methyl indol-1-yl | SO | 1,2-Ph | 1,2-c-propyl | 2-methoxy-5-bromophenyl | 320 |
| 3-methyl indol-1-yl | CH$_2$—O | 4-Cl-1,2-Ph | CH=CH | 2-methoxy-5-bromophenyl | 321 |
| 3-methyl indol-1-yl | S | 4-Cl-1,2-Ph | CH=CH | 2-methoxy-5-bromophenyl | 322 |
| 3-methyl indol-1-yl | SO$_2$ | 4-Cl-1,2-Ph | 1,2-c-propyl | 2-methoxy-5-bromophenyl | 323 |
| 2-(7-fluoro) naphthyl | SO$_2$ | 4-Cl-1,2-Ph | CH=CH | 2-thienyl | 347 |
| 2-(7-fluoro) naphthyl | O | 4-Cl-1,2-Ph | CH=CH | 2-thienyl | 348 |
| 2-(7-fluoro) naphthyl | S | 4-Cl-1,2-Ph | CH=CH | 2-thienyl | 349 |
| 2-(7-fluoro) naphthyl | CH$_2$ | 4-Cl-1,2-Ph | CH=CH | 2-thienyl | 350 |
| 2-(7-fluoro) naphthyl | CH$_2$ | 6-Cl-1,2-Ph | CH=CH | 2-thienyl | 351 |
| 2-(7-fluoro) naphthyl | CH$_2$ | 4-Cl-1,2-Ph | 1,2-c-Pr | 2-thienyl | 352 |
| 2-(7-fluoro) naphthyl | CH$_2$ | 3-Cl-1,2-Ph | CH=CH | 2-thienyl | 353 |
| 2-(7-fluoro) naphthyl | SO$_2$ | 4-Cl-1,2-Ph | CH=CH | 2-methoxy-5-bromophenyl | 354 |
| 2-(7-fluoro) naphthyl | O | 4-Cl-1,2-Ph | CH=CH | 2-methoxy-5-bromophenyl | 355 |
| 2-(7-fluoro) naphthyl | S | 4-Cl-1,2-Ph | CH=CH | 2-methoxy-5-bromophenyl | 356 |
| 2-naphthyl | CH$_2$ | 4,5-Cl$_2$-1,2-Ph | CH=CH | 2-methoxy-5-bromophenyl | 357 |
| 2-(7-fluoro) naphthyl | CH$_2$ | 6-Cl-1,2-Ph | CH=CH | 2-methoxy-5-bromophenyl | 358 |
| 2-(7-fluoro) naphthyl | CH$_2$ | 4-Cl-1,2-Ph | 1,2-c-Pr | 2-methoxy-5-bromophenyl | 359 |
| 2-(7-fluoro) naphthyl | CH$_2$ | 3-Cl-1,2-Ph | CH=CH | 2-methoxy-5-bromophenyl | 360 |
| 2-(7-fluoro) naphthyl | SO$_2$ | 4-Cl-1,2-Ph | CH=CH | 2-trifluoro methoxy-5-chlorophenyl | 361 |
| 2-(7-fluoro) naphthyl | O | 4-Cl-1,2-Ph | CH=CH | 2-trifluoro methoxy-5-chlorophenyl | 362 |
| 2-(7-fluoro) naphthyl | S | 4-Cl-1,2-Ph | CH=CH | 2-trifluoro methoxy-5-chlorophenyl | 363 |
| 2-(7-fluoro) naphthyl | CH$_2$ | 4-Cl-1,2-Ph | CH=CH | 2-trifluoro methoxy-5-chlorophenyl | 364 |
| 2-(7-fluoro) | CH$_2$ | 6-Cl-1,2-Ph | CH=CH | 2-trifluoro | 365 |

TABLE I-continued $$\text{R}^1\text{R}^2\text{R}^3\text{-HET} - \underset{\underset{\text{X}-\text{B}}{|}}{\text{A}} - \underset{\text{O}}{\overset{\text{O}}{\|}} - \text{NHSO}_2\text{R}^{19}$$ Ia (Compounds 1–323 and 347–454)

| R¹R²R³-Het | A | X | B | R¹⁹ | Cpd |
|---|---|---|---|---|---|
| naphthyl | | | | methoxy-5-chlorophenyl | |
| 2-(7-fluoro) naphthyl | CH₂ | 4-Cl-1,2-Ph | 1,2-c-Pr | 2-trifluoro methoxy-5-chlorophenyl | 366 |
| 2-(7-fluoro) naphthyl | CH₂ | 3-Cl-1,2-Ph | CH=CH | 2-trifluoro methoxy-5-chlorophenyl | 367 |
| 2-(7-fluoro) naphthyl | SO₂ | 4-Cl-1,2-Ph | CH=CH | 2-thienyl | 368 |
| 2-(7-fluoro) naphthyl | O | 4-Cl-1,2-Ph | CH=CH | 2-thienyl | 369 |
| 2-(7-fluoro) naphthyl | S | 4-Cl-1,2-Ph | CH=CH | 2-thienyl | 370 |
| 2-(7-fluoro) naphthyl | CH₂ | 4-Cl-1,2-Ph | CH=CH | 2-thienyl | 371 |
| 2-(7-fluoro) naphthyl | CH₂ | 6-Cl-1,2-Ph | CH=CH | 2-thienyl | 372 |
| 2-(7-fluoro) naphthyl | CH₂ | 4-Cl-1,2-Ph | 1,2-c-Pr | 2-thienyl | 373 |
| 2-(7-fluoro) naphthyl | CH₂ | 3-Cl-1,2-Ph | CH=CH | 2-thienyl | 374 |
| 2-(7-fluoro) naphthyl | SO₂ | 4-Cl-1,2-Ph | CH=CH | 2-methoxy-5-bromophenyl | 375 |
| 2-(6-fluoro) naphthyl | O | 4-Cl-1,2-Ph | CH=CH | 2-methoxy-5-bromophenyl | 376 |
| 2-(6-fluoro) naphthyl | S | 4-Cl-1,2-Ph | CH=CH | 2-methoxy-5-bromophenyl | 377 |
| 2-(6-fluoro) naphthyl | CH₂ | 4-Cl-1,2-Ph | CH=CH | 2-methoxy-5-bromophenyl | 378 |
| 2-(6-fluoro) naphthyl | CH₂ | 6-Cl-1,2-Ph | CH=CH | 2-methoxy-5-bromophenyl | 379 |
| 2-(6-fluoro) naphthyl | CH₂ | 4-Cl-1,2-Ph | 1,2-c-Pr | 2-methoxy-5-bromophenyl | 380 |
| 2-(6-fluoro) naphthyl | CH₂ | 3-Cl-1,2-Ph | CH=CH | 2-methoxy-5-bromophenyl | 381 |
| 2-(7-chloro) naphthyl | SO₂ | 4-Cl-1,2-Ph | CH=CH | 2-thienyl | 382 |
| 2-(7-chloro) naphthyl | O | 4-Cl-1,2-Ph | CH=CH | 2-thienyl | 383 |
| 2-(7-chloro) naphthyl | S | 4-Cl-1,2-Ph | CH=CH | 2-thienyl | 384 |
| 2-(7-chloro) naphthyl | CH₂ | 4-Cl-1,2-Ph | CH=CH | 2-thienyl | 385 |
| 2-(7-chloro) naphthyl | CH₂ | 6-Cl-1,2-Ph | CH=CH | 2-thienyl | 386 |
| 2-(7-chloro) naphthyl | CH₂ | 4-Cl-1,2-Ph | 1,2-c-Pr | 2-thienyl | 387 |
| 2-(7-chloro) naphthyl | CH₂ | 3-Cl-1,2-Ph | CH=CH | 2-thienyl | 388 |
| 2-(6,7-difluoro) naphthyl | SO₂ | 4-Cl-1,2-Ph | CH=CH | 2-thienyl | 389 |
| 2-(6,7-difluoro) naphthyl | O | 4-Cl-1,2-Ph | CH=CH | 2-thienyl | 390 |
| 2-(6,7-difluoro) naphthyl | S | 4-Cl-1,2-Ph | CH=CH | 2-thienyl | 391 |
| 2-(6,7-difluoro) naphthyl | CH₂ | 4-Cl-1,2-Ph | CH=CH | 2-thienyl | 392 |
| 2-(6,7-difluoro) naphthyl | CH₂ | 6-Cl-1,2-Ph | CH=CH | 2-thienyl | 393 |
| 2-(6,7-difluoro) naphthyl | CH₂ | 4-Cl-1,2-Ph | 1,2-c-Pr | 2-thienyl | 394 |
| 2-(6,7-difluoro) naphthyl | CH₂ | 3-Cl-1,2-Ph | CH=CH | 2-thienyl | 395 |
| 2-(6,7-difluoro) naphthyl | SO₂ | 4-Cl-1,2-Ph | CH=CH | 2-methoxy-5-bromophenyl | 396 |
| 2-(6,7-difluoro) | O | 4-Cl-1,2-Ph | CH=CH | 2-methoxy-5- | 397 |

TABLE I-continued $$\text{R}^1\text{R}^2\text{R}^3\text{-HET} - \underset{\underset{X-B}{|}}{A} - \underset{\|}{\overset{O}{C}} - \text{NHSO}_2\text{R}^{19} \quad \text{Ia}$$

(Compounds 1–323 and 347–454)

| R¹R²R³-Het | A | X | B | R¹⁹ | Cpd |
|---|---|---|---|---|---|
| 2-(6,7-difluoro) naphthyl | S | 4-Cl-1,2-Ph | CH=CH | 2-methoxy-5-bromophenyl | 398 |
| 2-(6,7-difluoro) naphthyl | CH₂ | 4-Cl-1,2-Ph | CH=CH | 2-methoxy-5-bromophenyl | 399 |
| 2-(6,7-difluoro) naphthyl | CH₂ | 6-Cl-1,2-Ph | CH=CH | 2-methoxy-5-bromophenyl | 400 |
| 2-(6,7-difluoro) naphthyl | CH₂ | 4-Cl-1,2-Ph | 1,2-c-Pr | 2-methoxy-5-bromophenyl | 401 |
| 2-(6,7-difluoro) naphthyl | CH₂ | 3-Cl-1,2-Ph | CH=CH | 2-methoxy-5-bromophenyl | 402 |
| 2-(5,7-difluoro) naphthyl | CH₂ | 4-Cl-1,2-Ph | CH=CH | 2-methoxy-5-bromophenyl | 403 |
| 2-(5,7-difluoro) naphthyl | S | 4-Cl-1,2-Ph | CH=CH | 2-methoxy-5-bromophenyl | 404 |
| 2-(5,7-difluoro) naphthyl | O | 4-Cl-1,2-Ph | CH=CH | 2-methoxy-5-bromophenyl | 405 |
| 2-(5,7-difluoro) naphthyl | SO₂ | 4-Cl-1,2-Ph | CH=CH | 2-methoxy-5-bromophenyl | 406 |
| 2-(6-fluoro) quinolinyl | SO₂ | 4-Cl-1,2-Ph | CH=CH | 2-methoxy-5-bromophenyl | 407 |
| 2-(6-fluoro) quinolinyl | S | 4-Cl-1,2-Ph | CH=CH | 2-methoxy-5-bromophenyl | 408 |
| 2-(6-fluoro) quinolinyl | CH₂ | 4-Cl-1,2-Ph | CH=CH | 2-methoxy-5-bromophenyl | 409 |
| 2-(6-fluoro) quinolinyl | CH₂ | 1,2-Ph | CH=CH | 2-methoxy-5-bromophenyl | 410 |
| 2-(6-fluoro) quinolinyl | O | 4-Cl-1,2-Ph | CH=CH | 2-methoxy-5-bromophenyl | 411 |
| 2-(6-fluoro) quinolinyl | CH₂ | 4-Cl-1,2-Ph | 1,2-c-Pr | 2-methoxy-5-bromophenyl | 412 |
| 2-(5,7-difluoro)-quinolinyl | SO₂ | 4-Cl-1,2-Ph | CH=CH | 2-methoxy-5-bromophenyl | 413 |
| 2-(5,7-difluoro)-quinolinyl | S | 4-Cl-1,2-Ph | CH=CH | 2-methoxy-5-bromophenyl | 414 |
| 2-(5,7-difluoro)-quinolinyl | CH₂ | 4-Cl-1,2-Ph | CH=CH | 2-methoxy-5-bromophenyl | 415 |
| 2-(5,7-difluoro)-quinolinyl | CH₂ | 1,2-Ph | CH=CH | 2-methoxy-5-bromophenyl | 416 |
| 2-(5,7-difluoro)-quinolinyl | O | 4-Cl-1,2-Ph | CH=CH | 2-methoxy-5-bromophenyl | 417 |
| 2-(5,7-difluoro)-quinolinyl | CH₂ | 4-Cl-1,2-Ph | 1,2-c-Pr | 2-methoxy-5-bromophenyl | 418 |
| 3,4-dichloro phenyl | SO₂ | 4-Cl-1,2-Ph | CH=CH | 2-methoxy-5-bromophenyl | 419 |
| 3,4-dichloro phenyl | S | 4-Cl-1,2-Ph | CH=CH | 2-methoxy-5-bromophenyl | 420 |
| 3,4-dichloro phenyl | CH₂ | 4-Cl-1,2-Ph | CH=CH | 2-methoxy-5-bromophenyl | 421 |
| 3,4-dichloro phenyl | CH₂ | 1,2-Ph | CH=CH | 2-methoxy-5-bromophenyl | 422 |
| 3,4-dichloro phenyl | O | 4-Cl-1,2-Ph | CH=CH | 2-methoxy-5-bromophenyl | 423 |
| 3,4-dichloro phenyl | CH₂ | 4-Cl-1,2-Ph | 1,2-c-Pr | 2-methoxy-5-bromophenyl | 424 |
| 3,4-dichloro phenyl | CH₂ | 5-Cl-1,2-Ph | CH=CH | 2-methoxy-5-bromophenyl | 425 |
| 4-chloro phenyl | SO₂ | 4-Cl-1,2-Ph | CH=CH | 2-methoxy-5-bromophenyl | 426 |
| 4-chloro phenyl | S | 4-Cl-1,2-Ph | CH=CH | 2-methoxy-5-bromophenyl | 427 |
| 4-chloro phenyl | CH₂ | 4-Cl-1,2-Ph | CH=CH | 2-methoxy-5-bromophenyl | 428 |
| 4-chloro phenyl | CH₂ | 1,2-Ph | CH=CH | 2-methoxy-5-bromophenyl | 429 |
| 4-chloro phenyl | O | 4-Cl-1,2-Ph | CH=CH | 2-methoxy-5-bromophenyl | 430 |

TABLE I-continued

Ia

R¹R²R³-HET-A-X-B-C(=O)-NHSO₂R¹⁹

(Compounds 1–323 and 347–454)

| R¹R²R³-Het | A | X | B | R¹⁹ | Cpd |
|---|---|---|---|---|---|
| 4-chloro phenyl | CH₂ | 4-Cl-1,2-Ph | 1,2-c-Pr | 2-methoxy-5-bromophenyl | 431 |
| 4-chloro phenyl | CH₂ | 4-Cl-1,2-Ph | CH=CH | 2-methoxy-5-bromophenyl | 432 |
| 3,4-dichloro phenyl | SO₂ | 4-Cl-1,2-Ph | CH=CH | 2-thienyl | 433 |
| 3,4-dichloro phenyl | S | 4-Cl-1,2-Ph | CH=CH | 2-thienyl | 434 |
| 3,4-dichloro phenyl | CH₂ | 4-Cl-1,2-Ph | CH=CH | 2-thienyl | 435 |
| 3,4-dichloro phenyl | CH₂ | 1,2-Ph | CH=CH | 2-thienyl | 436 |
| 3,4-dichloro phenyl | O | 4-Cl-1,2-Ph | CH=CH | 2-thienyl | 437 |
| 3,4-dichloro phenyl | CH₂ | 4-Cl-1,2-Ph | CH=CH | 2-thienyl | 438 |
| 3,4-dichloro phenyl | CH₂ | 5-Cl-1,2-Ph | CH=CH | 2-thienyl | 439 |
| 4-chloro phenyl | SO₂ | 4-Cl-1,2-Ph | CH=CH | 2-thienyl | 440 |
| 4-chloro phenyl | S | 4-Cl-1,2-Ph | CH=CH | 2-thienyl | 441 |
| 4-chloro phenyl | CH₂ | 4-Cl-1,2-Ph | CH=CH | 2-thienyl | 442 |
| 4-chloro phenyl | CH₂ | 1,2-Ph | CH=CH | 2-thienyl | 443 |
| 1-(5-chloro)indolyl | CH₂ | 3,2-Pyr | CH=CH | 2,4-(Me)₂-thiazol-5-yl | 444 |
| 1-(5-chloro)indolyl | CH₂ | 3,2-Pyr | CH=CH | 2-thienyl | 445 |
| 1-(6-(4-chloro)phenyl)indolyl | CH₂ | 4-F-1,2-Ph | CH=CH | 3-chloro-4-fluorophenyl | 446 |
| 2-(6-difluoro methoxy)naphthyl | CH₂ | 4-Cl-1,2-Ph | CH=CH | 2-methoxy-5-bromophenyl | 447 |
| 2-naphthyl | CH₂ | 4-MeO-1,2-Ph | CH=CH | 2-methoxy-5-bromophenyl | 448 |
| 2-naphthyl | CH₂ | 5-Cl-1,2-Ph | CH=CH | 2-methoxy-5-bromophenyl | 449 |
| 2-(6-chloro naphthyl) | CH₂ | 4-Cl-1,2-Ph | CH=CH | 2-methoxy-5-bromophenyl | 450 |
| 1-(5-phenyl methoxy)indolyl | CH₂ | 4-F-1,2-Ph | CH=CH | 2-methoxy-5-bromophenyl | 451 |
| 2-(benzo[b]thiophenyl) | CH₂ | 4-F-1,2-Ph | CH=CH | 2-methoxy-5-bromophenyl | 452 |
| 5-(1-benzyl)indolyl | CH₂ | 4-F-1,2-Ph | CH=CH | 2-methoxy-5-bromophenyl | 453 |
| 1-(6-(4-chloro)phenyl)indolyl | CH₂ | 4-F-1,2-Ph | CH=CH | 2-methoxy-5-bromophenyl | 454 |

TABLE II

I-b

R¹R²R³—HET-A-X-B-C(=O)-OH (Compounds 324–346 and 455–542)

| R¹R²R³—Het | A | X | B | Cpd |
|---|---|---|---|---|
| 2-naphthyl | S(O)₂ | 1,2-phenyl | CH=CH | 324 |
| 2-naphthyl | S | 1,2-phenyl | CH=CH | 325 |

TABLE II-continued

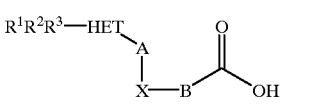

(Compounds 324–346 and 455–542)

| R¹R²R³—Het | A | X | B | Cpd |
|---|---|---|---|---|
| 4-methylthiophenyl | $CH_2$ | 1,2-phenyl | CH=CH | 326 |
| 3-methylindol-1-yl | $CH_2$ | 1,2-phenyl | CH=CH | 327 |
| 3-chloro-4-fluorophenyl | $CH_2$ | 1,2-phenyl | CH=CH | 328 |
| 4-chlorophenyl | $CH_2$ | 1,2-phenyl | CH=CH | 329 |
| 2-naphthyl | $CH_2$ | 1,2-phenyl | CH=CH | 330 |
| 2-naphthyl | $S(O)_2$ | 1,2-phenyl | 1,2-c-propyl | 331 |
| 2-naphthyl | $S(O)_2$ | 1,2-phenyl | $CH_2$—$CH_2$ | 332 |
| 2-naphthyl | S | 1,2-phenyl | CH=CH | 333 |
| 3,4-dichlorophenyl | $S(O)_2$ | 1,2-phenyl | $CH_2$—$CH_2$ | 334 |
| 3,4-dichlorophenyl | $CH_2$ | 1,2-phenyl | CH=CH | 335 |
| 2-(6-benzyloxy)naphthyl | $CH_2$ | 1,2-phenyl | CH=CH | 336 |
| 2-(6-benzyloxy)naphthyl | $CH_2$ | 1,2-phenyl | 1,2-c-propyl | 337 |
| 2-(6-benzyloxy)naphthyl | $SO_2$ | 1,2-phenyl | 1,2-c-propyl | 338 |
| 2-(6-benzyloxy)naphthyl | $CH_2$—O | 1,2-phenyl | 1,2-c-propyl | 339 |
| 2-(6-benzyloxy)naphthyl | O—$CH_2$ | 1,2-phenyl | 1,2-c-propyl | 340 |
| 2-(6-benzyloxy)naphthyl | $SO_2$ | 1,2-phenyl | CH=CH | 341 |
| 2-(6-benzyloxy)naphthyl | $CH_2$—O | 1,2-phenyl | CH=CH | 342 |
| 2-(6-benzyloxy)naphthyl | O—$CH_2$ | 1,2-phenyl | CH=CH | 343 |
| 2-(6-benzyloxy)naphthyl | S | 1,2-phenyl | CH=CH | 344 |
| 2-(7-benzyloxy)naphthyl | $SO_2$ | 1,2-phenyl | CH=CH | 345 |
| 2-(6-(4-trifluoromethyl)benzyloxy))naphthyl | $CH_2$ | 1,2-phenyl | CH=CH | 346 |
| 2-(6-fluoro)naphthyl | $SO_2$ | 4-Cl-1,2-Ph | CH=CH | 455 |
| 2-(6-fluoro)naphthyl | S | 4-Cl-1,2-Ph | CH=CH | 456 |
| 2-(6-fluoro)naphthyl | $CH_2$ | 4-Cl-1,2-Ph | CH=CH | 457 |
| 2-(6-fluoro)naphthyl | $CH_2$ | 1,2-Ph | CH=CH | 458 |
| 2-(6-fluoro)naphthyl | O | 4-Cl-1,2-Ph | CH=CH | 459 |
| 2-(6-fluoro)naphthyl | $CH_2$ | 4-Cl-1,2-Ph | 1,2-c-Pr | 460 |
| 2-(7-fluoro)naphthyl | $SO_2$ | 4-Cl-1,2-Ph | CH=CH | 461 |
| 2-(7-fluoro)naphthyl | S | 4-Cl-1,2-Ph | CH=CH | 462 |
| 2-(7-fluoro)naphthyl | $CH_2$ | 4-Cl-1,2-Ph | CH=CH | 463 |
| 2-(7-fluoro)naphthyl | $CH_2$ | 1,2--Ph | CH=CH | 464 |
| 2-(7-fluoro)naphthyl | O | 4-Cl-1,2-Ph | CH=CH | 465 |
| 2-(7-fluoro)naphthyl | $CH_2$ | 4-Cl-1,2-Ph | 1,2-c-Pr | 466 |
| 2-(6-chloro)naphthyl | $SO_2$ | 4-Cl-1,2-Ph | CH=CH | 467 |
| 2-(6-chloro)naphthyl | S | 4-Cl-1,2-Ph | CH=CH | 468 |
| 2-(6-chloro)naphthyl | $CH_2$ | 4-Cl-1,2-Ph | CH=CH | 469 |
| 2-(6-chloro)naphthyl | $CH_2$ | 1,2-Ph | CH=CH | 470 |
| 2-(6-chloro)naphthyl | O | 4-Cl-1,2-Ph | CH=CH | 471 |
| 2-(6-chloro)naphthyl | $CH_2$ | 4-Cl-1,2-Ph | 1,2-c-Pr | 472 |
| 2-(7-chloro)naphthyl | $SO_2$ | 4-Cl-1,2-Ph | CH=CH | 473 |
| 2-(7-chloro)naphthyl | S | 4-Cl-1,2-Ph | CH=CH | 474 |
| 2-(7-chloro)naphthyl | $CH_2$ | 4-Cl-1,2-Ph | CH=CH | 475 |
| 2-(7-chloro)naphthyl | $CH_2$ | 4-Cl-1,2-Ph | CH=CH | 476 |
| 2-(7-chloro)naphthyl | $CH_2$ | 4-Cl-1,2-Ph | CH=CH | 477 |
| 2-(7-chloro)naphthyl | $CH_2$ | 4-Cl-1,2-Ph | CH=CH | 478 |
| 2-(6,7-difluoro)naphthyl | $SO_2$ | 4-Cl-1,2-Ph | CH=CH | 479 |
| 2-(6,7-difluoro)naphthyl | S | 4-Cl-1,2-Ph | CH=CH | 480 |
| 2-(6,7-difluoro)naphthyl | $CH_2$ | 4-Cl-1,2-Ph | CH=CH | 481 |
| 2-(6,7-difluoro)naphthyl | $CH_2$ | 4-Cl-1,2-Ph | CH=CH | 482 |
| 2-(6,7-difluoro)naphthyl | $CH_2$ | 4-Cl-1,2-Ph | CH=CH | 483 |
| 2-(6,7-difluoro)naphthyl | $CH_2$ | 4-Cl-1,2-Ph | 1,2-c-Pr | 484 |
| 2-(6,7-difluoro)naphthyl | $CH_2$ | 4-Cl-1,2-Ph | CH=CH | 485 |
| 2-(6,7-difluoro)naphthyl | $CH_2$ | 4-Cl-1,2-Ph | CH=CH | 486 |
| 2-(6,7-difluoro)naphthyl | $CH_2$ | 4-Cl-1,2-Ph | CH=CH | 487 |
| 2-(6,7-difluoro)naphthyl | $CH_2$ | 1,2-Ph | CH=CH | 488 |
| 2-(6,7-difluoro)naphthyl | $CH_2$ | 4-Cl-1,2-Ph | CH=CH | 489 |
| 2-(6,7-difluoro)naphthyl | $CH_2$ | 4-Cl-1,2-Ph | 1,2-c-Pr | 490 |
| 3-methyl-5-fluoro indol-1-yl | $SO_2$ | 4-Cl-1,2-Ph | CH=CH | 491 |
| 3-methyl-5-fluoro indol-1-yl | S | 4-Cl-1,2-Ph | CH=CH | 492 |
| 3-methyl-5-fluoro indol-1-yl | $CH_2$ | 4-Cl-1,2-Ph | CH=CH | 493 |
| 3-methyl-5-fluoro indol-1-yl | $CH_2$ | 1,2-Ph | CH=CH | 494 |
| 3-methyl-5-fluoro indol-1-yl | $CH_2$ | 4-Cl-1,2-Ph | CH=CH | 495 |
| 3-methyl-5-fluoro | $CH_2$ | 4-Cl-1,2-Ph | CH=CH | 496 |

TABLE II-continued $$R^1R^2R^3-HET-\underset{X-B}{\overset{A}{|}}-\underset{OH}{\overset{O}{\|}}$$

I-b (Compounds 324–346 and 455–542)

| $R^1R^2R^3$—Het | A | X | B | Cpd |
|---|---|---|---|---|
| indol-1-yl | | | | |
| 2-(6-fluoro)quinolinyl | $SO_2$ | 4-Cl-1,2-Ph | CH=CH | 497 |
| 2-(6-fluoro)quinolinyl | S | 4-Cl-1,2-Ph | CH=CH | 498 |
| 2-(6-fluoro)quinolinyl | $CH_2$ | 4-Cl-1,2-Ph | CH=CH | 499 |
| 2-(6-fluoro)quinolinyl | $CH_2$ | 4-Cl-1,2-Ph | CH=CH | 500 |
| 2-(6-fluoro)quinolinyl | O | 4-Cl-1,2-Ph | CH=CH | 501 |
| 2-(6-fluoro)quinolinyl | $CH_2$ | 4-Cl-1,2-Ph | CH=CH | 502 |
| 2-(6-difluoromethoxy)-naphthyl | $SO_2$ | 4-Cl-1,2-Ph | CH=CH | 503 |
| 2-(6-difluoromethoxy)-naphthyl | $SO_2$ | 4-Cl-1,2-Ph | CH=CH | 504 |
| 2-(6-difluoromethoxy)-naphthyl | $SO_2$ | 4-Cl-1,2-Ph | CH=CH | 505 |
| 2-(6-difluoromethoxy)-naphthyl | $SO_2$ | 4-Cl-1,2-Ph | CH=CH | 506 |
| 2-(6-difluoromethoxy)-naphthyl | $SO_2$ | 4-Cl-1,2-Ph | CH=CH | 507 |
| 2-(6-difluoromethoxy)-naphthyl | $SO_2$ | 4-Cl-1,2-Ph | CH=CH | 508 |
| 2-(7-difluoromethoxy)-naphthyl | $SO_2$ | 4-Cl-1,2-Ph | CH=CH | 509 |
| 2-(7-difluoromethoxy)-naphthyl | S | 4-Cl-1,2-Ph | CH=CH | 510 |
| 2-(7-difluoromethoxy)-naphthyl | $CH_2$ | 4-Cl-1,2-Ph | CH=CH | 511 |
| 2-(7-difluoromethoxy)-naphthyl | $CH_2$ | 4-Cl-1,2-Ph | CH=CH | 512 |
| 2-(7-difluoromethoxy)-aphthyl | O | 4-Cl-1,2-Ph | CH=CH | 513 |
| 2-(7-difluoromethoxy)-naphthyl | $CH_2$ | 4-Cl-1,2-Ph | CH=CH | 514 |
| 2-(6-methoxy)naphthyl | $SO_2$ | 4-Cl-1,2-Ph | CH=CH | 515 |
| 2-(6-methoxy)naphthyl | S | 4-Cl-1,2-Ph | CH=CH | 516 |
| 2-(6-methoxy)naphthyl | $CH_2$ | 4-Cl-1,2-Ph | CH=CH | 517 |
| 2-(6-methoxy)naphthyl | $CH_2$ | 4-Cl-1,2-Ph | CH=CH | 518 |
| 2-(6-methoxy)naphthyl | O | 4-Cl-1,2-Ph | CH=CH | 519 |
| 2-(6-methoxy)naphthyl | $CH_2$ | 4-Cl-1,2-Ph | CH=CH | 520 |
| 2-(6-fluoro)naphthyl | $CH_2$ | 4-Cl-1,2-Ph | CH=CH | 521 |
| 2-(6-fluoro)naphthyl | $CH_2$ | 4-Cl-1,2-Ph | CH=CH | 522 |
| 2-(6-fluoro)naphthyl | $CH_2$ | 4-Cl-1,2-Ph | CH=CH | 523 |
| 2-(6-fluoro)naphthyl | $CH_2$ | 4-Cl-1,2-Ph | CH=CH | 524 |
| 2-(6-fluoro)naphthyl | $CH_2$ | 4-Cl-1,2-Ph | CH=CH | 525 |
| 2-(6-fluoro)naphthyl | $CH_2$ | 4-Cl-1,2-Ph | CH=CH | 526 |
| 2-(7-fluoro)naphthyl | $CH_2$ | 4-Cl-1,2-Ph | CH=CH | 527 |
| 2-(7-fluoro)naphthyl | $CH_2$ | 4-Cl-1,2-Ph | CH=CH | 528 |
| 2-(7-fluoro)naphthyl | $CH_2$ | 4-Cl-1,2-Ph | CH=CH | 529 |
| 2-(7-fluoro)naphthyl | $CH_2$ | 4-Cl-1,2-Ph | CH=CH | 530 |
| 2-(7-fluoro)naphthyl | $CH_2$ | 4-Cl-1,2-Ph | CH=CH | 531 |
| 2-(7-fluoro)naphthyl | $CH_2$ | 4-Cl-1,2-Ph | CH=CH | 532 |
| 2-naphthyl | $CH_2$ | 4,5-$Cl_2$-1,2-Ph | CH=CH | 533 |
| 2-naphthyl | $CH_2$ | 4-Cl-1,2-Ph | CH=CH | 534 |
| 3,4-dichlorophenyl | $CH_2$ | 4-Cl-1,2-Ph | CH=CH | 535 |
| 2-naphthyl | $CH_2$ | 4-Cl-1,2-Ph | CH=CH | 536 |
| 4-chlorophenyl | $CH_2$ | 4-Cl-1,2-Ph | CH=CH | 537 |
| 1-(5-phenylmethoxy)indolyl | $CH_2$ | 4-F-1,2-Ph | CH=CH | 538 |
| 2-(benzo[b]thiophenyl) | $CH_2$ | 4-F-1,2-Ph | CH=CH | 539 |
| 5-(1-benzyl)indolyl | $CH_2$ | 4-F-1,2-Ph | CH=CH | 540 |
| 1-(6-(4-chloro)phenyl)indolyl | $CH_2$ | 4-F-1,2-Ph | CH=CH | 541 |
| 1-(5-chloro)indolyl | $CH_2$ | 3,2-Pyr | CH=CH | 542 |

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that in the discussion of methods of treatment which follows, references to the compounds of Formula I are meant to also include the pharmaceutically acceptable salts.

The magnitude of prophylactic or therapeutic dose of a compound of Formula I will, of course, vary with the nature and the severity of the condition to be treated and with the particular compound of Formula I and its route of administration. It will also vary according to a variety of factors including the age, weight, general health, sex, diet, time of administration, rate of excretion, drug combination and response of the individual patient. In general, the daily dose from about 0.001 mg to about 100 mg per kg body weight of a mammal, preferably 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for oral administration to humans may contain from about 0.5 mg to about 5 g of active agent compounded with an appropriate and convenient amount of carrier material which may vary from about 5 to about 95 percent of the total composition. Dosage unit forms will generally contain from about 1 mg to about 2 g of an active ingredient, typically 25 mg, 50 mg, 100 mg, 200 mg, 300 mg, 400 mg, 500 mg, 600 mg, 800 mg, or 1000 mg.

For the treatment of any of the prostanoid mediated diseases compound I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, solutions, aqueous or oily suspensions, dispersible powders or granules, emulsions, hard or soft capsules, syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compound I may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing the compound of Formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

The ability of the compounds of Formula I to interact with prostaglandin receptors makes them useful for treating, preventing or reversing undesirable symptoms caused by prostaglandins in a mammalian, especially human subject. This mimicking or antagonism of the actions of prostaglandins indicates that the compounds and pharmaceutical compositions thereof are useful to treat, prevent or ameliorate prostaglandin mediated diseases and conditions in mammals and especially in humans: Pain, fever and inflammation of a variety of conditions including rheumatic fever, symptoms associated with influenza or other viral infections, common cold, low back and neck pain, skeletal pain, postpartum pain, dysmenorrhea, headache, migraine, toothache, sprains and strains, myositis, neuralgia, synovitis, arthritis, including rheumatoid arthritis, degenerative joint diseases (osteoarthritis), gout and ankylosing spondylitis, bursitis, burns including radiation and corrosive chemical injuries, sunburns, pain following surgical and dental procedures as well as immune and autoimmune diseases. In addition, such a compound may inhibit cellular neoplastic transformations and metastic tumor growth and hence can be used in the treatment of cancer. Compound I may also be of use in the treatment and/or prevention prostaglandin-mediated proliferation disorders such as may occur in diabetic retinopathy and tumor angiogenesis. Compound I will also inhibit prostanoid-induced smooth muscle contraction by antagonizing contractile prostanoids or mimicking relaxing prostanoids and hence may be use in the treatment of dysmenorrhea, premature labor, asthma and eosinophil related disorders. It will also be of use in the treatment of Alzheimer's disease, the treatment of glaucoma, for the prevention of bone loss (treatment of osteoporosis) and for the promotion of bone formation (treatment of fractures) and other bone diseases such as Paget's disease.

By virtue of its prostanoid or prostanoid antagonist activity, compound I will prove useful as an alternative to NSAID'S particularly where such non-steroidal anti-inflammatory drugs may be contraindicated such as in patients with peptic ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems; kidney disease; thrombosis, occlusive vascular diseases; those prior to surgery or taking anti-coagulants. Compound I will also be useful as a cytoprotective agent for patients under chemotherapy.

Compound of Formula I, will be useful as a partial or complete substitute for conventional antiinflammatory or analgesic compounds in preparations wherein they are presently co-administered with other agents or ingredients. Thus in further aspects, the invention encompasses pharmaceutical compositions for treating prostaglandin $E_2$ mediated diseases as defined above comprising a non-toxic therapeutically effective amount of the compound of Formula I as defined above and one or more ingredients such as another pain reliever including acetaminophen or phenacetin; a COX-2 selective NSAID; a conventional NSAID; a potentiator including caffeine; an $H_2$-antagonist, aluminum or magnesium hydroxide, simethicone, a decongestant including phenylephrine, phenylpropanolamine, pseudophedrine, oxymetazoline, ephinephrine, naphazoline, xylometazoline, propylhexedrine, or levo-desoxyephedrine; an antiitussive including codeine, hydrocodone, caramiphen, carbetapentane, or dextramethorphan; another prostaglandin ligand including misoprostol, enprostil, rioprostil, ornoprostol or rosaprostol; a diuretic; a sedating or non-sedating antihistamine. In addition, the invention encompasses a method of treating prostaglandin $E_2$ mediated diseases comprising: administration to a patient in need of such treatment a non-toxic therapeutically effective amount of the compound of Formula I, optionally co-administered with one or more of such ingredients as listed immediately above.

Compounds of the present invention can be prepared according to the following methods. Temperatures are in degrees Celsius.

Boronic acids and esters can be prepared from the corresponding halide according to literature procedure and reference cited therein (Charette, A. B.; Giroux, A. J. Org. Chem. 1996, 61, 8718; Ishiyama, T.; Murata, M.; Miyaura, N. J. Org. Chem. 1995, 60, 7508; Miyaura, N.; Suzuki, A. Chem. Rev, 1995, 95, 2457; Murata, M.; Watanabe, S.; Masuda, Y. J. Org. Chem. 1997, 62, 6458; Watanabe, T. Miyaura, N.; Suzuki, A. Synlett, 1992, 207; Maddaford, S.; Keay, B. A. J. Org. Chem. 1994, 59, 6501; Cristofoli, W. A.; Keay, B. A. Tetrahedron Lett. 1991, 32, 5881; Passafaro, M. S.; Keay, B. A. . Tetrahedron Lett. 1996, 37, 429; Serafin, B.; Makosza, M. Tetrahedron, 1963, 19, 821). In some cases, the triflate, the tin or the zinc derivatives may be used instead of the boronic acid.

Method A

Cinnamic ester 1 is treated with a brominating agent such as NBS in a refluxing inert solvent such as $CCl_4$, with the use of an initiator like benzoyl peroxide or light. The resulting benzylic bromide is reacted in a Suzuki coupling reaction with the appropriate boronic acid or ester, a catalyst such as tetrakis(triphenylphosphine) palladium and cesium fluoride or $Na_2CO_3$ or a base in an inert refluxing solvent such as DME at 80–90° C. The new cinnamic ester 3 is hydrolyzed with aqueous sodium hydroxide to afford the acid 4 that is converted to the cinnamic sulfonamide 5 with a coupling reagent such as DCC or DCI in $CH_2Cl_2$ at r.t.

Method B

Cinnamic ester 2 is treated with an aryl or heteroaryl mercaptan, alcohol or amine, and with a base such as a hydride or an amine in benzene or THF at 0–23° C. The resulting cinnamic ester 6 is converted to 7 according to Method A.

If W=sulfur, it is oxidized to the sulfoxide or sulfone 8 with hydrogen peroxide, m-CPBA or other peracetic acid. The cinnamic ester 8 is converted to 9 according to Method A.

Method C

The aldehyde 11 is prepared by an addition-elimination of a mercapto, hydroxy or amino aryl or heteroaryl with a base such as $K_2CO_3$ in refluxing $CHCl_3$. If needed a higher boiling point solvent can be used. This type of rection can also be performed with CuO in DMF. An Emmons-Horner type reaction (or Wittig) in toluene at r.t. followed by Method A (or oxidation as described in Method B) results in the cinnamic sulfonamide 13.

Method D

Acetal 14 that came from an acetalization from a suitably substituted bromo benzaldehyde is converted to the Grignard reagent with magnesium in an etheral solvent at reflux and quenched with an aryl or heteroaryl ketone. The alcohol 16 is reacted with an halide and a base (or protected as the o-nitrobenzyl, and removed at the end of the sequence) to furnish the compound 17. Deprotection of the acetal under standard conditions followed by Method C gives 18.

Method E

Alcohol 16 is converted to an acetate with acetyl chloride (or acetic anhydride and an amine base) and coupled with a Grignard reagent and a copper salt at low temperature. The alcohol 16 could also be converted to the bromide and treated in a similar way to yield 20. Alternatively the tetrametyl acetal (R=methyl) version of alcohol 16 can be treated with $TiCl_4/Me_2Zn$ (or $R^7_2Zn$) at –30° C. Compound 20 is then converted to the cinnamic sulfonamide 21 according to Method D. Also, 22 can be treated with $Al(R^7)_8$ in toluene at 80° C. for 24 h and 23 converted to the aldehyde with n-BuLi/DMF followed by an Emmons-Horner reaction and Method A to yield compound 21.

Method F

A suitably substituted bromo toluene 24 is treated with n-Buli at low temperature and quenched with an aryl or heteroaryl aldehyde. The resulting alcohol is oxidized to the ketone with PDC, PCC, $MnO_2$ or other typical oxidizing agent. The carbonyl is treated with $SF_4$, $MoF_6$-$BF_3$ (or converted to a thioacetal and treated with nitrosonium $BF_4$-pyridinium.HF) to yield the difluoride. Benzylic bromination with NBS followed by oxidation with N-methylmorpholine N-oxide at 100° C. in dioxane for 4 h, yielded compound 25 that is converted to cinnamic sulfonamide 26 with Method C.

Method G

The appropriately substituted methyl bromo(or triflate) benzoate 27 is converted to compound 28 by a Suzuki coupling reaction followed by hydrogenation. A Stille coupling reaction could also be used. Benzylic bromination or benzylic oxidation followed by treatment with a brominating agent such as $CBr_4$/triphenylphosphine gives compound 29 which can be treated with a boronic acid, or a tin compound (Stille) to furnish compound 30. Reduction of the ester with DIBAL, oxidation with $MnO_2$ and Method C gives compound 31.

Method H

Compound 29 (one $R^7$=H) is treated with triphenyl phosphine to give the salt and, with a base such as LDA, is converted to compound 32 with the aryl or heteroaryl ketone. The halide 29 can also be converted the Grignard reagent and added to the ketone. Dehydration under acidic conditions results in compound 32. Reduction of the double bond under standard conditions, followed by Methods G and C gives compound 33. From compound 32, cyclopropanation with diazomethane and palladium (0) followed by Methods G, C and A gives compound 34.

Method I

The (heterocyclic) vinylic bromide 35 is reacted in a Suzuki coupling reaction with an aryl or hetero aryl boronic acid and converted to a new borane by 9-BBN addition followed by a second Suzuki reaction with compound 14. Compound 37 thus formed is reduced by hydrogenolysis ($H_2$/metal or diimide) and deprotection followed by Method C gives cinnamic sulfonamide 39.

Method J

Ketone 40 which comes from oxidation of the corresponding alcohol is reacted with a phosphonium salt or phosphono ester with a base such as LDA to give the cinnamic ester 41. Method A yields 42 and reduction of the double bond by the previously mentioned method gives the acyl sulfonamide 43.

Method K

Cinnamic ester 3 is reduced to 44 by the previously mentioned method. αAlkylation with a base such as LDA followed by an alkylating agent results in 45 after conversion to the acyl sulfonamide.

Method L

Cinnamic ester 3 is reduced to 46 with DIBAL and the double bond converted to a cyclopropane by a Simmons-Smith reaction, or similar reactions recently described in the literature. Compound 47 is then oxidized and the cinnamic sulfonamide 48 is prepared according to Method A.

Method M

Ester 49 which can come from the homologation of the appropriately substituted methyl ortho-toluate, is treated with a base and with an alkylating agent to furnish compound 50. Benzylic bromination and Suzuki coupling gives an intermediate ester. Homologation according to *J. Amer. Chem. Soc.;* 1985, 1429; *J. Org. Chem.* 1992, 7194, followed by alkylation with a base such as LDA and an alkylating agent furnishes acylsulfonamide 51 by Method A.

Compound 50 can also be converted to the benzylic bromide and to compound 52 by Method A.

Method N

Suitably substituted compound 53 is treated with a boronic acid to give compound 54 which is reduced with LDA to the alcohol 55. Treatment with phosgene followed with the appropriate sulfonamide gives compound 56. This can also be prepared by mixing phosgene and the sulfonamide at 140° C. to generate the isocyanate.

Compound 54 is treated with a Grignard reagent to give the corresponding alcohol and as previously described, converted to compound 57.

Method O

Ester 58 is treated with Lawesson's reagent, DAST and light to give the benzylic alcohol 59. The procedure according to Method N yields compound 60.

Method P

Compound 59 is brominated as described earlier (or iodinated) and reacted in a $SN^2$ type reaction with an ester and a base such as LDA to furnish ester 61. Method A gives the acylsulfonamide 62.

Method Q

Compound 55 is treated with $NH_3/Ph_3P/DEAD$ (or treated with $CBr_4/Ph_3P$ and the bromide converted to the amine 63 with ammonia). Treatment with phosgene followed by sulfonamide yields 64, treatment of which with a base and an alkyl or benzylic halide gives compounds 65.

Method R

Aldehyde 10 is treated with a silylated source of hydroxyl or thiol at 80–130° C., and the silyl group removed by fluoride treatment. Compound 66 is then treated with an aryl or heteroaryl methylene bromide with a base such as a tertiary amine in $CHCl_3$ or benzene to yield aldehyde 67. Emmons-Horner (or Wittig reaction) with LDA results in compound 68 via Method A.

Method S

In the case of an amine an alternative to method R can be used. A suitably substituted nitro aldehyde 69 is converted to compound 70 as described earlier and the nitro group reduced with standard methods. Mono-alkylation followed by displacement with an aryl or heteroaryl methylene bromide and processing by Method A yields cinnamic sulfonamide 71.

Method T

A suitably substituted bromo toluene 24 is converted to the anion in an etheral solvent at low temperature and trapped with an aldehyde of an aryl or heteroaryl. The resulting alcohol is oxidized with $MnO_2$, Jones' reagent, PDC, PCC or any other oxidant. Benzylic bromination followed by oxidation with N-methyl morpholine N-oxide, yields a ketoaldehyde. Emmons-Horner and Method A gives the cinnamic sulfonamides 72.

Generic structures 4, 5, 7, 9, 13, 18, 21, 26, 31, 33, 34, 39, 42, 43, 45, 48, 51, 52, 56, 57, 60, 62, 64, 65, 68, 71 and 72 are representative of the compounds of the present invention. It is also noted that where the chemistry allows in the generic schemes, alternate embodiments of -A-, such as heteroaryl groups, can be substituted for phenyl in the schemes.

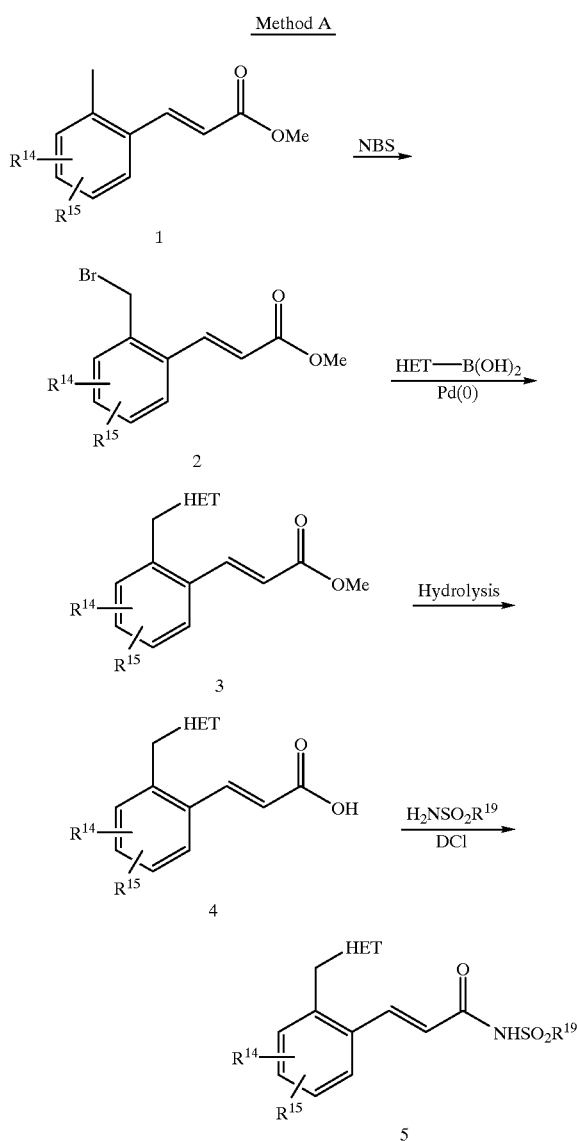

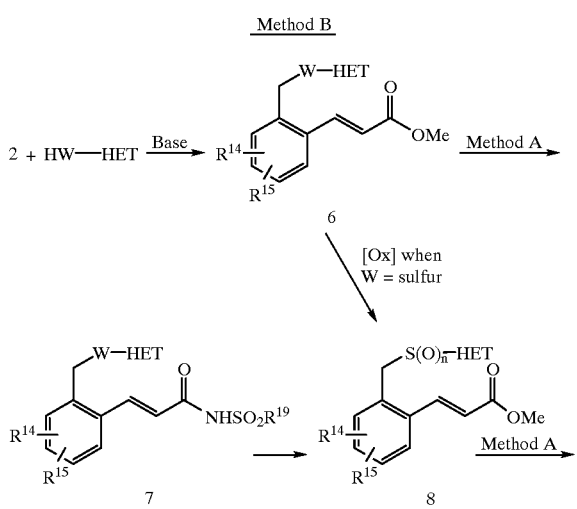

-continued
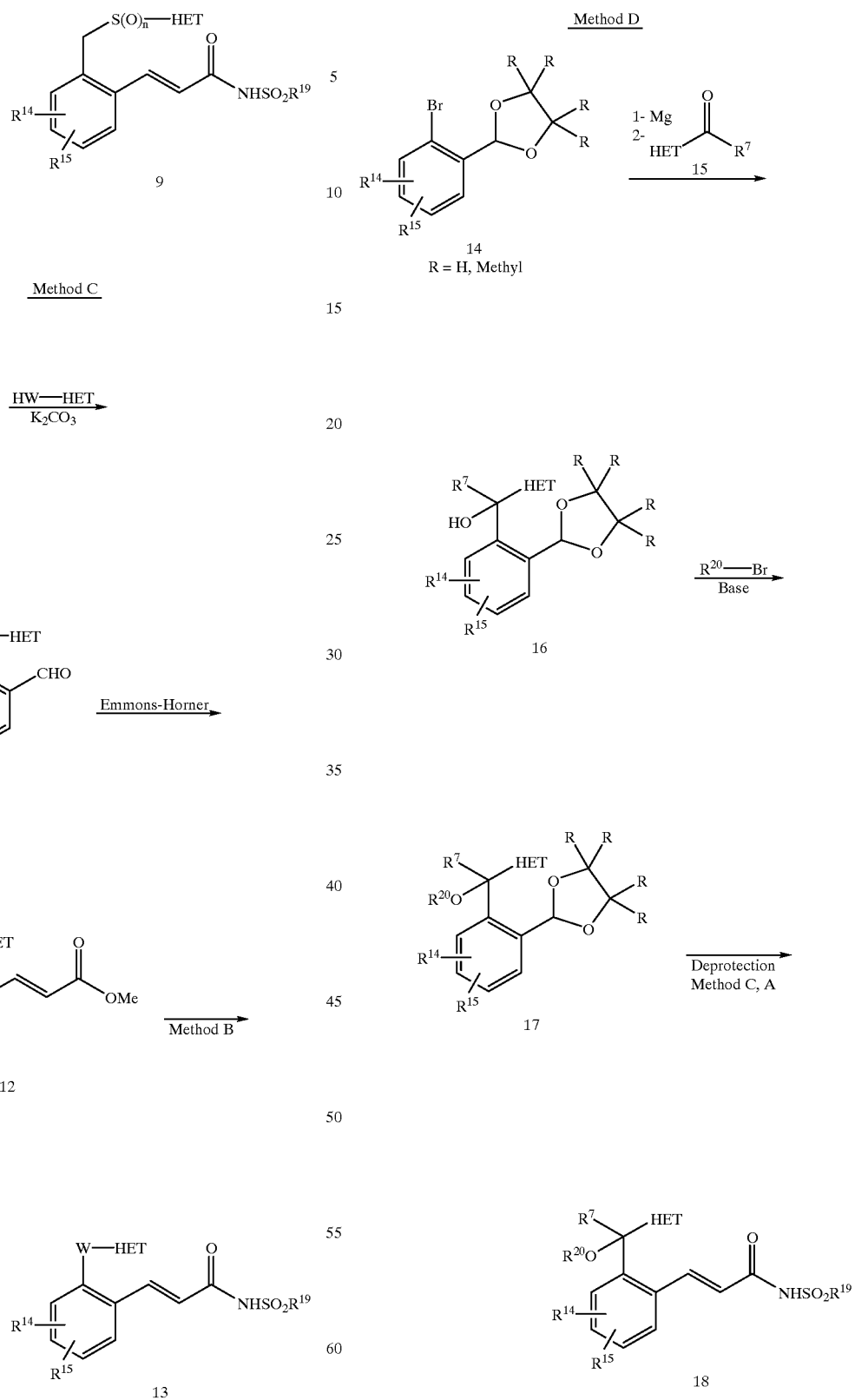

Method E
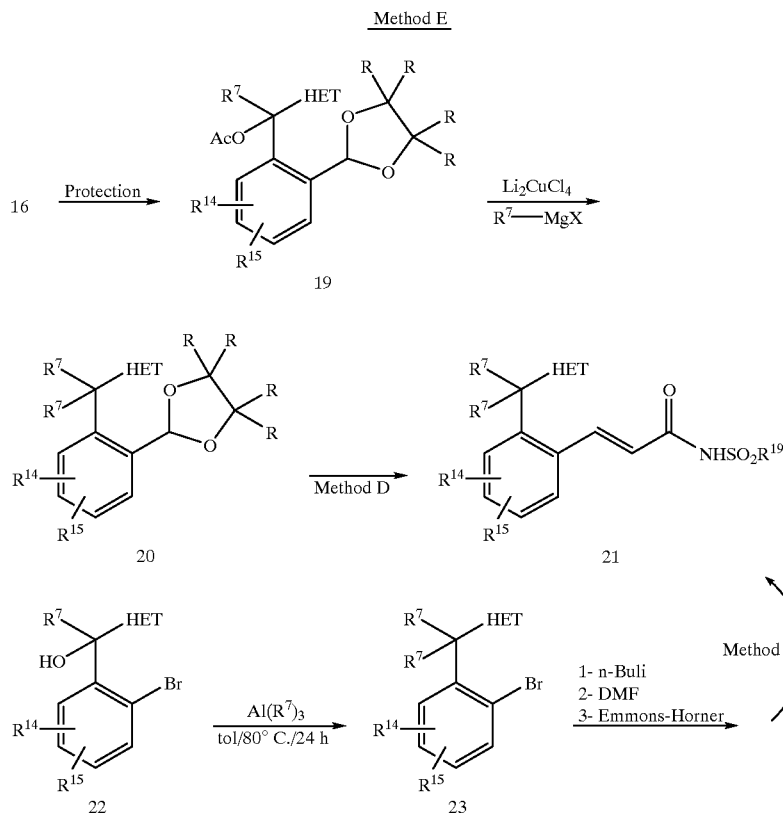
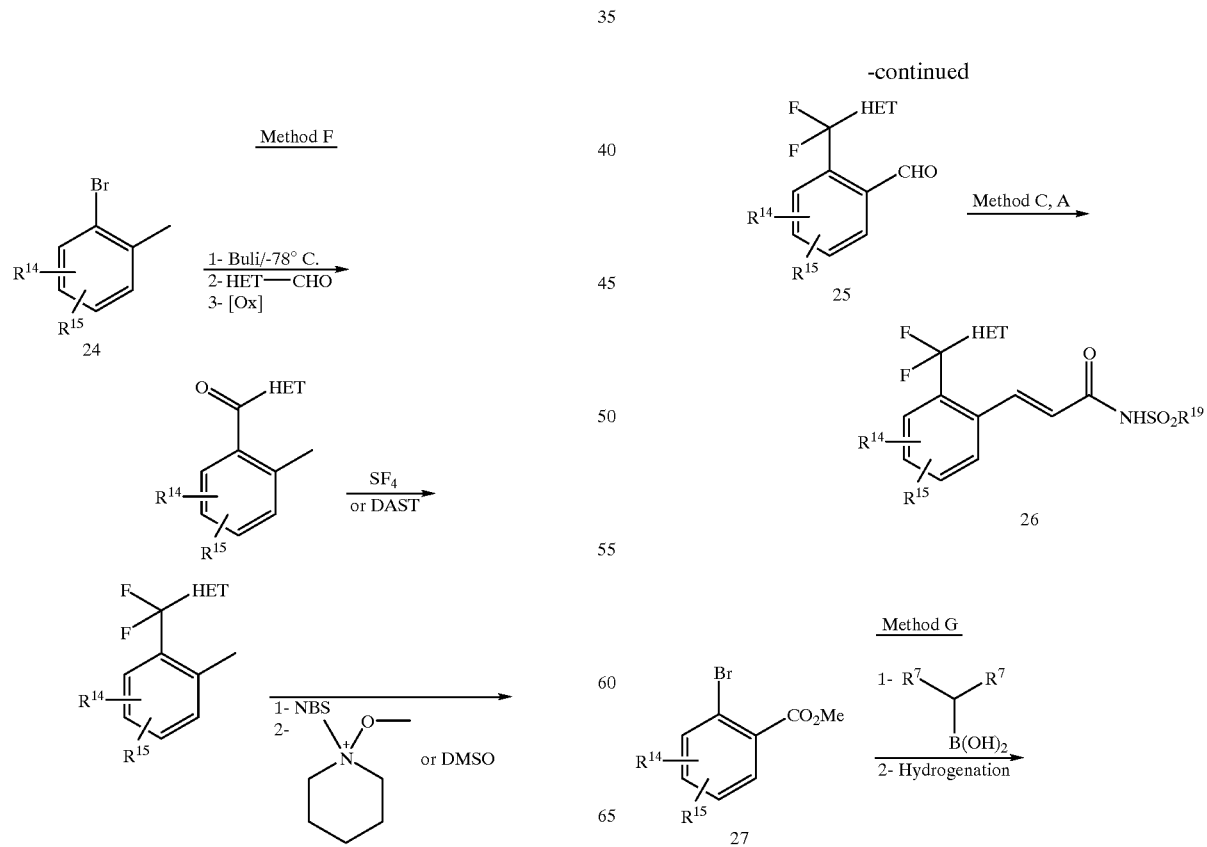

-continued
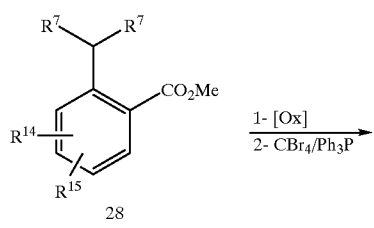
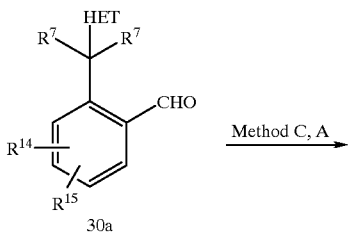
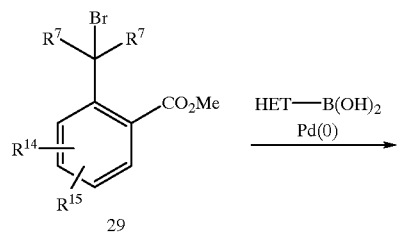
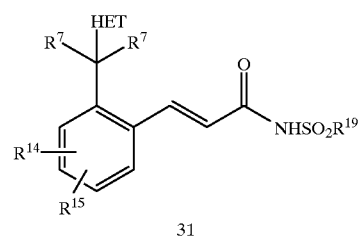
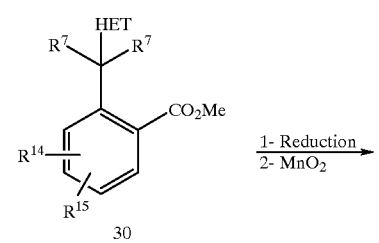
Method H
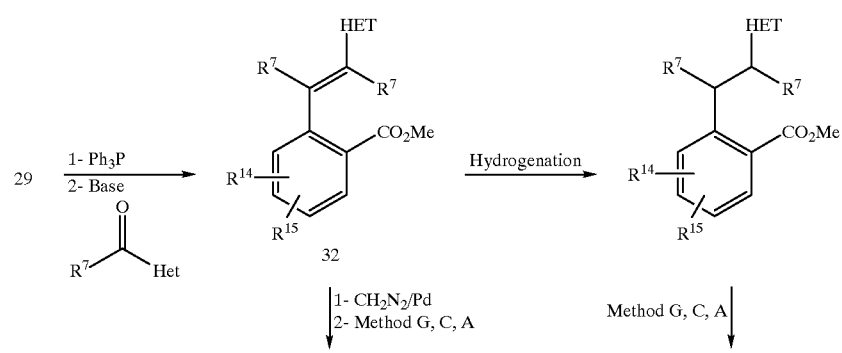

-continued
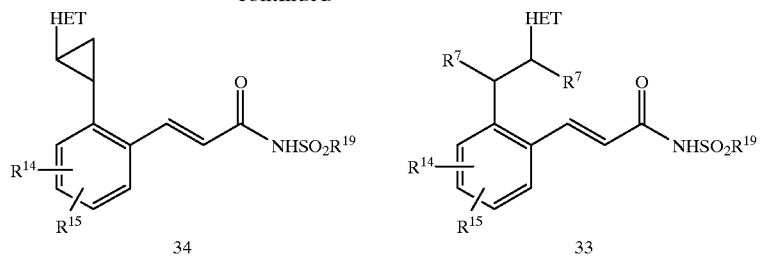
Method I
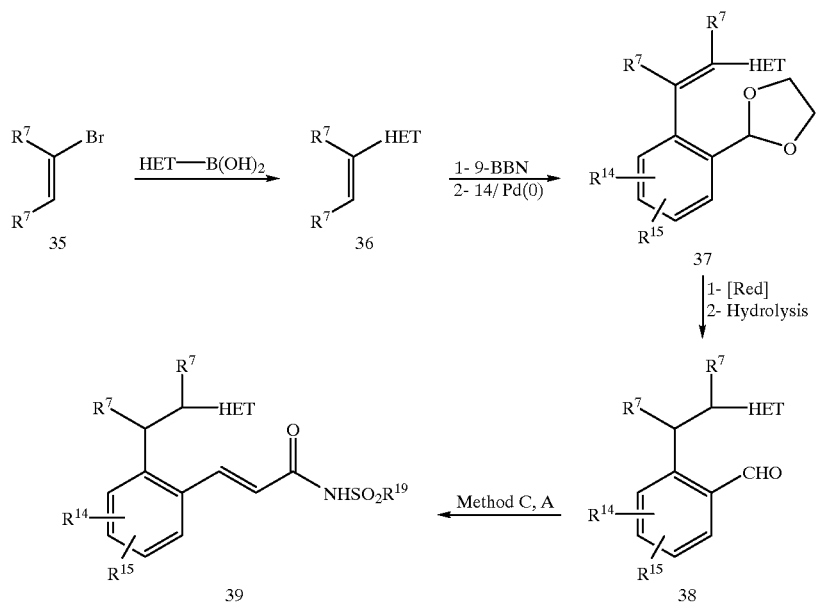
Method J
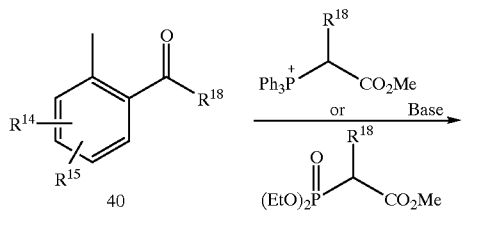
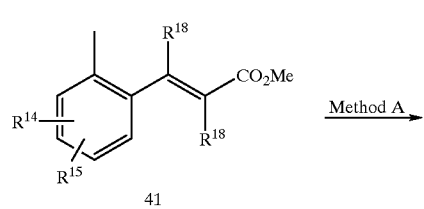
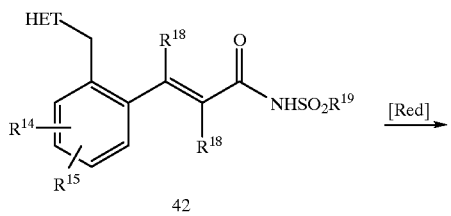
-continued
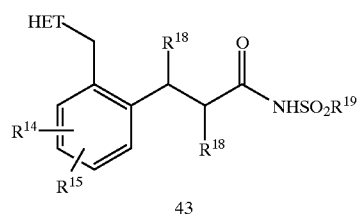
Method K
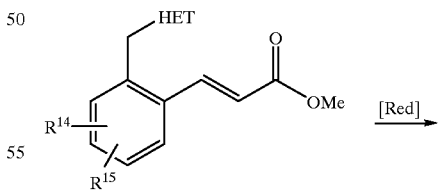
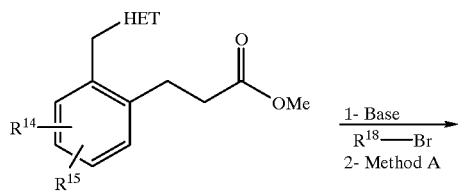

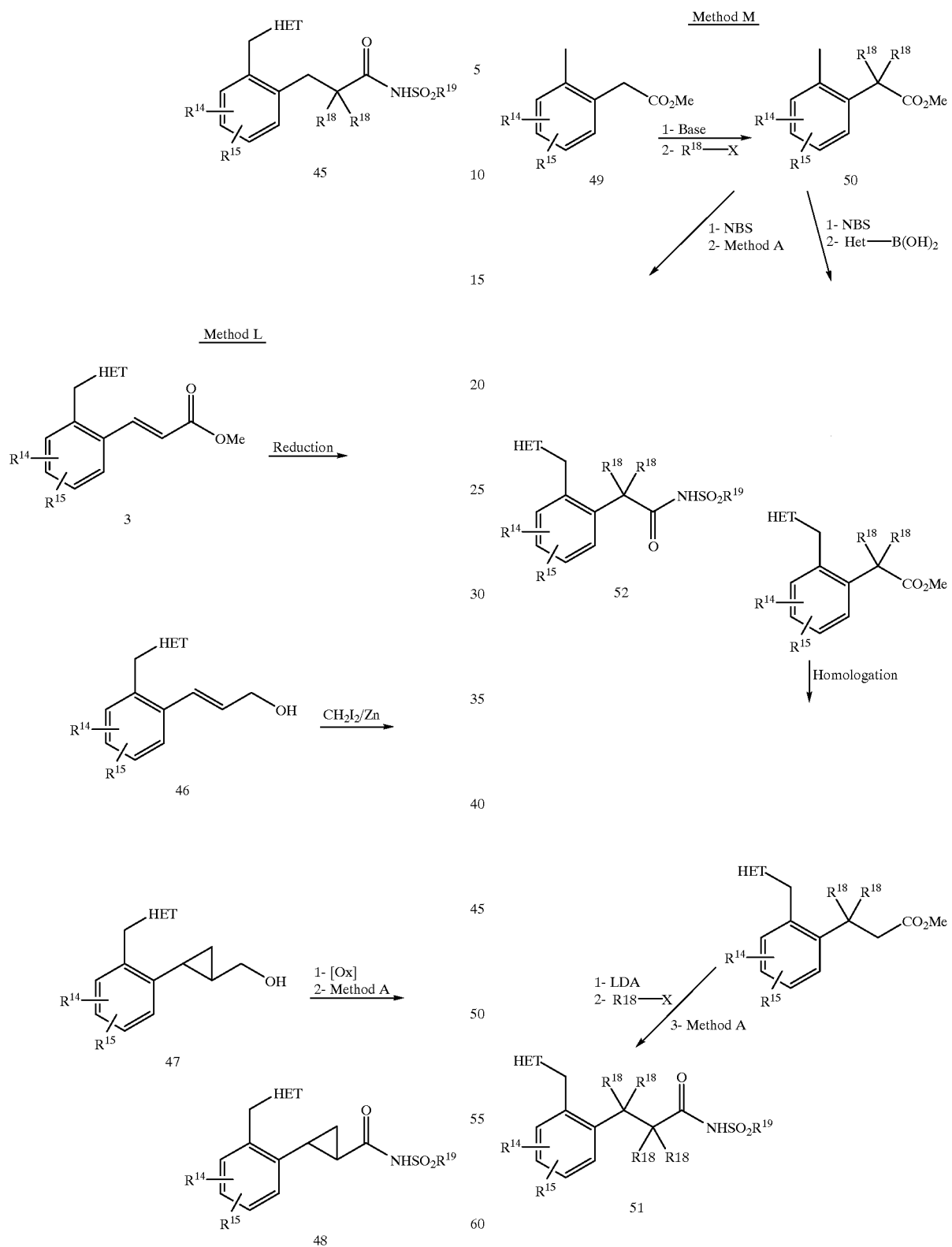

Method N
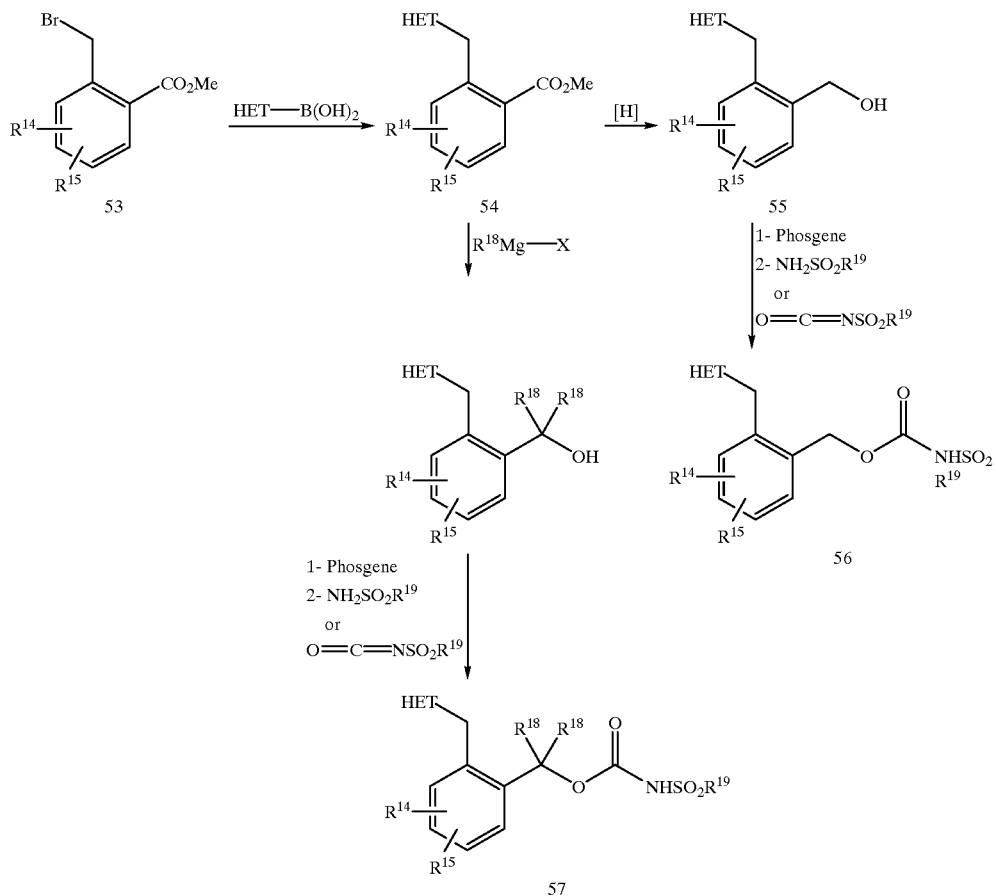
Method O
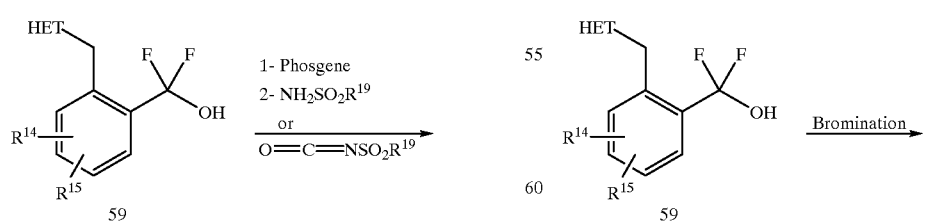
-continued
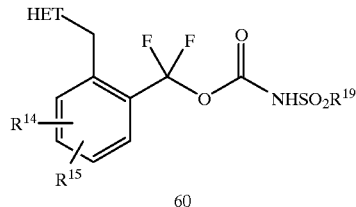
Method P

-continued
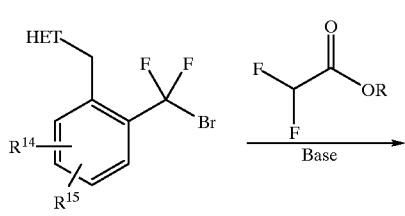
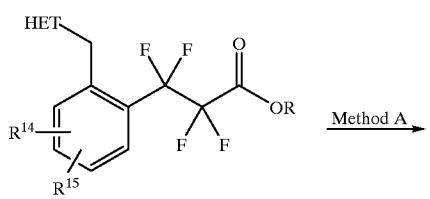
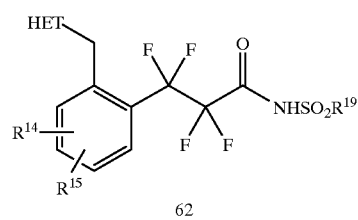
Method Q
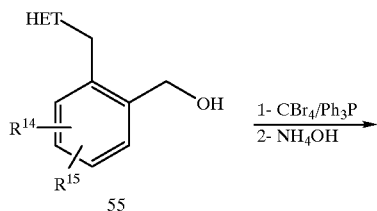
-continued
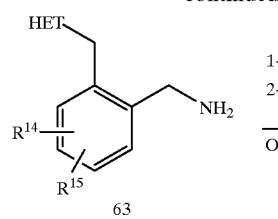
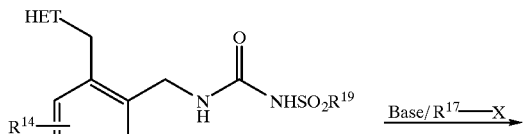
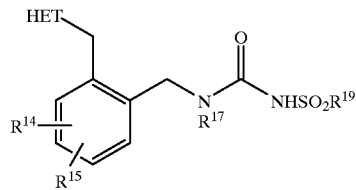
Method R
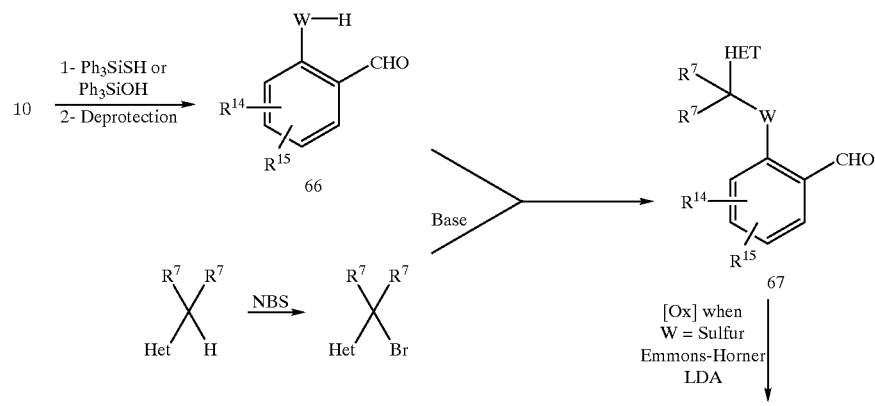

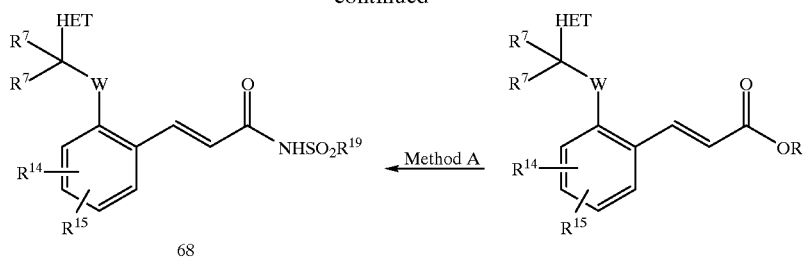
Method S
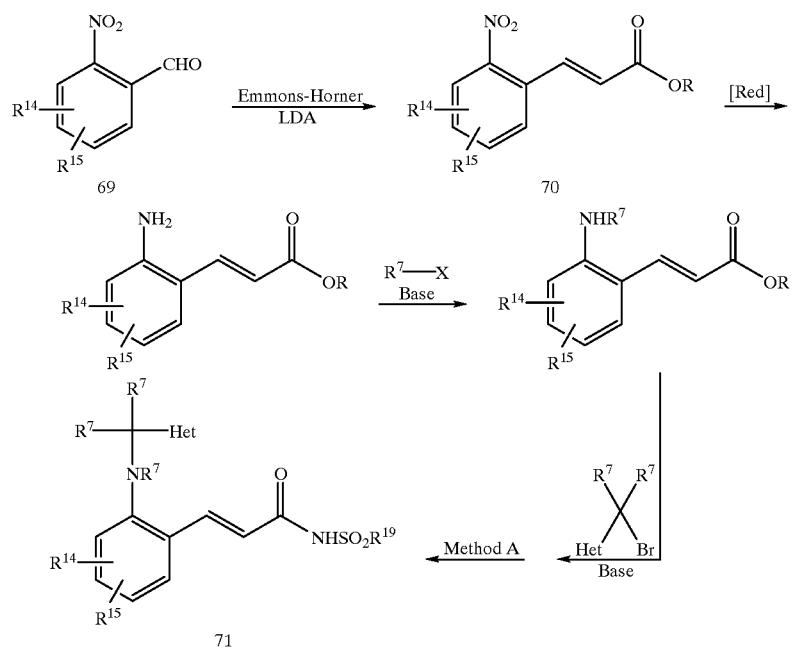
Method T
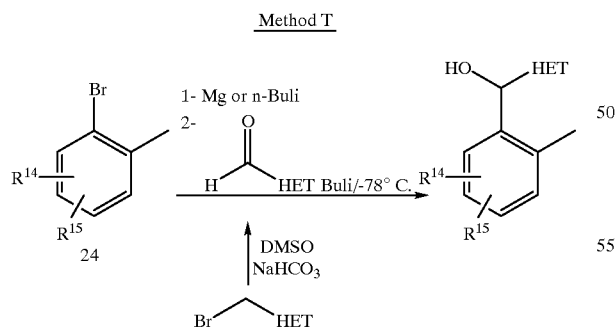
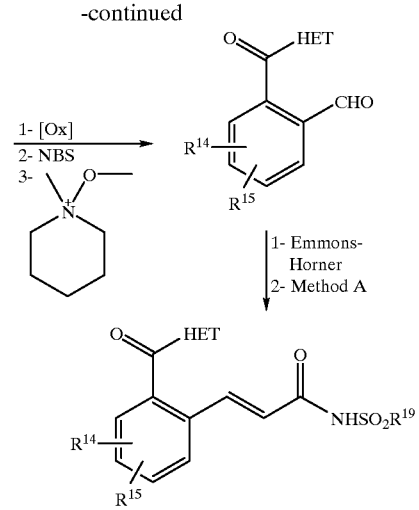

Assays for Determining Biological Activity

Biological activity and thus utility for the compounds of formula I as modulators of prostaglandin mediated diseases can be demonstrated in accordance with the following assays which demonstrate prostanoid antagonist or agonist activity in vitro and in vivo and their selectivity. The prostaglandin receptors investigated were DP, $EP_1$, $EP_2$, $EP_3$, $EP_4$, FP, IP and TP.

Stable Expression of Prostanoid Receptors in the Human Embryonic Kidney (HEK) 293(ebna) Cell Line Prostanoid receptor cDNAs corresponding to full length coding sequences were subcloned into the appropriate sites of mammalian expression vectors and transfected into HEK 293(ebna) cells. HEK 293(ebna) cells expressing the individual cDNAs were grown under selection and individual colonies were isolated after 2–3 weeks of growth using the cloning ring method and subsequently expanded into clonal cell lines.

Prostanoid Receptor Binding Assays

HEK 293(ebna) cells are maintained in culture, harvested and membranes are prepared by differential centrifugation, following lysis of the cells in the presence of protease inhibitors, for use in receptor binding assays. Prostanoid receptor binding assays are performed in 10 mM MES/KOH (pH 6.0) (EPs, FP and TP) or 10 mM HEPES/KOH (pH 7.4) (DP and IP), containing 1 mM EDTA, 10 mM divalent cation and the appropriate radioligand. The reaction is initiated by addition of membrane protein. Ligands are added in dimethylsulfoxide which is kept constant at 1% (v/v) in all incubations. Non-specific binding is determined in the presence of 1 $\mu$M of the corresponding non-radioactive prostanoid. Incubations are conducted for 60 min at room temperature or 30° C. and terminated by rapid filtration. Specific binding is calculated by subtracting non specific binding from total binding. The residual specific binding at each ligand concentration is calculated and expressed as a function of ligand concentration in order to construct sigmoidal concentration-response curves for determination of ligand affinity.

Prostanoid Receptor Agonist and Antagonist Assays

Whole cell second messenger assays measuring stimulation ($EP_2$, $EP_4$, DP and IP in HEK 293(ebna) cells) or inhibition ($EP_3$ in human erythroleukemia (HEL) cells) of intracellular cAMP accumulation or mobilization of intracellular calcium (EP1, FP and TP in HEK 293(ebna) cells stably transfected with apo-aequorin) are performed to determine whether receptor ligands are agonists or antagonists. For cAMP assays, cells are harvested and resuspended in HBSS containing 25 mM HEPES, pH 7.4. Incubations contain 100 $\mu$M RO-20174 (phosphodiesterase type IV inhibitor, available from Biomol) and, in the case of the $EP_3$ inhibition assay only, 15 $\mu$M forskolin to stimulate cAMP production. Samples are incubated at 37° C. for 10 min, the reaction is terminated and cAMP levels are then measured. For calcium mobilization assays, cells are charged with the co-factors reduced glutathione and coelenterazine, harvested and resuspended in Ham's F12 medium. Calcium mobilization is measured by monitoring luminescence provoked by calcium binding to the intracellular photoprotein aequorin. Ligands are added in dimethylsulfoxide which is kept constant at 1% (v/v) in all incubations. For agonists, second messenger responses are expressed as a function of ligand concentration and both $EC_{50}$ values and the maximum response as compared to a prostanoid standard are calculated. For antagonists, the ability of a ligand to inhibit an agonist response is determined by Schild analysis and both KB and slope values are calculated.

Rat Paw Edema Assay

The method is the same as described in Chan et al (J. Pharmacol. Exp. Ther. 274: 1531–1537, 1995).

LPS-Induced Pyrexia in Conscious Rats

The method is the same as described in Chan et al (J. Pharmacol. Exp. Ther. 274: 1531–1537, 1995).

LPS-Induced Pyrexia in Conscious Squirrel Monkeys

The method is the same as described in Chan et al (Eur. J. Pharmacol. 327: 221–225, 1997).

Acute Inflammatory Hyperalgesia Induced by Carrageenan in Rats

The method is the same as described in Boyce et al (Neuropharmacology 33: 1609–1611, 1994).

Adjuvant-Induced Arthritis in Rats

Female Lewis rats (body weight ~146–170 g) were weighed, ear marked, and assigned to groups (a negative control group in which arthritis was not induced, a vehicle control group, a positive control group administered indomethacin at a total daily dose of 1 mg/kg and four groups administered with a test compound at total daily doses of 0.10–3.0 mg/kg) such that the body weights were equivalent within each group. Six groups of 10 rats each were injected into a hind paw with 0.5 mg of *Mycobacterium butyricum* in 0.1 mL of light mineral oil (adjuvant), and a negative control group of 10 rats was not injected with adjuvant. Body weights, contralateral paw volumes (determined by mercury displacement plethysmography) and lateral radiographs (obtained under Ketamine and Xylazine anesthesia) were determined before (day −1) and 21 days following adjuvant injection, and primary paw volumes were determined before (day −1) and on days 4 and 21 following adjuvant injection. The rats were anesthetized with an intramuscular injection of 0.03–0.1 mL of a combination of Ketamine (87 mg/kg) and Xylazine (13 mg/kg) for radiographs and injection of adjuvant. The radiographs were made of both hind paws on day 0 and day 21 using the Faxitron (45 kVp, 30 seconds) and Kodak X-OMAT TL film, and were developed in an automatic processor. Radiographs were evaluated for changes in the soft and hard tissues by an investigator who was blinded to experimental treatment. The following radiographic changes were graded numerically according to severity: increased soft issue volume (0-4), narrowing or widening of joint spaces (0-5) subchondral erosion (0-3), periosteal reaction (0-4), osteolysis (0-4) subluxation (0-3), and degenerative joint changes (0-3). Specific criteria were used to establish the numerical grade of severity for each radiographic change. The maximum possible score per foot was 26. A test compound at total daily doses of 0.1, 0.3, 1, and 3 mg/kg/day, indomethacin at a total daily dose of 1 mg/kg/day, or vehicle (0.5% methocel in sterile water) were administered per os b.i.d. beginning post injection of adjuvant and continuing for 21 days. The compounds were prepared weekly, refrigerated in the dark until used, and vortex mixed immediately prior to administration.

The invention is illustrated in connection with the following non-limiting Examples. All the end products of the formula I were analyzed by NMR, TLC and mass spectrometry.

Intermediates were analyzed by NMR and TLC.

Most compounds were purified by flash chromatography on silica gel. Recrystallization and/or swish (suspension in a solvent followed by filtration of the solid) with a solvent such as ether:hexane 1:1.

The course of reactions was followed by thin layer chromatography (TLC) and reaction times are given for illustration only.

Temperatures are in degrees Celsius.
The compounds of the examples are numbered in accordance with the compounds that appear in Tables I and II.

EXAMPLE 1

N-((E)-3-{2-[4-(METHYLTHIO)BENZYL]
PHENYL}-2-PROPENOYL)-2-
THIOPHENESULFONAMIDE (17)

Step 1: Methyl (E)-3-(2-methylphenyl)-2-propenoate

To 2-methylcinnamic acid (100 g; 617 mmol) in 1.2L of DMF was added DBU (112.6 g; 740 mmol) and 15 min later methyl iodide (131.3 g; 925 mmol) and left overnight. The solution was diluted in ether and washed with HCl (10%), $H_2O$ and brine. The solvent was removed to give 106.8 g of the title compound.

$^1$H NMR (CDCl$_3$) δ2.4 (3H, s), 3.8 (3H, s), 6.35 (1H, d), 7.15 (1H, t), 7.22 (1H, t), 7.5 (1H, d) and 7.95 (1H, d).

The ethyl ester can be prepared as well in the same way or from the 2-methyl benzaldehyde (5.00 g; 41.6 mmol) and triethyl phosphonoacetate (9.9 mL; 50.0 mmol) in 150 mL ot toluene at 0° C., to which was added portionwise NaH (63.0 mmol). After 2 h of stirring the mixture was quenched with NH$_4$OAc (25%) and extracted with EtOAc. The solvent was removed to give 7.1 g of the ethyl cinnamate.

Step 2: Ethyl (E)-3-[2-(bromomethyl)phenyl]-2-propenoate

To the previous ethyl cinnamate (20.0 g; 105 mmol) and NBS (19.64 g; 110.3 mmol) in refluxing CCl$_4$ was added benzoyl peroxide (1.27 g) and the mixture was stirred for 12 h. The solution was cooled to r.t. and filtered. The solvent was removed and the crude oil purified by silica gel chromatography (5% EtOAc in hexane) to yield 14.18 g of the title compound.

$^1$H NMR (CDCl$_3$) δ1.30 (3H, t), 4.25 (2H, q), 4.60 (2H, s), 6.45 (1H, d), 7.30 (3H, m), 7.57 (1H, m) and 8.05 (1H, d).

Step 3: Ethyl (E)-3-{2-[4-(methylthio)benzyl]phenyl}-2-propenoate

A mixture of the previous benzyl bromide (0.50 g; 1.86 mmol), 4-(methylthio)benzeneboronic acid (0.63 g; 3.7 mmol) CsF (1.13 g) and (Ph$_3$P)$_4$Pd (0.11 g) in 10 mL of DME was heated to reflux for 10 h. The mixture was cooled to r.t. and quenched with NH$_4$OAc (25%) and extracted with EtOAc. The organic phases were combined, dried and the solvent removed. Purification by silica gel chromatography (10% EtOAc in hexane) yielded 0.35 g of the title compound.

$^1$H NMR (CDCl$_3$) δ1.27 (3H, t), 2.41 (3H, s), 4.08 (2H, s), 4.21 (2H, q), 6.30 (1H, d), 7.00 (1H, d), 7.1–7.4 (6H, m), 7.55 (1H, d) and 7.97 (1H, d).

Step 4: (E)-3-{2-[4-Methylthio)benzyl]phenyl}-2-propenoic acid

Hydrolysis of the previous ester (0.34 g; 1.1 mmol) was run in THF/MeOH (6 mL/3 mL) with 2 equivalent of a 2N NaOH solution for 4 h. The solution was diluted with EtOAc and quenched with HCl (10%). The organic phase was dried over Na$_2$SO$_4$ and the solvent removed. Purification was done by a swish in hexane to yield 0.21 g of the title compound.

$^1$H NMR (CDCl$_3$) δ2.42 (3H, s), 4.09 (2H, s), 6.31 (1H, d), 7.00–7.35 (7H, m), 7.50 (1H, d) and 8.07 (1H, d).

Step 5: N-((E)-3-{2-[4-(methylthio)benzyl]phenyl}-2-propenoyl)-2-thiophenesulfonamide (17)

2-Thiophenesulfonamide was prepared from the corresponding sulfonyl chloride with 2.2 equivalent of NH$_4$OH in THF at 0° C. The solution was brought to r.t. and left 2 h. It was then quenched with NaHCO$_3$ and extracted with EtOAc. The organic phase was dried over Na$_2$SO$_4$ and the solvent removed. The crude product was crystallized in toluene/EtOAc.

To the previous acid (100 mg; 0.35 mmol), 2-thiophenesulfonamide (60 mg; 0.37 mmol), DMAP (86 mg; 0.7 mmol) in 2 mL of CH$_2$Cl$_2$ was added DCI (134 mg; 0.7 mmol) and the mixture was stirred overnight. The solution was diluted with EtOAc and quenched with HCl (10%). The organic phase was dried over Na$_2$SO$_4$ and the solvent removed. Purification by silica gel chromatography (5% MeOH in CH$_2$Cl$_2$) yielded 87 mg of the title compound.

$^1$H NMR (CDCl$_3$) δ2.40 (3H, s), 4.01 (2H, s), 6.33 (1H, d), 6.9–7.3 (8H, m), 7.49 (1H, d), 7.61 (1H, s), 7.89 (1H, s) and 8.03 (1H, d). The product was converted to the sodium salt with 1 equivalent of NaOH and freeze dried.

Elemental analysis calcd. for C$_{21}$H$_{18}$NNaO$_3$S$_3$.1/2H$_2$O: C, 54.77; H, 4.13; N, 3.04; S, 20.88; Found: C, 54.55; H, 4.01; N, 3.06; S, 20.58.

EXAMPLE 2

N-((E)-3-{2-[(3-METHYL-1H-1-INDOLYL)
METHYL]PHENYL}-2-PROPENOYL)-2-
THIOPHENESULFONAMIDE (3)

Step 1: Ethyl (E)-3-{2-[(3-methyl-1H-1-indolyl)methyl]phenyl}-2-propenoate

To benzylic bromide (400 mg, 1.49 mmol) of step 2 in example 1 and skatole (200mg, 1.51 mmol) in 6 mL of DMF was added portionwise 1.6 equivalent of NaH. The reaction mixture was left for 6 h and quenched with NH$_4$OAc (25%) and diluted with EtOAc. The organic phase was dried over Na$_2$SO$_4$, filtered and the solvent removed. Purification by silica gel chromatography (10% EtOAc inhexane) yielded 260 mg of the title compound.

$^1$H NMR (CDCl$_3$) δ1.2 (31, t), 2.3 (3H, s), 4.25 (2H, q), 5.4 (2H, s), 6.35 (1H, d), 6.65 (1H, d), 6.8 (1H, s), 7.1–7.3 (5H, m), 7.56 (2H, d) and 7.97 (1H, d).

Step 2: (E)-3-{2-[(3-methyl-1H-1indolyl)methyl]phenyl}-2-propenoic acid

The hydrolysis of the previous ester (260 mg) was done according to Step 4 of example 1 to yield 212 mg of the title compound.

HRMS calcd. for C$_{19}$H$_{17}$NO$_3$+H$^+$=292.1337; Found: 292.1337.

Step 3: N2-((E)-3-{2-[(3-methyl-1H-1-indolyl)methyl]phenyl}-2-propenoyl)-2-thiophenesulfonamide (3)

The coupling reaction of the previous acid (196 mg; 0.67 mmol) was done according to step 5 of example 1 to yield 134 mg of the title compound.

$^1$H NMR (acetone-d$_6$) δ2.39 (3H, , 4), 5.57 (2H, 4), 6.65 (2H, m), 7.03 (31H, m), 7.27 (4H, m), 7.5 (2H, d), 7.63 (1H, d), 7.87 (1H, d), 7.95 (1H, s) and 8.14 (1H, d).

HRMS calcd. for C$_{23}$H$_{20}$N$_2$O$_3$S$_2$+H$^+$=437.0994; Found: 437.0992.

EXAMPLE 3

N-{(E)-3-[2-(2-NAPHTHYLMETHYL)PHENYL]-2-PROPENOYL}-2-THIOPHENESULFONAMIDE (4)

Step 1: Ethyl (E)-3-[2-(2-naphthylmethyl)phenyl]-2-propenoate

The benzyl bromide (500 mg) of example 1, step 2 was treated with 2-naphthylboronic acid according to the same procedure previously described to yield 360 mg of the title compound.

$^1$H NMR (CDCl$_3$) δ1.30 (3H, t), 4.27(2H, q), 4.33 (2H, s), 6.48 (1H, d), 7.2–7.4 (41H, m), 7.45 (21H, m), 7.55 (1H, ), 7.62 (1, d), 7.8 (3H, m) and 8.15 (1H, d).

Step 2: (E)-3-[2-(2-naphthylmethyl)phenyl]-2-propenoic acid

The hydrolysis of the previous ester (300 mg) was done according to Step 4 of example 1 to yield 202 mg of the title compound.

$^1$H NMR (CDCl$_3$) δ4.29 (2H, s), 6.32 (1H, d), 7.2–7.4 (6H, m), 7.5 (1H, s), 7.62 (1H, d), 7.73 (3H, m) and 8.19 (1H, d).

Step 3: N-{(E)-3-[2-(2-naphthylmethyl)phenyl]-2-propenoyl}-2-thiophenesulfonamide (4)

The coupling reaction of the previous acid (100 mg; 0.35 mmol) was done according to step 5 of example 1 to yield 60 mg of the title compound.

1H NMR (CDCl$_3$) δ4.24 (2H, s), 6.31 (1H, d), 7.02 (1H, m), 7.15–7.8 (12H, m), 7.84 (1H, m) and 8.08 (1H, d).

The acid was converted to the sodium salt with 1 equivalent of NaOH.

Elemental analysis calcd. for C$_{24}$H$_{18}$NNaO3S$_2$.H$_2$O: C, 60.87; H, 4.22; N, 2.96; S, 13.54; Found: C, 60.36; H, 4.25; N, 3.29; S, 12.53.

EXAMPLE 4

N-{(E)-3-[2-(3,4-DICHLOROBENZYL)PHENYL]-2-PROPENOYL-2-THIOPHENESULFONAMIDE (8)

Step 1: Ethyl (E)-3-[2-(3,4-dichlorobenzyl)phenyl]-2-propenoate

The benzyl bromide (500 mg) of example 1, step 2 was treated with 3,4-dichlorobenzeneboronic acid according to the same procedure described in step 3 of example 1 to yield 410 mg of the title compound.

$^1$H NMR (CDCl$_3$) δ1.30 (3H, t), 4.03 (2H, s), 4.23 (2H, q), 6.28 (1H, d), 6.90 (1H, dd), 7.1–7.4 (5H, m), 7.57 (1H, d) and 7.89 (1H, d).

Step 2: (E)-3-[2-(3,4-dichlorobenzyl)phenyl]-2-propenoic acid

The hydrolysis of the previous ester (400 mg) was done according to Step 4 of example 1 to yield 296 mg of the title compound.

$^1$H NMR (CDCl$_3$) δ4.07 (2H, s), 6.31 (1H, d), 6.93 (1H, dd), 7.1–7.4 (5H, m), 7.50 (1H, d) and 7.99 (1H, d).

Step 3: N-{(E)-3-[2-(3,4-dichlorobenzyl)phenyl]-2-propenoyl}-2-thiophenesulfonamide (8)

The coupling reaction of the previous acid (170 mg; 0.55 mmol) was done according to step 5 of example 1 to yield 110 mg of the title compound.

$^1$H NMR (CDCl$_3$) δ4.07 (2H, s), 6.33 (1H, d), 6.85 (1H, d), 7.07 (3H, m), 7.24 (2H, m), 7.32 (1H, t), 7.53 (1H, d), 7.63 (1H, d), 7.88 (1H, d) and 7.97 (1H, d).

The acid was converted to the sodium salt with 1 equivalent of NaOH.

Elemental analysis calcd. for C$_{20}$H$_{14}$Cl$_2$NNaO$_3$S$_2$.1/2H$_2$O: C, 49.7; H, 3.1; N, 2.9; S, 13.27; Found:: C, 49.46; H, 2.9; N, 2.86; S, 13.73;

EXAMPLE 5

N-((E)-3-{2-[(2-NAPHTHYLOXY)METHYL]PHENYL}-2-PROPENOYL)-2-THIOPHENESULFONAMIDE (20)

Step 1: Ethyl (E)-3-{2-[naphthyloxy)methyl]phenyl}-2-propenoate

The benzyl bromide (250 mg, 0.93 mmol) of step 2 in example 1 and 2-naphthol (147 mg) in 5 mL of DMF were treated with cesium carbonate (394 mg) at 40° C. for 12 h. The mixture was diluted with EtOAc and washed with water and brine. The organic phase was dried over Na$_2$SO$_4$, filtered and the solvent removed. Purification by silica gel chromatography (10% EtOAc in hexane) yielded 245 mg of the title compound.

$^1$H NMR (CDCl$_3$) δ1.2 (3H, t), 4.22 (2H, q), 5.28 (2H, s), 6.41 (1H, d), 7.22 (2H, m), 7.3–7.5 (4H, m), 7.55 (1H, m), 7.64 (1H, m), 7.75 (3H, m) and 8.05 (1H, d).

Step 2: (E)-3-{2-[naphthyloxy)methyl]phenyl}-2-propenoic acid

Hydrolysis of the previous ester (245 mg, 0.74 mmol) was done according to step 4 of example 1 to yield 185 mg of the title compound.

$^1$H NMR (CDCl3) δ5.27 (2H, s), 6.45 (1H, d), 7.15–7.25 (2H, m), 7.32 (1H, t), 7.42 (3H, m), 7.55 (1H, d), 7.67 (1H, d), 7.77 (3H, m) and 8.11 (1H, d).

Step 3: N-((E)-3-{2-[(2-naphthyloxy)methyl]phenyl}-2-propenoyl)-2-thiophenesulfonamide (20)

The coupling reaction of the previous acid (150 mg; 0.49 mmol) was done according to step 5 of example 1 to yield 77 mg of the title compound.

$^1$H NMR (CDCl$_3$) δ5.2 (2H, s), 6.39 (1H, d), 7.02 (1H, s), 7.1–7.2 (2H, m), 7.3–7.4 (4H, m), 7.53 (3H, m), 7.71 (3H, m), 7.83 (1H, s) and 8.07 (1H, d).

The product was converted to the sodium salt with 1 equivalent of NaOH.

Elemental analysis calcd. for C$_{24}$H$_{28}$NNaO$_4$S$_2$.3/2H$_2$O: C, 57.82; H,4.21; N, 2.81; Found:: C, 58.31; H, 3.96; N, 2.91.

EXAMPLE 6

N-{(E)-3-[2-(2-NAPHTHYLSULFINYL)PHENYL]-2-PROPENOYL}-2-THIOPHENESULFONAMIDE (21)

Step 1: 2-(2-naphthylthio)benzaldehyde

A mixture of 2-thionaphthol (5.29 g; 33 mmol), 2-fluorobenzaldehyde (3.73 g; 33 mmol) and potassium carbonate (4.57 g; 33 mmol) in 28 mL of iso-propanol was heated to reflux for 12 h. The mixture was cooled to r.t., diluted with water and filtered. The solution was diluted with EtOAc and washed with water, brine and dry over MgSO$_4$. The crude product (7.9 g) was used as is for the next step.

$^1$H NMR (CDCl$_3$) δ7.07 (1H, d), 7.32 (2H, m), 7.42 (1H, d), 7.51 (2H, m), 7.78 (1H, m), 7.83 (2H, d), 7.88 (1H, s), 7.95 (1H, s) and 10.39 (1H, s).

Step 2: Ethyl (E)-3-[2-(2-naphthylthio)phenyl]-2-propenoate

The previous aldehyde (7.72 g; 29.2 mmol) was converted to the ethyl ester according to step 1 of example 1 to furnish 6.36 g of the title compound.

$^1$H NMR (CDCl$_3$) δ1.24 (3H, t), 4.21 (2H, q), 6.36 (1H, d), 7.28 (4H, m), 7.42 (2H, m), 7.61 (1H, d), 7.72 (4H, m) and 8.28 (1H, d).

Step 3: Ethyl (E)-3-[2-(2-naphthylsulfinyl)phenyl]-2-propenoate

The previous ester (3.00 g; 8.97 mmol) in 45 mL of dichloromethane was treated with 1.1 equivalent of mCPBA at 0° C. for 1 h. The mixture was quenched with sodium thiosulfite and extracted with EtOAc. The organic phase was dry over $Na_2SO_4$ and the crude purified by silica gel chromatography (30% EtOAc in hexane) to yield 2.35 g of the title compound.

$^1$H NMR (CDCl$_3$) δ1.34 (3H, t), 4.27 (2H, q), 6.26 (1H, d), 7.42 (2H, m), 7.53 (4H, m), 7.77 (2H, m), 7.88 (2H, m), 8.07 (2H, d), 8.22 (1H, s) and 8.28 (2H, m).

Step 4: Ethyl (E)-3-[2-(2-naphthylsulfinyl)phenyl]-2-propenoic acid

The previous ester (1.20 g; 3.43 mmol) was hydrolyzed according to the procedure of step 4 of example 1 to yield 1.08 g of the title compound.

$^1$H NMR (methanol-d$_6$) δ6.23 (1H, d), 7.33 (1H, dd), 7.45 (3H, m), 7.53 (1H, t), 7.62 (1H, d), 7.8 (3H, m), 7.98 (1H, d), 8.05 (1H, d) and 8.27 (1H, s).

Step 5: 2-{(E)-3-[2-(2-naphthylsulfinyl)phenyl]-2-propenoyl}-2-thiophenesulfonamide (21)

The coupling reaction of the previous acid (500 mg; 1.55 mmol) was done according to step 5 of example 1 to yield 416 mg of the title compound.

$^1$H NMR (methanol-d$_6$) δ6.19 (1H, d), 7.1 (1H, m), 7.22 (1H, dd), 7.45 (3H, m), 7.55 (2H, m), 7.67 (1H, d), 7.72–7.85 (4H, m), 7.99 (1H, d), 8.1 (1H, d) and 8.17 (1H, s).

The sodium salt was prepared with 1N NaOH.

Elemental analysis calcd. for $C_{23}H_{16}NNaO_4S_3 \cdot 1/2H_2O$: C, 55.36; H, 3.40; N, 2.81; S, 19.27; Found:: C, 55.00; H, 3.62; N, 2.81; S, 18.18.

EXAMPLE 7

N-{(E)-3-[2-(2-NAPHTHYLOXY)PHENYL]-2-PROPENOYL}-2-THIOPHENESULFONAMIDE (28)

Step 1: Ethyl (E)-3-[2-(2-naphthyloxy)phenyl]-2-propenoate 2-fluoro benzaldehyde (3.0 g, 24.2 mmol), 2-napthiol (24.2 mmol) and potassium carbonate (26.6 mmol) were heated at reflux in dimethyl acetamide for 2 h. The mixture was cooled to r.t., diluted with EtOAc and washed with water and brine. The organic phase was dried over $Na_2SO_4$, filtered and the solvent removed. Purification by silica gel chromatography (10% EtOAc in hexane) yielded 3.4 g of the title compound.

$^1$H NMR (CDCl$_3$) δ6.93 (1H, d), 7.17–7.23 (1H, m), 7.28 (1H, dd), 7.37 (1H, s), 7.37 (3H, m), 7.7 (1H, d), 7.84 (2H, m), 7.94 (1H, d) and 10.53 (1H, s).

Step 2: Ethyl (E)-3-[2-(2-naphthyloxy)phenyl]-2-propenoate

The previous aldehyde (2.00 g; 8.0 mmol) was converted to the title compound according to step 1 of example 1 to yield 2.52 g.

$^1$H NMR (CDCl$_3$) δ1.25 (3H, t), 4.21 (2H, q), 6.55 (1H, d), 6.9 (1H, d), 7.15 (1H, t), 7.25 (3H, m), 7.42 (2H, m), 7.65 (2H, m), 7.83 (2H, t) and 8.02 (1H, d).

Step 3: (E)-3-[2-(2-naphthyloxy)phenyl]-2-propenoic acid

The previous ester (2.52 g; 7.9 mmol) was hydrolyzed according to the procedure of step 4 of example 1 to yield 1.57 g of the title compound.

$^1$H NMR (CDCl$_8$) δ6.62 (1H, d), 7.03 (1H, d), 7.2–7.5 (6H, m), 7.78 (1H, d) and 7.88–8.03 (4H, m). HRMS calcd. for $C_{19}H_{14}O_3+H^+=291.1021$; Found: 291.1022.

Step 4: N-{(E)-3-[2-(2-naphthyloxy)phenyl]-2-propenoyl}-2-thiophenesulfonamide (28)

The coupling reaction of the previous acid (1.00 g; 3.4 mmol) was done according to step 5 of example 1 to yield 790 mg of the title compound.

$^1$H NMR (CDCl$_3$) δ6.91 (1H, d), 6.97 (1H, d), 7.15(1H, dd), 7.24 (1H, t), 7.29 1H, dd), 7.37 (5H, d), 7.40–7.55 (3H, m), 7.74–7.83 (20, m), 7.92 (2H, m) and 7.99 (2H, m).

The sodium salt was prepared with 1N NaOH. HRMS calcd. for $C_{23}H_{16}NNaO_4\ S_2+H^+=458.0497$; Found: 458.0497.

EXAMPLE 8

THIOPHENE-2-SULFONYL CARBAMIC ACID [2-(2-NAPHTHYLSULFONYL)PHENYL] METHYL ESTER (31)

Step 1: [2-(2-naphthylthio)phenyl]methanol

To 2-(2-naphthylthio)benzaldehyde (7.24 g; 27.4 mmol from Example 6, step 1) in 70 mL of methanol and 30 mL of THF at 0° C. was added NaBH$_4$ (54.8 mml) portionwise. After 1 h at 0° C., the solution was brought to r.t. and quenched with water. After dilution with EtOAc, the solution was washed with water and brine. The organic phase was dry over $Na_2SO_4$, filtered and the crude purified by silica gel chromatography to yield 6.71 g of the title compound.

$^1$H NMR (acetone-d$_6$) δ4.29 (1H, t), 4.7 (2H, d), 7.29 (2H, m), 7.35–7.52 (4H, m), 7.71 (2H, m), 7.77 (1H, m) and 7.83 (2H, m).

Step 2: [2-(2-Naphthylsulfonyl)phenyl]methanol

To the previous sulfide (500 mg; 1.88 mmol) in 8 mL of dichloromethane at 0° C. was added m-CPBA (5.64 mmol) and let stirred for 2 h. The mixture was diluted with EtOAc and washed with NaOH (1N) and brine. The organic phase was dry over $Na_2SO_4$, filtered and the crude purified by silica gel chromatography (40% EtOAc in hexane) to yield 390 mg of the title compound.

$^1$H NMR (acetone-d$_6$) δ4.37 (1H, t), 4,9 (2H, d), 7.57 (1H, dt), 7.65–7.80 (4H, m), 7.82 (1H, d), 8.0–8.1 (2H, m), 8.2 (2H, m) and 8.63 (1H, s).

Step 3: 2-Thiophenesulfonyl isocyanate

A mixture of 2-thiophenesulfonylamide (1.5 g) and oxalyl chloride (6 mL) in 10 mL of 1,2-dichloroethane was refluxed for 14 h. The solvent was removed under vacuum and the crude used as is for the next step.

Step 4:

To the alcohol of step 2 (250 mg; 0.84 mmol) in ether at 0° C. was added the previous isocyanate (2 equivalent) and let stirred 1 h at 0° C. The solution was quenched with water and extracted with EtOAc. The organic phase dry over $Na_2SO_4$, filtered and the crude purified by silica gel chromatography (5% $CH_3OH$ in $CH_2Cl_2$) to yield 300 mg of the title compound.

$^1$H NMR (CDCl$_3$) δ5.55 (2H, s), 7.08 (1H, m), 7.55–7.72 (6H, m), 7.82 (2H, m), 8.0 (1H, d), 8.07 (1H, d), 8.2 (2H, m) and 8.66 (1H, s).

The sodium salt was prepared with 1N NaOH.

Elemental analysis calcd. for $C_{22}H_{16}NNaO_6S_3 \cdot 2H_2O$: C, 48.44; H, 3.67; N, 2.57; S, 17.63;
Found:: C, 48.86; H, 3.13; N, 2.63; S, 16.46.

EXAMPLE 9

N-({2-[2-(2-NAPHTHYLMETHYL)PHENYL] CYCLOPROPYL}CARBONYL-2-THIOPHENESULFONAMIDE (45)

Step 1: Ethyl 2-[2-(2-naphthylmethyl)phenyl]-1-cyclopropanecarboxylate

The ethyl ester (300 mg; 0.95 mmol) of step 1 in example 3 and Pd(OAc)$_2$ (10 mg) were treated with diazomethane at 0° C. for 1 h. The solvent was removed and the crude oil purified by silica gel chromatography (5% EtOAc in hexane) to yield 300 mg of the title compound.

¹H NMR (CDCl₃) δ1.1 (3H, t), 1.27 (1H, m), 1.45 (1H, m), 1.7 1H, m), 2.53 (1H, m), 3.98 (2H, m), 4.29 (2H, s), 7.0 (1H, m), 7.18 (3H, m), 7.27 (1H, m), 7.39 (2H, m), 7.48 (1H, s) and 7.75 (3H, m).

Step 2: 2-[2-(2-naphthylmethyl)phenyl]-1-cyclopropanecarboxylic acid

The previous ester (300 mg; 0.91 mmol) was hydrolyzed according to the procedure of step 4 of example 1 to yield 230 mg of the title compound.

¹H NMR (CDCl) δ1.45 (1H, m), 1.6 (1H, m), 1.8 (1H, m), 2.67 (1H, m), 4.33 (2H, s), 7.1 (1H, m), 7.24 (4H, m), 7.41 (2H, m), 7.58 (1H, s) and 7.78 (3H, m).

Step 3: N-(2-[2-(2-naphthylmethyl)phenyl] cyclopropyl}carbonyl-2-thiophenesulfonamide (45)

The coupling reaction of the previous acid (230 mg; 0.76 mmol) was done according to step 5 of example 1 to yield 100 mg of the title compound.

¹H NMR (CDCl₃) δ1.32 (1H, m), 1.48 (1H, m), 1.63 (1H, m), 2.6 (1H, m), 4.13 (2H, s), 6.97 (2H, m), 7.12 (4H, m), 7.38 (3H, m), 7.52 (1H, d), 7.65 (2H, m) and 7.79 (2H, m).

The sodium salt was prepared with 1N NaOH.

Elemental analysis calcd. for $C_{25}H_{20}NNaO_3S_2 \cdot 1/2H_2O$: C, 62.75; H, 4.39; N, 2.93; S, 13.4; Found:: C,62.25; H, 4.24; N, 3.02; S, 12.15.

EXAMPLE 10

N-((E)-3-(2-(6-BENZYLOXY-2-NAPHTHYL) METHYL)PHENYL)-2-PROPENOYL)-5-BROMO-2-METHOXYBENZENESULFONAMIDE (46)

(E)-3-(2-(6-benzyloxy-2-naphthyl)methyl)phenyl)-2-propenoic acid

Step 1: [(6-bromo-2-naphthyl)oxy](phenyl)methane

To a mixture of 6-bromo-2-naphthol (1.99 g, 8.9 mmol) and benzyl bromide (1.2 ml, 1.1 equiv.) in DMF (18 ml) at 0° C. was added a suspension of NaH 80% in oil (324 mg, 1.2 equiv.) and the mixture was stirred at 0° C. for an hour and at r.t. for another hour. After addition of half saturated NH₄Cl, the product was extracted in i-PrOAc, washed with 1N HCl, dried over Na₂SO₄ and concentrated to yield 2.84 g of an oil.

Step 2: 6-benzyloxy-2-naphthaleneboronic acid

To a solution of the previous bromide (940 mg, 3.00 mmol) in THF (15 ml) at −78° C. was added n-BuLi 1.6 M in hexanes (2.2 ml, 1.2 equiv.) and the mixture was stirred at −78° C. for 15 min. Tri-isopropyl borate (0.97 ml, 1.4 equiv.) was added and the reaction mixture was warmed to r.t. After addition of 2N HCl, the product was extracted in EtOAc, dried over Na₂SO₄ and concentrated to yield a solid. This solid was washed with ether:hexane 1:1 to yield 679 mg of pure material.

¹H NMR (Acetone-d₆:DMSO-d₆) δ5.27 (2H, s), 7.22 (1H, dd), 7.33 (1H, dd), 7.40 (3H, m), 7.54 (2H, d), 7.63 (2H, s), 7.72 (1H, d), 7.83 (1H, d), 7.90 (1H, d), 8.36 (1H, s).

Step 3: Ethyl (E)-3-(2-{[6-benzyloxy)-2-naphthyl] methyl}phenyl)-2-propenoate

A mixture of the previous boronic acid (1.05 g, 3.8 mmol), Pd(Ph₃P)₄ (185 mg), the benzylic bromide of step 2 in example 1 (1.07 g, 4.0 mmol), 2M aq. Na₂CO, (4 ml) and toluene (8 ml) was degazed and stirred at 100° C. under nitrogen for 4 h. After addition of half saturated NH₄Cl, the product was extracted in EtOAc, dried over Na₂SO₄ and concentrated. Purification by flash chromatography with EtOAc:toluene:hexane 2.5:75:25 yielded 1.17 g of the title compound as an oil.

Step 4: (E)-3-(2-{[6-(benzyloxy)-2-naphthyl] methyl}phenyl)-2-propenoic acid

The previous ester was hydrolyzed according to the procedure of step 4 of example 1 to yield the title compound.

Step 5: 5-Bromo-2-methoxybenzenesulfonamide

To 5-bromo-2-methoxybenzenesulfonyl chloride (45g; 157.6 mmol, from Lancaster Chemical) at 0° C. in THF, was added concentrated NH₄OH (42.5 mL) and the reaction mixture was brought to r.t. for 2 h. The reaction mixture was diluted with EtOAc, extracted with NaHCO₃ (2×), brine, and the organic phase was dried over MgSO₄. The solvent was removed to give the title compound.

Step 6: N-((E)-3-(2-(6-benzyloxy-2-naphthyl)methyl) phenyl)-2-propenoyl)-5-bromo-2-methoxybenzenesulfonamide (46)

To the acid from step 5 (190 mg, 0.482 mmol) in CH₂Cl₂ was added DMF (10 μL) and oxalyl chloride (60 μL) at 0° C. and the mixture was warmed to r.t. for an hour and concentrated to dryness. The resulting acid chloride was redissolved in CH₂Cl₂:THF 1:1 (10 mL) and 5-bromo-2-methoxybenzenesulfonamide (154 mg, 1.2 equiv., from step 6) and Et₃N (135 μL, 2 equiv.) were added at 0° C. The mixture was then warmed to r.t. for an hour, 0.5N HCl was added and the product was extracted in i-PrOAc, dried over Na₂SO₄ and purified by flash chromatography with EtOAc::toluene:acetic acid 20:80:1 to yield 93 mg of a white solid.

¹H NMR (CDCl₃) δ

MS (APCI, neg.) 643.3, 641.8, 640.0 (M−1), 393.2.

EXAMPLE 11

N-{(E)-3-[2-NAPHTHYLMETHYL)PHENYL)]-2-PROPENOYL}-5-BROMO-2-METHOXY-1-BENZENESULFONAMIDE (301)

Step 1: N-{(E)-3-[2-naphthylmethyl)phenyl)]-2-propenoyl}-5-bromo-2-methoxy-1-benzenesulfonamide (301)

The carboxylic acid (400 mg; 1.22 mmol) of example 3 step 2 was coupled with 5-bromo-2-methoxy-1-benzenesulfonyl chloride according to the procedure of step 5 in example 1 to yield 284 mg of the title compound.

¹H NMR (acetone-d₆-DMSO-d₆) δ3.85 (3H, s), 4.31 (2H, s), 6.65 (1H, d), 7.15 (1H, d), 7.3 (1H, m), 7.35–7.50 (4H, m), 7.55–7.65 (2H, m), 7.7–7.9 (5H, m) and 8.01 (1H, d).

The acid was converted to the sodium salt with 1 equivalent of NaOH.

Elemental analysis calcd. for $C_{27}H_{21}BrNNaO_4S \cdot 1/2H_2O$: C, 57.15; H,3.88; N, 2.47; Found: : C, 56.88; H, 3.73; N, 2.52.

EXAMPLE 12

N-{(E)-3-[5-CHLORO-2-(2-NAPHTHYLMETHYL)PHENYL]-2-PROPENOYL}-2-THIOPHENESULFONAMIDE (303)

Step 1: 5-chloro-2-methylbenzaldehyde

To a solution of 2-bromo-4-chlorotoluene (20.0 g; 97.3 mmol) in 300 mL of THF at −78° C. was added dropwise a 2.5 M solution of n-BuLi (102.2 mmol). After 30 min of stirring at that temperature, 1-formylpiperidine (11.4 mL) in 10 mL of THF was added and the solution left for 1 h. It was brought to 0° C., quenched with NH₄OAc (25%) and diluted with EtOAc. The organic phase was dried over Na₂SO₄, filtered and the solvent removed to yield 13.3 g of the title compound.

¹H NMR (CDCl₃) δ2.6 (3H, s), 7.15 (1H, d), 7.4 (1H, d), 7.75 (1H, s) and 10.2 (1H, s).

Step 2: Ethyl (E)-3-(5-chloro-2-methylphenyl)-2-propenoate

The previous aldehyde (13.3 g; 86.0 mmol) was converted to the ethyl cinnamate according to step 1 of example 1 to yield 16.67 g.

$^1$H NMR (CDCl$_3$) δ1.2 (3H, t), 2.26 (3H, s), 4.15 (2H, q), 6.21 (1H, d), 6.99 (1H, d), 7.13 (2H, m), 7.39 (1H, s) and 7.73 (1H, d).

Step 3: Ethyl (E)-3-[2-(bromomethyl)-5-chlorophenyl]-2-propenoate

The previous ester (16.66 g; 74.1 mmol) was converted to the benzylic bromide according to step 2 of example 1 to yield 9.0 g of the title compound.

$^1$H NMR (CDCl$_3$) δ1.2 (3H, t), 4.25 (2H, q), 4.5 (2H, s), 6.4 (1H, d), 7.28 (2H, s), 7.55 (1H, s) and 7.95 (1H, d).

Step 4: Ethyl (E)-3-[5-chloro-2-(2-naphthylmethyl)phenyl]-2-propenoate

The previous benzylic bromide was coupled in a Suzuki type reaction with 2-naphthylboronic acid according to step 3 of example 1 to yield 1.14 g of the title compound.

$^1$H NMR (CDCl$_3$) δ1.15 (3H, t), 4.09 (2H, q), 4.12 (2H, s), 6.2 (1H, d), 7.03 (1H, d), 7.15 (2H, m), 7.3 (2H, m), 7.37 (1H, s), 7.45 (1H, s), 7.65 (3H, m) and 7.87 (1H, d).

Step 5: (E)-3-[5-chloro-2-(2-naphthylmethyl)phenyl]-2-propenoic acid

The hydrolysis of the previous ester (1.14 g) was done according to Step 4 of example 1 to yield 0.99 g of the title compound.

$^1$H NMR (CDCl$_3$) δ4.23 (2H, s), 6.31 (1H, d), 7.12 (1H, d), 7.22 (1H, m), 7.3 (1H, m), 7.42 (2H, m), 7.48 (1H, s), 7.59 (1H, s), 7.75 (3H, m) and 8.05 (1H, d).

Step 6: N-{(E)-3-[5-chloro-2-(2-naphthylmethyl)phenyl]-2-propenoyl}-2-thiophenesulfonamide (303)

The coupling reaction of the previous acid (400 mg; 1.22 mmol) was done according to step 6 of example 1 to yield 272 mg of the title compound.

$^1$H NMR (acetone-d$_6$) δ4.25 (2H, s), 6.58 (1H, d), 7.0 (1H, t), 7.23 (2H, m), 7.33 (1H, m), 7.39 (2H, m), 7.5–7.6 (2H, m), 7.55 (5H, m) 7.86 (1H, m) and 8.04 (1H, d).

The product was converted to the sodium salt with 1 equivalent of NaOH.

Elemental analysis calcd. for C$_{24}$H$_{17}$ClNNaO$_3$S$_2$.1/2H$_2$O: C, 57.76; H,3.64; N, 2.81; S, 12.84; Found:: C, 57.78; H, 3.62; N, 2.86; S, 12.85.

EXAMPLE 13

(E)-3-{4-CHLORO-2-[6-FLUORO-2-NAPHTHYL)METHYL]PHENYL}-2-PROPENOIC ACID SODIUM SALT (457)

Step 1: Ethyl (E)-3-(5-chloro-2-methylphenyl)-2-propenoate

To 2-bromo-4-chloro toluene (20.0 g; 97.3 mmol) in 300 mL of THF at −78° C. was added n-BuLi 2.5M (40.8 mL) dropwise. After 20 min. 1-formylpiperidine (11.4 mL; 103.0 mmol) in 10 mL of THF was added dropwise. After 30 min the reaction mixture was brought to 0° C. and quenched with HCl (10%) and diluted with EtOAc. The organic phase was collected, dry and the solvent evaporated to yield 13.3 g (89%) of 5-chloro-2-methylbenzaldehyde. This crude aldehyde was mixed with 1.1 equivalent of triethyl phosphonoacetate in THF. Sodium hydride 80% (1.3 equivalent ) was added portionwise and 1 h later the reaction was quenched with 25% NH$_4$Cl. The reaction mixture was diluted with EtOAc and the organic phase collected, dried and the solvent removed. The crude oil was purified on a short pad of silica gel using 5% EtOAc in hexane to afford 16.67 g of the title compound.

Alternatively, this procedure can be done in one reaction vessel. At the end of the first step, the flask is brought to rt and the phosphonoacetate in THF is added.

$^1$H NMR (CDCl3) δ1.21 (3H, t), 2.27 (3H, s), 4.15 (2H, q), 6.22 (1H, d), 6.95–7.15 (3H, m), 7.40 (1H, s) and 7.75 (1H, d).

Step 2: Ethyl(E)-3-[2-(bromomethyl)-5-chlorophenyl]-2-propenoate

The bromination was done according to step 2 of example 1 to provide the title compound in 45% yield.

$^1$H NMR (CDCl$_3$) δ1.32 (3H, t), 4.27 (2H, q), 4.52 (2H, s), 6.43 (1H, d), 7.30 (2H, S), 7.55 (1H, s) and 7.93 (2H, d).

Step 3: 6-Fluoro-2-naphthol

A solution of 2-(4-fluorophenyl)acetyl chloride (5.0g; 29 mmol) in CH$_2$Cl$_2$ was added to AlCl$_3$ (7.73g;58 mmol) in CH$_2$Cl$_2$ at −20° C. over 30 min. Trimethylsilyl acetylene (9.9g; 101.43 mmol) was added also over 30 min and stirred at −10° C. for 1h. The mixture was poured in ice and extracted with EtOAc. The organic phase was washed with water, NaHCO$_3$ and brine. After purification by gel silica chromatography (10% EtOAc in hexane) 2.43 g (36%) of 3-(trimethylsilyl)-6-chloro-2-naphthol was collected. The desylilation was done with TFA in CH$_2$Cl$_2$ at rt overnight. Purification by gel silica chromatography (10% EtOAc in hexane) afforded the title compound in 69% yield.

$^1$H NMR (CDCl$_3$) δ7.10–7.20 (3H, m), 7.37 (1H, dd) and 7.65 (2H, m).

Step 4: Ethyl (E)-3-{4-chloro-2-[(6fluoro-2-naphthyl)methyl]phenyl}-2-propenoate The naphthol of Step 3 was converted to the triflate with triflic anhydride/pyridine in CH$_2$Cl$_2$ at 0° C. This was coupled with the organozinc of the benzyl bromide of step 2 in example 13, with dppf and Pd(dba)$_2$. This yielded the title compound in 47% yield after purification by silica gel chromatography (10% EtOAc in hexane).

$^1$H NMR (CDCl$_3$) δ1.25 (3H, t), 4.20 (2H, q), 6.30 (1H, d), 7.10–7.27 (4H, m), 7.38 (1H, dd), 7.48 (1H, s), 7.57 (1H, dd), 7.66 (2H, m) and 7.95 (1H, d).

Step 5: (E)-3-{4-Chloro-2-[(6-fluoro-2-naphthyl)methyl]phenyl}-2-propenoic acid, sodium salt The hydrolysis of the ester of Step 4 (1.03 g; 2.7 mmol) was done according to step 4 of example 1 to yield 800 mg (87%) of the title compound. The sodium salt was prepared with 1N NaOH.

$^1$H NMR (CDCl3) δ4.21 (2H, s), 6.30 (1H, d), 7.10–7.40 (4H, m), 7.38 (1H, dd), 7.45 (1H, s), 7.58 (1H, d), 7.68 (2H, m) and 8.05 (1H, d).

LRMS for M−1=339.

EXAMPLE 14

5-BROMO-N((E)-3-{5-CHLORO-2-[(6-FLUORO-2-NAPHTHYL-2)METHYL]PHENYL}-2-PROPENOYL)-2-METHOXYBENZENESULFONAMIDE SODIUM SALT (378)

Step 1: 5-Bromo -N-((E)-3-{5-chloro-2-[(6-fluoro-2-naphthyl)methyl]phenyl}-2-propenoyl)-2-methoxybenzenesulfonamide The coupling reaction of the acid of Example 1 Step 5 with 5-bromo-2-methoxybenzesulfonamide (500 mg; 1.47 mmol) was done according to step 5 of example 1 to yield 662 mg (77%) of the title compound. The sodium salt was prepared with 1N NaOH.

1H NMR (DMSO-d6) δ3.78 (3H, s), 4.22 (2H, s), 6.53 (1H, d), 7.17 (1H, d), 7.27 (1H, d), 7.35 (2H, m), 7.47 (1H, dd), 7.51 (1H, s), 7.58 (1H, d), 7.64 (1H, dd) and 7.75–7.90 (5H, m).

LRMS for M−1=588.

EXAMPLE 15

(E)-3-{5-CHLORO-2-[(6-CHLORO-2-NAPHTHYL)METHYL]PHENYL}-2-PROPENOIC ACID SODIUM SALT (469)

Step 1: 6-Chloro-2-naphthol

The title compound was prepared from 2-(4-fluorophenyl)acetyl chloride according to step 3 of example 13.

$^1$H NMR (CDCl$_3$) δ7.10 (2H, m), 7.34 (1H, dd), 7.55–7.67 (2H, m) and 7.72 (1H, s).

Step 2: Ethyl (E)-3-{5-chloro-2-[(6-chloro-2-naphthyl)methyl]phenyl}-2-propenoate The title compound was prepared according to step 4 of example 13 in 30% yield.

$^1$H NMR (CDCl$_3$) δ1.23 (3H, t), 4.20 (4H, m), 6.29 (1H, d), 7.10 (1H, d), 7.22 (2H, m), 7.33 (1H, dd), 7.42 (1H, s), 7.53 (1H, d), 7.61 (2H, d), 7.70 (1H, s) and 7.91 (1H, d).

Step 3: (E)-3-{5-Chloro-2-[(6-chloro-2-naphthyl)methyl]phenyl}-2-propenoic acid sodium salt The hydrolysis of the ester of Step 2 (620 mg; 1.6 mmol) was done according to step 4 of example 1 to yield 500mg (87%) of the title compound.

$^1$H NMR (CDCl$_3$) δ4.22 (2H, s), 6.30 (1H, d), 7.15 (1H, d), 7.20–7.39 (3H, m), 7.43 (1H, s), 7.56 (1H, s), 7.62 (2H, t), 7.75 (1H, s) and 8.02 (1H, d).

Elemental analysis calcd for $C_{20}H_{13}Cl_2NaO_2 \cdot H_2O$: C, 60.48; H, 3.78; Found C, 60.68, H, 3.63.

EXAMPLE 16

5-BROMO-N((E)-3-{5-CHLORO-2-[(6-CHLORO-2-NAPHTHYL-2)METHYL]PHENYL}-2-PROPENOYL)-2-METHOXYBENZENESULFONAMIDE, SODIUM SALT (450)

Step 1: 5-Bromo-N-((E)-3-{5-chloro-2-[(6-chloro-2-naphthyl)methyl]phenyl}-2-propenoyl)-2-methoxybenzenesulfonamide The coupling reaction of the acid of Example 15 Step 3 (500 mg; 1.4 mmol) was done according to step 5 of example 1 with 5-bromo-2-methoxybenzesulfonamide to yield 662 mg (74%) of the title compound. The sodium salt was prepared with 1N NaOH.

1H NMR (DMSO-d6) δ3.78 (3H, s), 4.22 (2H, s), 6.53 (1H, d), 7.20 (1H, d), 7.30–7.40 (2H, m), 7.45 (2H, m), 7.55 (1H, s), 7.59 (1H, s), 7.79 (3H, m), 7.85–7.92 (2H, m) and 7.98 (1H, d).

Elemental analysis calcd for C27H19BrCl2NNaO4S . 2H2O: C, 49.01; H, 3.33; N, 2.14; Found C, 48.89, H, 3.47; N, 2.11.

EXAMPLE 17

(E)-3-(5-CHLORO-2-{[6-DIFLUOROMETHOXY)-2-NAPHTHYL]METHYL}PHENYL-2-PROPENOIC ACID, SODIUM SALT (505)

Step 1: 6-Bromo-2-difluoromethoxynaphthalene

Methyl chlorodifluoroacetate (5.3 mL) was added dropwise to 6-bromonaphthol (10.25 g; 45.9 mmol) and potassium carbonate (7.61g; 55.1 mmol) at 90 C in 160 mL of DMF for 6 h. Purification by gel silica chromatography (3% EtOAc in hexane) gave 4.80 g (38%) of the title compound.

1H NMR (CDCl3) δ6.61 (1H, t), 7.31 (1H,dd), 7.48 (1H, d), 7.56 (1H, dd), 7.67 (1H, d), 7.72 (1H, d) and 8.01 (1H, d).

Step 2: Ethyl (E)-3-(5-chloro-2-{[6-difluoromethoxy)-2-naphthyl]methyl}phenyl)-2-propenoate The corresponding boronic acid of the previous halide was coupled according to step 3 of example 1 of the title compound in 57% yield.

1H NMR (CDCl3) δ1.25 (3H, t), 4.22 (4H, m), 6.28 (1H, d), 6.53 (1H, t), 7.11 (1H, d), 7.25 (2H, m), 7.45 (2H, d), 7.55 (1H, d), 7.72 (2H, t) and 7.92 (1H, d).

Step 3: (E)-3-(5-Chloro-2-{[6-difluoromethoxy)-2-naphthyl]methyl}phenyl)-2-propenoic acid sodium salt The hydrolysis of the ester of Step 2 (1.9 g; 4.7 mmol) was done according to step 4 of example 1 to yield 600mg of the title compound.

1H NMR of sodium salt (DMSO-d6) δ4.20 (2H, s), 6.29 (1H, d), 7.10–7.40 (6H, m), 7.58 (3H, m) and 8.84 (2H, t).

HRMS calc'd for $C_{21}H_{14}O_3F_2ClNa$ +H=411.0575; Found: 411.0577.

EXAMPLE 18

5-BROMO-N-[(E)-3-(5-CHLORO-2-{[6-DIFLUOROMETHOXY)-2-NAPHTHYL_METHYL)-2-PROPENOYL]-2-METHOXYBENZENESULFONAMIDE, SODIUM SALT (447)

Step 1: 5-Bromo -N-[(E)-3-(5-chloro-2-{[6-difluoromethoxy)-2-naphthyl]methyl}phenyl)-2-propenoyl]-2-methoxybenzennesulfonamide The coupling reaction of the acid of Example 17 Step 3 (1.00 g; 2.57 mmol) was done according to step 5 of example 1 with 5-bromo-2-methoxybenzesulfonamide to yield 915 mg (56%) of the title compound. The sodium salt was prepared with 1N NaOH.

1H NMR of sodium salt DMSO-d6) δ3.66 (3H, s), 4.18 (2H, s), 6.36 (1H, d), 6.92 (1H, d), 7.20–7.35 (5H, m), 7.48 (2H, m), 7.55–7.65 (3H, m) and 7.80 (3H, m).

LRMS for M−1=634.

EXAMPLE 19

(E)-3-[2-(3,4-DICHLOROBENZYL)-5-CHLOROPHENYL]-2-PROPENOIC ACID, SODIUM SALT (535)

Step 1: Ethyl (E)-3-[2-(3 ,4-dichlorobenzyl)-5-chlorophenyl)-2-propenoate

The benzyl bromide of step 2 of example 13 was treated with 3,4-dichlorobenzeneboronic acid according to the procedure described in step 3 of example 1 to yield the title compound in 67% yield.

1H NMR (CDCl3) δ1.30 (3H, t), 4.00 (2H, s), 4.23 (2H, q), 6.30 (1H, d), 6.90 (1H,dd), 7.09 (1H, d), 7.15 (1H, s), 7.28 (1H, m), 7.32 (1H, d), 7.55 (1H, d) and 7.79 (1H, d).

Step 2: (E)-3-[2-(3,4-Dichlorobenzyl)-5-chlorophenyl)-2-propenoic acid, sodium salt The hydrolysis of the ester of Step 1 (1.00 g; 2.7 mmol) was done according to step 4 of example 1 to yield 907 mg (98%) of the title compound.

1H NMR (CDCl3) δ3.95 (2H, s), 6.30 (1H, d), 6.86 (1H, d), 7.08 (2H, m), 7.32 (2H, m), 7.55 (1H, s) and 7.90 (1H, d).

LRMS for M−1=339.

EXAMPLE 20

5-BROMO-N-{(E)-3-[5-CHLORO-2-(3,4-DICHLOROBENZYL)PHENYL]-2-PROPENOYL}-2-METHOXYBENZENESULFONAMIDE, SODIUM SALT (421)

Step 1: 5-Bromo-N-{(E)-3-[5-chloro-2-)3,4-dichlorobenzyl)phenyl]-2-propenoyl}-2-methoxybenzenesulfonamide The coupling reaction of the acid of Example 19 Step 2 (0.600 g; 1.75 mmol) was done according to step 5 of example 1 with 5-bromo-2-methoxybenzesulfonamide to yield 548 mg (53%) of the title compound. The sodium salt was prepared with 1N NaOH.

1H NMR (DMSO-d6) δ3.85 (3H, s), 4.10 (2H, s), 6.54 (1H, s), 7.01 (1H, d), 7.22 (1H, d), 7.32 (2H, m), 7.40–7.50 (2H, m), 7.56 (1H, s), 7.67 (1H, d), 7.86 (1H, d), 7.91 (1H, s) and 12.37 (1J, s).

LRMS for M−1−586.

EXAMPLE 21

5-BROMO-N-{(E)-3-[4-CHLORO-2-(2-NAPHTHYLMETHYL)PHENYL]-2-PROPENOYL}-2-METHOXYBENZENESULFONAMIDE, SODIUM SALT (449)

Step 1: Ethyl (E)-3-{4-chloro-2-[(2-naphthylmethyl)phenyl}-2-propenoate

2-Bromo-5-chloro toluene (20.0 g) was converted to the corresponding aldehyde and then to the cinnamate according to step 1 of example 13. This cinnamate was converted to the benzylic bromide according to step 2 of example 1 and coupled via a Suzuki coupling reaction according to step 3 of example 1 with naphthalene boronic acid to yield the title compound.

$^1$H NMR (CDCl$_3$) δ1.30 (3H, t), 4.22 (4H, m), 6.29 (1H, d), 7.15–7.27 (3H, m), 7.42 (2H, m), 7.52 (2H, m), 7.75 (3H, m) and 7.99 (1H, d).

Step 2: (E)-3-{4-Chloro-2-[(2-naphthylmethyl)phenyl}-2-propenoic acid (530)

The hydrolysis of the ester of Step 1 (0.56 g; 1.57 mmol) was done according to step 4 of example 1 to yield 450 mg (88%) of the title compound.

$^1$H NMR (CDCl$_3$) δ4.24 (2H, s), 6.30 (1H, d), 7.20–7.30 (3H, m), 7.42 (2H, m), 7.51 (2H, m), 7.75 (3H, m) and 8.09 (1H, d).

LRMS for M−1=321.

Step 3: 5-Bromo-N-{[(E)-3-[4-chloro-2-(2-naphthylmethyl)phenyl]propenoyl}-2-methoxybenzenesulfonamide The coupling reaction of the acid of Step 2 (0.296 g; 0.89 mmol) was done according to step 5 of example 1 with 5-bromo-2-methoxybenzesulfonamide to yield 213 mg (42%) of the title compound. The sodium salt was prepared with 1N NaOH.

$^1$H NMR (ACETONE-MEOH-d$_6$) δ3.70 (3H, s), 4.20 (2H, s), 6.44 (1H, d), 6.95 (2H, m), 7.25 (3H, m), 7.40 (2H, m), 7.55 (3H, m), 7.75 (3H, m), 7.95 (1H, d) and 8.02 (1H, d).

LRMS for M−1=568.

EXAMPLE 22

(E)-3-[5-METHOXY-2-(2-NAPHTHMETHYL)PHENYL]-2-PROPENOIC ACID, SODIUM SALT (534)

Step 1: (2-Bromo-4-methoxyphenyl)(2-naphthyl)methanone

AlCl$_3$ (17.48 g; 131.1 mmol) was added portionwise to a mixture of 3-bromocresol (16.04 g; 87.4 mmol) and 2-naphthoyl chloride (25.00 g; 131.1 mmol) in 50 mL of CHCl3 gave 14.0 g (47%) of the title compound.

1H NMR (CDCl3) δ3.78 (3H, s), 6.92 (1H, dd), 7.19 (1H, d), 7.38 (1H, d), 7.50 (1H, t), 7.59 (1H, t), 7.89 (3H, m), 7.95 (1H, dd) and 8.18 (11H, s).

Step 2: 2-(2-Bromo-4-methoxybenzyl)naphtalene

To the methanone of Step 1 (14.0 g) and triethylsilane (15 mL) in 15 mL of CHCl$_3$ was added TFA and was heated to 50° C. overnight. The solution was cooled and quenched with NaOH (2N) to provide the title compound in 82% yield.

1H NMR (CDCl3) δ3.75 (3H, s), 4.20 (2H, s), 6.75 (1H, dd), 7.07 (1H, d), 7.12 (1H, s), 7.30 (1H, d), 7.42 (2H, m), 7.58 (1H, s) and 7.76 (3H, m).

Step 3: Ethyl (E)-3-[5-methoxy-2-(2-naphthylmethyl)phenyl]-2-propenoate

The naphthalene of Step 2 was converted to the corresponding aldehyde according to the step 1 of example 13 in 98% yield. This aldehyde was then converted to the cinnamate according to step 1 of example 13 in 90% yield.

1H NMR (CDCl3) δ3.70 (3H, s), 4.11 (4H, m), 6.20 (1H, d), 6.77 (1H, dd), 6.99 (1H, d), 7.03 (1H, d), 7.15 (1H, d), 7.30 (2H, m), 7.39 (1H, s), 7.60–7.70 (3H, m) and 7.90 (1H, s).

Step 4: (E)-3-[5-Methoxy-2-(2-naphthmethyl)phenyl]-2-propenoic acid

The hydrolysis of the ester of Step 3 (2.83 g; 8.2 mmol) was done according to step 4 of example 1 to yield 2.16 g (83%) of the title compound. The sodium salt was prepared with 1N NaOH.

1H NMR (CDCl3) δ3.70 (3H, s), 4.13 (2H, s), 6.20 (1H, d), 6.80 (1H, dd), 7.02 (2H, m), 7.15 (1H, d), 7.29 (2H, m), 7.39 (1H, s), 7.62 (3H, m) and 8.03 (1H, d).

LRMS calcd for M−1=317.

EXAMPLE 23

5-BROMO-2-METHOXY-N-{(E)-3-[5-METHOXY-2-(2-NAPHTHYLMETHYL)PHENYL]-2-PROPENOYL}BENZENESULFONAMIDE SODIUM SALT (448)

Step 1: 5-Bromo-2-methoxy-N-{(E)-3-[5-methoxy-2-(2-naphthylmethyl)phenyl]-2-propenoyl}benzenesulfonamide The coupling reaction of the acid of Example 22 Step 4 (0.600 g; 1.88 mmol) was done according to step 5 of example 1 with 5-bromo-2-methoxybenzesulfonamide to yield 573 mg (57%) of the title compound. The sodium salt was prepared with 1N NaOH.

1H NMR (CDCl3) δ3.72 (3H, s), 3.77 (3H, s), 4.13 (2H, s), 6.40 (1H, d), 6.70 (1H, d), 6.85 (1H, dd), 7.02 (1H, d), 7.10–7.20 (2H, m), 7.37 (3H, m), 7.57 (1H, dd), 7.60–7.80 (3H, m),7.95 (1H, d), 8.15 (1H, d) and 9.12 (1H, broad s).

LRMS calcd for M−1=564.

EXAMPLE 24

(E)-3-[5-CHLORO-2-(4-CHLOROBENZYL)PHENYL]-2-PROPENOIC ACID SODIUM SALT (537)

Step 1: Ethyl(E)-3-[5-chloro-2-(4-chlorobenzyl)phenyl]-2-propenoate

The benzyl bromide of step 2 of example 13 was coupled in a Suzuki coupling reaction with 4-chlorobenzene boronic acid according to the procedure of step 2 example 1 to yield 69% of the title compound.

1H NMR (CDCl3) δ1.30 (3H, t), 4.02 (2H, s), 4.22 (2H, q), 6.29 (1H, d), 6.99 (2H, d), 7.08 (1H, d), 7.20–7.30 (3H, m), 7.52 (1H, s) and 7.83 (1H, d).

Step 2: (E)-3-[5-Chloro-2-(4-chlorobenzyl)phenyl]-2-propenoic acid

The hydrolysis of the ester of Step 1 (1.14 g; 3.4 mmol) was done according to step 4 of example 1 to yield 860 mg (83%) of the title compound. The sodium salt was prepared with 1N NaOH.

1H NMR (CDCl3) δ4.04 (2H, s), 6.30 (1H, d), 7.00 (2H, d), 7.10 (1H, d), 7.23 (2H, d), 7.29 (1H, d), 7.55 (1H, s) and 7.95 (1H, d).

LRMS calcd for M−1=305.

EXAMPLE 25

(E)-3-{2-[(5-(PHENYLMETHOXY)INDOLYL) METHYL]-5-FLUOROPHENYL}-N-[(5-BROMO-2-METHOXYPHENYL)SULFONYL]-2-PROPENAMIDE (451)

Step 1: Ethyl (E)-3-(5-fluoro-2-methylphenyl)-2-propenoate

5-Fluoro-2-methylbenzaldehyde (40.58 g; 294 mmol) was converted to the ethyl cinnamate according to step 1 of example 1 to yield 40.81 g. of the title compound.

$^1$H NMR (acetone-$d_6$) δ1.29 (3H, t), 2.40 (3H, s), 4.23 (2H, q), 6.49 (1H, d), 7.07 (1H, td), 7.29 (1H, dd), 7.46 (1H, dd) and 7.87 (1H, dd).

Step 2: Ethyl (E)-3-[2-(bromomethyl)-5-fluorophenyl]-2-propenoate

The ester of Step 1(40.80 g; 196 mmol) was converted to the benzylic bromide according to step 2 of example 1 to yield 24.17 g of the title compound.

$^1$H NMR (acetone-$d_6$) δ1.30 (3H, t), 4.24 (2H, q), 4.81 (2H, s), 6.62 (1H, d), 7.18 (1H, td), 7.58 (2H, m) and 8.02 (1H, dd).

Step 3: Ethyl (E)-3-{2-[(5-(phenylmethoxy)indolyl) methyl]-5-fluorophenyl}-2-propenoate The benzylic bromide of Step 2 (3.16 g; 11.0 mmol) was coupled with 5-(phenylmethoxy)indole according to the same procedure described in step 1 of example 2 to yield 2.27 g of the title compound.

$^1$H NMR (acetone-$d_6$) δ1.27 (3H, t), 4.20 (2H, q), 5.11 (2H, s), 5.59 (2H, s), 6.43 (1H, dd), 6.52 (1H, d), 6.80 (1H, dd), 6.86 (1H, dd), 7.08 (11H, td), 7.19 (1H, d), 7.22 (1H, d), 7.31 (2H, m), 7.38 (2H, m), 7.50 (2H, m), 7.55 (1H, dd) and 8.01 (1H, dd).

Step 4: (E)-3-{2-[(5-(Phenylmethoxy)indolyl)methyl]-5-fluorophenyl}-2-propenoic acid (493)

The hydrolysis of the ester of Step 3 (2.27 g) was done according to step 4 of example 1 to yield 2.07 g of the title compound.

$^1$H NMR (acetone-$d_6$) δ5.11 (2H, s), 5.62 (2H, s), 6.43 (1H, dd), 6.53 (1H, d), 6.75 (1H, dd), 6.86 (1H, dd), 7.08 (1H, td), ), 7.19 (1H, d), 7.25 (1H, d), 7.31 (2H, m), 7.38 (2H, m), 7.50 (2H, m), 7.56 (1H, dd) and 8.04 (1H, dd).

Elemental analysis calcd. for $C_{25}H_{20}FNO_3.2H_2O$: C, 68.64; H, 5.53; N, 3.20; Found: C, 68.16; H, 4.95; N, 3.06.

Step 5: (E)-3-{2-[(5-(Phenylmethoxy)indolyl)methyl]-5-fluorophenyl}-N-[(5-bromo-2-methoxyphenyl)sulfonyl]-2-prop enamide The acid of Step 5 (2.06; 5.13 mmol) was coupled with 5-bromo-2-methoxybenzenesulfonamide of example 10, step 5 according to step 5 of example 1 to yield 2.44 g of the title compound.

$^1$H NMR (acetone-$d_6$) δ3.93 (3H, s), 5.10 (2H, s), 5.59 (2H, s), 6.39 (1H, dd), 6.73 (1H, dd), 6.78 (1H, d), 6.81 (1H, dd), 7.09 (1H, td), ), 7.18 (1H, d), 7.24 (3H, m), 7.32 (1H, m), 7.39 (3H, m), 7.49 (2H, m), 7.82 (1H, dd), 8.01 (1H, dd) and 8.09 (1H, d).

Elemental analysis calcd. for $C_{32}H_{26}BrFN_2O_5S_2$: C, 59.17; H, 4.03; N, 4.31; S, 4.94; Found: C, 59.07; H, 4.01; N, 4.34; S, 5.16.

EXAMPLE 26

(E)-3-[2-(BENZO[B]THIOPHEN-2-YLMETHYL)-5-FLUOROPHENYL]-N-[(5-BROMO-2-METHOXYPHENYL)SULFONYL]-2-PROPENAMIDE SODIUM SALT (452)

Step 1: Ethyl (E)-3-[2-(benzo[b]thiophen-2ylmethyl) fluorophenyl]-2-propenoate

The ester (901 mg, 3.14 mmol) of example 13, step 2 was coupled with benzo[b]thiophene-2-boronic acid (from Lancaster Chemical) in DME according to the same procedure described in step 3 of example 10 to yield 657 mg of the title compound.

$^1$H NMR (acetone-$d_6$) δ1.22 (3H, t), 4.16 (2H, q), 4.43 (2H, s), 6.50 (1H, d), 7.03 (1H, s), 7.15–7.35 (3H, m), 7.47 (1H, dd), 7.56 (1H, dd), 7.69 (1H, dd), 7.78 (1H, dd) and 8.00 (1H, dd).

Step 2: (E)-3-[2-(benzo[b]thiophen2ylmethyl) 5fluorophenyl]-2-propenoic acid (539)

The hydrolysis of the ester of Step 1 (657 mg) was done according to step 4 of example 1 to yield 345 mg of the title compound.

$^1$H NMR (acetone-$d_6$) δ4.45 (2H, s), 6.51 (1H, d), 7.04 (1H, d), 7.2–7.3 (3H, m), 7.49 (1H, dd), 7.57 (1H, dd), 7.70 (1H, d), 7.80 (1H, m) and 8.01 (1H, dd).

Elemental analysis calcd. for $C_{18}H_{13}FO_2S$: C, 69.21; H, 4.19; Found: C, 68.96; H, 4.15.

Step 3: (E)-3-[2-(Benzo[b]thiophen-2-ylmethyl)-5-fluorophenyl]-N-[(5-bromo-2-propenamide The previous acid (264 mg; 0.85 mmol) was coupled with 5-bromo-2-methoxybenzenesulfonamide of example 10, step 5 according to step 5 of example 1 to yield 287 mg of the title compound.

$^1$H NMR (acetone-$d_6$) δ3.83 (3H, s), 4.43 (2H, s), 6.77 (1H, d), 7.00 (1H, d), 7.13 (1H, d), 7.2–7.3 (3H, m), 7.41 (1H, dd), 7.49 (1H, dd), 7.65 (1H, dd), 7.78 (2H, m), 7.96 (1H, dd)HH and 8.05 (1H, d).

The acid was converted to the sodium salt with 1 equivalent of NaOH.

Elemental analysis calcd. for $C_{25}H_{18}BrFNNaO_4S_2.H_2O$: C, 50.01; H, 3.36; N, 2.33; Found: C, 49.84; H, 3.22; N, 2.41.

EXAMPLE 27

N-(E)-[(5-BROMO-2-METHOXYPHENYL) SULFONYL]-3-(5-FLUORO-2-{[1-BENZYLINDOL-5-YL]METHYL}PHENYL)-2-PROPENAMIDE SODIUM SALT (453)

Step 1: Ethyl (E)-3-[5-fluoro-2(indol-5-ylmethyl)phenyl]-2-propenoate

The ester (1.83 g, 6.37 mmol) of example 13, step 2 was coupled with 5-indolyl boronic acid and NaHCO$_3$ in DME according to the procedure described in step 3 of example 10 to yield 1.08 g of the title compound.

$^1$H NMR (acetone-$d_6$) δ1.26 (3H, t), 4.17 (2H, q), 4.21 (2H, s), 6.37 (1H, m), 6.44 (1H, d), 6.94 (1H, dd), 7.14 (1H, td), 7.27–7.37 (4H, m), 7.51 (1H, dd), 8.05 (1H, dd) and 10.13 (1H, s).

Step 2: Ethyl (E)-3-(5-fluoro-2-{[1-benzylindol-5-yl] methyl}phenyl)-2-propenoate The indole of Step 1 (621 mg; 1.92 mmol) was coupled with benzyl bromide according to the procedure described in step 1 of example 2 to yield 678 mg of the title compound.

$^1$H NMR (acetone-$d_6$) δ1.26 (3H, t), 4.17 (4H, m), 5.32 (2H, s), 6.43 (2H, m), 6.95 (1H, dd), 7.1–7.4 (11H, m), 7.49 (1H, dd) and 8.08 (1H, dd).

Step 3: (E)-3-(5-Fluoro-2-{[1-benzylindol-5-yl] methyl}phenyl)-2propenoic acid) (540)

The hydrolysis of the ester of Step 2 (678 mg) was done according to step 4 of example 1 to yield 276 mg of the title compound.

$^1$H NMR (acetone-$d_6$) δ4.20 (2H, s), 5.38 (2H, s), 6.39 (1H, d), 6.45 (1H, d), 6.95 (1H, d), 7.1–7.3 (1OH, m), 7.48 (1H, d) and 8.04 (1H, dd).

Elemental analysis calcd. for $C_{25}H_{20}FNO_2$: C, 77.91; H, 5.23; N, 3.63; Found: C, 78.52; H, 5.46; N, 3.66.

Step 4: N-(E)-[(5-Bromo-2-methoxyphenyl)sulfonyl]-3-(5-fluoro-2-{[1-benzylindol-5-yl]methyl}phenyl)-2-propenamide The acid of Step 3 (219 mg; 0.57 mmol) was coupled with 5-bromo-2-methoxybenzenesulfonamide of example 10, step 5 according to step 5 of example 1 to yield 149 mg of the title compound.

$^1$H NMR (acetone-$d_6$) δ3.82 (3H, s), 4.18 (2H, s), 5.38 (2H, s), 6.36 (1H, dd), 6.72 (1H, d), 6.90 (1H, dd), 7.1-7.4 (12H, m), 7.78 (1H, dd), 7.98 (1H, dd) and 8.05 (1H, d).

The acid was converted to the sodium salt with 1 equivalent of NaOH.

Elemental analysis calcd. for $C_{32}H_{25}BrFN_2NaO_4S.1/2H_2O$: C, 57.84; H, 3.94; N, 4.22; Found: C, 57.61; H, 3.86; N, 4.16.

EXAMPLE 28

N-(E)-[(2,4-DIMETHYL(1,3-THIAZOL-5-YL))SULFONYL]-3-{3-[(5-CHLOROINDOLYL)METHYL](2-PYRIDYL)}-2-PROPENAMIDE (444)

Step 1: Ethyl (E)-3-(3-methyl-2-pyridyl)-2-propenoate

To a solution of 2-bromo-3-methylpyridine (10.36 g; 60.2 mmol) in 120 mL of THF at −100° C. was added dropwise a 1.6 M solution of n-BuLi (65.6 mmol). After 20 min of stirring at that temperature, 1-formylpiperidine (7.65 g) in 10 mL of THF was added and the solution was warmed to r.t.. After 30 min of stirring at r.t., triethyl phosphonoacetate (13.7 mL; 69.1 mmol) was added dropwise below 30° C. After 1 h of stirring, the mixture was quenched with $NH_4OAc$ (25%) and extracted with EtOAc. The solvent was removed and the crude oil was purified by silica gel chromatography (25% EtOAc in hexane) to yield 10.32 g of the title compound.

$^1$H NMR (acetone-$d_6$) δ1.29 (3H, t), 2.46 (3H, s), 4.22 (2H, q), 6.99 (IH, d), 7.27 (1H, dd), 7.64 (1H, dt), 7.90 (1H, d) and 8.45 (1H, m).

Step 2: Ethyl (E)-3-[3-(bromomethyl)-2-pyridyl]-2-propenoate

The ester of Step 1 (5.93 g; 31.0 mmol) was converted in benzene to the benzylic bromide according to the procedure described in step 2 of example 1 to yield 1.83 g of the title compound.

$^1$H NMR (acetone-$d_6$) δ1.30 (3H, t), 4.25 (2H, q), 4.88 (2H, s), 7.10 (1H, d), 7.41 (1H, dd), 7.91 (1H, dd), 8.03 (1H, d) and 8.60 (1H, dd).

Step 3: Ethyl (E )-3-{3-[(5-chloroindolyl)methyl]-2-pyridyl}-2-propenoate

The benzylic bromide of Step 2 (1.33 g; 4.91 mmol) was coupled with 5-chloroindole according to the procedure described in step 1 of example 2 to yield 1.22 g of the title compound.

$^1$H NMR (acetone-$d_6$) δ1.28 (3H, t), 4.22 (2H, q), 5.78 (2H, s), 6.57 (1H, d), 6.94 (1H, d), 7.04 (1H, d), 7.11 (1H, dd), 7.27 (1H, dd), 7.43 (2H, m), 7.63 (1H, d), 7.99 (1H, d) and 8.53 (1H, d).

Step 4: (E)-3-{3-[(5-Chloroindolyl)methyl]-2-pyridyl}-2-propenoic acid (542)

The hydrolysis of the ester of Step 3 (283 mg) was done according to step 4 of example 1 to yield 291 mg of the title compound.

$^1$H NMR (acetone-$d_6$) δ5.81 (2H, s), 6.57 (1H, d), 6.88 (1H, d), 7.05 (1H, d), 7.11 (1H, dd), 7.26 (1H, dd), 7.43 (2H, m), 7.63 (1H, d), 8.02 (1H, d) and 8.54 (1H, d).

Elemental analysis calcd. for $C_{17}H_{13}ClN_2O_2.1/4H_2O$: C, 64.36; H. 4.29; N. 8.83; Found: C, 64.63; H, 4.43; N, 8.65.

Step 5: N-(E)-[(2,4-Dimethyl(1,3-thiazol-5-yl))sulfonyl]-3-{3-[(5-chloroindolyl)methyl](2-pyridyl)}-2-propenamide The acid of Step 4 (283 mg; 0.90 mmol) was coupled with 2,4-dimethyl-1,3-thiazole-5-sulfonamide (from Maybridge Chemical) according to step 5 of example 1 to yield 315 mg of the title compound.

$^1$H NMR (acetone-$d_6$) δ2.64 (3H, s), 2.69 (3H, s), 5.81 (2H, s), 6.56 (1H, d), 6.84 (1H, d), 7.09 (1H, dd), 7.26 (1H, dd), 7.31 (1H, d), 7.41 (2H, m), 7.62 (1H, d), 8.05 (1H, d) and 8.51 (1H, d).

Elemental analysis calcd. for $C_{22}H_{19}ClN_4O_3S_2$: C, 54.26; H, 3.93; N, 11.50; S, 13.17; Found: C, 54.69; H, 4.03; N, 11.18; S, 12.89.

EXAMPLE 29

N-{(E)-3-[5-CHLORO-2-(2-NAPHTHYLMETHYL)PHENYL]-2-PROPENOYL-2-METHOXYBENZENESULFONAMIDE (302)

The coupling reaction of the acid (3.00 g; 9.1 mmol) of Step 5 in Example 12 was done with 5-bromo-2-methoxybenzesulfonamide (2.56 g; 9.6 mmol) according to Step 5 of Example 1 to yield 4.13 g (79%) of the title compound. The sodium salt was prepared with 1N NaOH.

$^1$H NMR (DMSO-$d_6$) δ3.76 (3H, s), 4.25 (2H, s), 6.52 (1H, d), 7.15 (1H, d), 7.26 (1H, d), 7.36 (1H, d), 7.41–7.52 (4H, m), 7.58 (1H, s), 7.69 (1H, m), 7.78 (1H, d), 7.82 (3H, m), 7.89 (1H, d) and 12.38 (1H, br s).

Elemental analysis: Calcd. for $C_{27}H_{20}BrClNNaO_4S.H_2O$: C, 53.08; H, 3.64; N, 2.29; Found: C, 53.25; H, 3.89; N, 2.91.

These intermediates were prepared according to the literature:
5-fluoro-2-methylbenzaldehyde:
Servis, K. L.; Fang, K.-N. *J. Am. Chem. Soc.* 1968, 90, 6712–6717.
5-indolyl boronic acid:
Yang, Y.; Martin, A. R. *Heterocycles* 1992, 34, 1395–1398.

What is claimed is:

1. A compound represented by formula I:

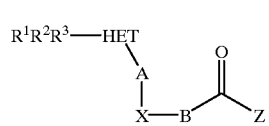

or a pharmaceutically acceptable salt, hydrate or ester thereof, wherein:

HET represents a 5–12 membered monocyclic or bicyclic aromatic ring system containing 0–3 heteroatoms selected from O, S(O)$_n$ and N(O)$_m$ wherein m is 0 or 1 and n is 0, 1 or 2;

A is a one or two atom moiety and is selected from the group consisting of: —W—, —C(O)—, —C(R$^7$)$_2$—W—, —W—C(R$^7$)$_2$—, —CR$^7$(OR$^{20}$)—, —C(R$^7$)$_2$—, —C(R$^7$)$_2$—C(OR$^{20}$)R$^7$—, —C(R$^7$)$_2$—C(R$^7$)$_2$— or —CR$^7$=CR$^7$—, wherein W represents O, S(O)$_n$ or NR$^{17}$, with n as previously defined and R$^{17}$ as defined below;

X represents a 5–10 membered monocyclic or bicyclic aryl or heteroaryl group having 1–3 heteroatoms selected from O, S(O)$_n$ and N(O)$_m$, and optionally substituted with R$^{14}$ and R$^{15}$, and A and B are attached to the aryl or heteroaryl group ortho relative to each other;

B represents —CH=CH— or 1,2-cyclopropyl;

Z is NHSO$_2$R$^{19}$;

R$^1$, R$^2$ and R$^3$ independently represent H, halogen, lower alkyl, lower alkenyl, lower alkynyl, lower alkenyl-HET (R$^a$)$_{4-9}$, —(C(R$^4$)$_2$)$_p$SR$^5$, —(C(R$^4$)$_2$)$_p$OR$^8$, —(C(R$^4$)$_2$)$_p$N(R$^6$)$_2$, CN, NO$_2$, —(C(R$^4$)$_2$)$_p$C(R$^7$)$_3$, —CO$_2$R$^9$, CON(R$^6$)$_2$ or —(C(R$^4$)$_2$)$_p$S(O)$_n$R$^{10}$, wherein p is 0–3 and n is as previously defined;

each R$^4$ is independently H, F, CF$_3$ or lower alkyl, or two R$^4$ groups are taken in conjunction and represent a ring of up to six atoms, optionally containing one heteroatom selected from O, S(O)$_n$ or N(O)$_m$;

each R$^5$ is independently lower alkyl, lower alkenyl, lower alkynyl, CF$_3$, lower alkyl-HET, lower alkenyl-HET or —(C(R$^{18}$)$_2$)$_p$Ph(R$^{11}$)$_{0-2}$;

each R$^6$ is independently H, lower alkyl, lower alkenyl, lower alkynyl, CF$_3$, Ph, Bn and when two R$^6$ groups are attached to N they may be taken in conjunction and represents a ring of up to 6 atoms, optionally containing an additional heteroatom selected from O, S(O)$_n$ or N(O)$_m$;

each R$^7$ is independently H, F, CF$_3$ or lower alkyl, and when two R$^7$ groups are presents, they may be taken in conjunction and represent an aromatic or aliphatic ring of 3 to 6 members containing from 0–2 heteroatoms selected from O, S(O)$_n$ and N(O)$_m$;

each R$^8$ represents H or R$^5$;

each R$^9$ is independently H, lower alkyl, lower alkenyl, lower alkynyl, Ph or Bn;

each R$^{10}$ is independently lower alkyl, lower alkenyl, lower alkynyl, CF$_3$, Ph(R$^{11}$)$_{0-3}$, CH$_2$Ph(R$^{11}$)$_{0-3}$ or N(R$^6$)$_2$;

each R$^{11}$ is independently lower alkyl, SR$^{20}$, OR$^{20}$, N(R$^6$)$_2$, —CO$_2$R$^{12}$, —CON(R$^6$)$_2$, —C(O)R$^{12}$, CN, CF$_3$, NO$_2$ or halogen;

each R$^{12}$ is independently H, lower alkyl or benzyl;

each R$^{13}$ is independently H, halo, lower alkyl, O-lower alkenyl, S-lower alkyl N(R$^6$)$_2$, CO$_2$R$^{12}$, CN, CF$_3$ or NO$_2$;

R$^{14}$ and R$^{15}$ are independently lower alkyl, halogen, CF$_3$, OR$^{16}$, S(O)$_n$R$^{16}$ or C(R$^{16}$)$_2$OR$^{17}$;

each R$^{16}$ is independently H, lower alkyl, lower alkenyl, Ph, Bn or CF$_3$;

each R$^{17}$ is independently H, lower alkyl or Bn;

each R$^{18}$ is independently H, F or lower alkyl, and when two R$^{18}$ groups are present, they may be taken in conjunction and represent a ring of 3 to 6 members comprising carbon atoms and optionally one heteroatom chosen from O, S(O)$_n$ or N;

each R$^{19}$ is lower alkyl, lower alkenyl, lower alkynyl, CF$_3$, HET(R$^a$)$_{4-9}$, lower alkyl-HET(R$^a$)$_{4-9}$ or lower alkenyl-HET(R$^a$)$_{4-9}$;

each R$^{20}$ is independently H, lower alkyl, lower alkenyl, lower alkynyl, CF$_3$ or Ph(R$^{13}$)$_2$ and each R$^a$ is independently selected from the group consisting of: H, OH, halo, CN, NO$_2$, amino, C$_{1-6}$alkyl, C$_{2-6}$alkenyl, C$_{2-6}$alkynyl, C$_{1-6}$ alkoxy, C$_{2-6}$alkenyloxy, C$_{2-6}$alkynyloxy, C$_{1-6}$alkylamino, di-C$_{1-6}$alkylamino, CF$_3$, C(O)C$_{1-6}$alkyl, C(O)C$_{2-6}$alkenyl, C(O)C$_{2-6}$alkynyl, CO$_2$H, CO$_2$C$_{1-6}$alkyl, CO$_2$C$_{2-6}$alkenyl, and CO$_2$C$_{2-6}$alkynyl, said alkyl, alkenyl, alkynyl and the alkyl portions of alkylamino and dialkylamino being optionally substituted with 1–3 of: hydroxy, halo, aryl, C$_{1-6}$ alkoxy, C$_{2-6}$alkenyloxy, C$_{2-6}$alkynyloxy, CF$_3$, C(O)C$_{1-6}$alkyl, C(O)C$_{2-6}$alkenyl, C(O)C$_{2-6}$alkynyl, CO$_2$H, CO$_2$C$_{1-6}$alkyl, CO$_2$C$_{2-6}$alkenyl, CO$_2$C$_{2-6}$ alkynyl, NH$_2$, NHC$_{1-6}$alkyl and N(C$_{1-6}$alkyl)$_2$.

2. A compound represented by formula I:

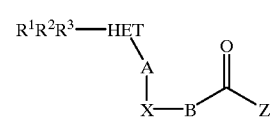

or a pharmaceutically acceptable salt, hydrate or ester thereof, wherein:

HET represents a member selected from the group consisting of: phenyl, naphthalene, biphenyl, pyridine, quinoline, isoquinoline, furan, benzofuran, thiophene, benzothiophene, oxazole, thiazole, imidazole, benzothiazole, 1,2,5-thiadiazole, thienopyridine, indole, tetrazole, imidazole, benzoxazole and pyrrole;

A represents a one or two atom moiety and is selected from the group consisting of: S, S(O), SO$_2$, CH$_2$, —C(O)—, —OCH$_2$—, —CHOH—, —C(OH)(CH$_3$)— and —CH$_2$—O—;

X represents phenyl optionally substituted with R$^{14}$ and R$^{15}$, and A and B are attached to the phenyl group ortho relative to each other;

B is CH=CH;

Z is OH;

R$^1$, R$^2$ and R$^3$ independently represent H, halogen, lower alkyl, lower alkenyl, lower alkynyl, lower alkenyl-HET (R$^a$)$_{4-9}$, —(C(R$^4$)$_2$)$_p$SR$^5$, —(C(R$^4$)$_2$)$_p$OR$^8$, —(C(R$^4$)$_2$)$_p$N(R$^6$)$_2$, CN, NO$_2$, —(C(R$^4$)$_2$)$_p$C(R$^7$)$_3$, —CO$_2$R$^9$, —CON(R$^6$)$_2$ or —(C(R$^4$)$_2$)$_p$S(O)$_n$R$^{10}$, wherein p and n are each independently 0–3;

each R$^4$ is independently H, F, CF$_3$ or lower alkyl, or two R$^4$ groups are taken in conjunction and represent a ring of up to six atoms, optionally containing one heteroatom selected from O, S(O)$_n$ or N(O)$_m$;

each R$^5$ is independently lower alkyl, lower alkenyl, lower alkynyl, CF$_3$, lower alkyl-HET, lower alkenyl-HET or —(C(R$^{18}$)$_2$)$_p$Ph(R$^{11}$)$_{0-2}$;

each R$^6$ is independently H, lower alkyl, lower alkenyl, lower alkynyl, CF$_3$, Ph, Bn and when two R$^6$ groups are attached to N they may be taken in conjunction and represents a ring of up to 6 atoms, optionally containing an additional heteroatom selected from O, S(O)$_n$ or N(O)$_m$;

each R$^7$ is independently H, F, CF$_3$ or lower alkyl, and when two R$^7$ groups are presents, they may be taken in conjunction and represent an aromatic or aliphatic ring of 3 to 6 members containing from 0–2 heteroatoms selected from O, S(O)$_n$ and N(O)$_m$;

each R$^8$ represents H or R$^5$;

each R$^9$ is independently H, lower alkyl, lower alkenyl, lower alkynyl, Ph or Bn;

each R$^{10}$ is independently lower alkyl, lower alkenyl, lower alkynyl, CF$_3$, Ph(R$^{11}$)$_{0-3}$, CH$_2$Ph(R$^{11}$)$_{0-3}$ or N(R$^6$)$_2$;

each R$^{11}$ is independently lower alkyl, SR$^{20}$, OR$^{20}$, N(R$^6$)$_2$, —CO$_2$R$^{12}$, —CON(R$^6$)$_2$, —C(O)R$^{12}$, CN, CF$_3$, NO$_2$ or halogen;

each R$^{12}$ is independently H, lower alkyl or benzyl;

each R$^{13}$ is independently H, halo, lower alkyl, O-lower alkenyl, S-lower alkyl, N(R$^6$)$_2$, CO$_2$R$^{12}$, CN, CF$_3$ or NO$_2$;

$R^{14}$ and $R^{15}$ are independently lower alkyl, halogen, $CF_3$, $OR^{16}$, $S(O)_nR^{16}$ or $C(R^{16})_2OR^{17}$;

each $R^{16}$ is independently H, lower alkyl, lower alkenyl, Ph, Bn or $CF_3$;

each $R^{17}$ is independently H, lower alkyl or Bn;

each $R^{18}$ is independently H, F or lower alkyl, and when two $R^{18}$ groups are present, they may be taken in conjunction and represent a ring of 3 to 6 members comprising carbon atoms and optionally one heteroatom chosen from O, $S(O)_n$ or N;

each $R^{20}$ is independently H, lower alkyl, lower alkenyl, lower alkynyl, $CF_3$ or $Ph(R^{13})_2$ and each $R^a$ is independently selected from the group consisting of: H, OH, halo, CN, $NO_2$, amino, $C_{1-6}$alkyl, $C_{2-6}$alkenyl, $C_{2-6}$alkynyl, $C_{1-6}$ alkoxy, $C_{2-6}$alkenyloxy, $C_{2-6}$alkynyloxy, $C_{1-6}$alkylamino, di-$C_{1-6}$alkylamino, $CF_3$, $C(O)C_{1-6}$alkyl, $C(O)C_{2-6}$alkenyl, $C(O)C_{2-6}$alkynyl, $CO_2H$, $CO_2C_{1-6}$alkyl, $CO_2C_{2-6}$alkenyl, and $CO_2C_{2-6}$alkynyl, said alkyl, alkenyl, alkynyl and the alkyl portions of alkylamino and dialkylamino being optionally substituted with 1–3 of: hydroxy, halo, aryl, $C_{1-6}$ alkoxy, $C_{2-6}$alkenyloxy, $C_{2-6}$alkynyloxy, $CF_3$, $C(O)C_{1-6}$alkyl, $C(O)C_{2-6}$alkenyl, $C(O)C_{2-6}$alkynyl, $CO_2H$, $CO_2C_{1-6}$alkyl, $CO_2C_{2-6}$alkenyl, $CO_2C_{2-6}$ alkynyl, $NH_2$, $NHC_{1-6}$alkyl and $N(C_{1-6}$alkyl$)_2$.

3. A compound in accordance with claim 1 wherein:

$R^{19}$ represents a member selected from the group consisting of: lower alkyl and HET($R^a$)$_3$.

4. A compound in accordance with claim 3 wherein:

R19 represents HET($R^a$)$_3$ and HET is selected from the group consisting of: phenyl, thienyl, naphthyl, furanyl, thiazolyl, imidazolyl and indolyl.

5. A compound in accordance with claim 3 wherein:

$R^{19}$ represents benzene or thiophene, substituted with ($R^a$)$_3$.

6. A compound in accordance with claim 1 wherein:

HET represents a member selected from the group consisting of: phenyl, naphthalene, biphenyl, pyridine, quinoline, isoquinoline, furan, benzofuran, thiophene, benzothiophene, oxazole, thiazole, imidazole, benzothiazole, 1,2,5-thiadiazole, thienopyridine, indole, tetrazole, imidazole, benzoxazole and pyrrole;

A represents a one or two atom moiety and is selected from the group consisting of: S, S(O), $SO_2$, $CH_2$, —C(O)—, —$OCH_2$—, —CHOH—, —C(OH)($CH_3$)— and —$CH_2$—O—;

X represents phenyl optionally substituted with $R^{14}$ and $R^{15}$;

B is CH=CH;

Z is $NHSO_2R^{19}$ and $R^{19}$ represents a member selected from the group consisting of: lower alkyl and HET($R^a$)$_3$.

7. A compound represented in one of the following tables:

TABLE I

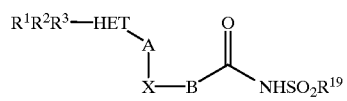

Ia (Compounds 1–323 and 347–454)

| $R^1R^2R^3$—Het | A | X | B | $R^{19}$ | Cpd |
|---|---|---|---|---|---|
| 1-naphthyl | $CH_2$ | 1,2-Ph | CH=CH | Ph(F)5 | 1 |
| 2-naphthyl | $S(O)_2$ | 1,2-Ph | CH=CH | Ph(F)5 | 2 |
| 3-methylindol-1-yl | $CH_2$ | 1,2-Ph | CH=CH | 2-thienyl | 3 |
| 2-naphthyl | $CH_2$ | 1,2-Ph | CH=CH | 2-thienyl | 4 |
| 2-naphthyl | $S(O)_2$ | 1,2-Ph | CH=CH | phenyl | 5 |
| 3-methylindol-1-yl | $S(O)_2$ | 1,2-Ph | CH=CH | 2-thienyl | 6 |
| 2-naphthyl | $S(O)_2$ | 1,2-Ph | CH=CH | 3,5-di-($CF_3$)phenyl | 7 |
| 3,4-dichlorophenyl | $CH_2$ | 1,2-Ph | CH=CH | 2-thienyl | 8 |
| 2-naphthyl | $S(O)_2$ | 1,2-Ph | CH=CH | 2-thienyl | 9 |
| 2,4-dichlorophenyl | $CH_2$ | 1,2-Ph | CH=CH | 2-thienyl | 10 |
| 1-naphthyl | $S(O)_2$ | 1,2-Ph | CH=CH | Ph(F)3 | 11 |
| 1-naphthyl | $S(O)_2$ | 1,2-Ph | CH=CH | 3,5-di-($CF_3$)phenyl | 12 |
| 2-naphthyl | $S(O)_2$ | 1,2-Ph | 1,2-c-propyl | 2-thienyl | 13 |
| 3,4-chlorofluorophenyl | $CH_2$ | 1,2-Ph | CH=CH | 2-thienyl | 14 |
| 1-naphthyl | $CH_2$ | 1,2-Ph | CH=CH | 2-thienyl | 15 |
| 3,4-dichlorophenyl | $S(O)_2$ | 1,2-Ph | CH=CH | 2-thienyl | 16 |
| 4-methylthiophenyl | $CH_2$ | 1,2-Ph | CH=CH | 2-thienyl | 17 |
| 4-chlorophenyl | $CH_2$ | 1,2-Ph | CH=CH | 2-thienyl | 18 |
| 2-naphthyl | S | 1,2-Ph | CH=CH | 2-thienyl | 19 |
| 2-naphthyl | O—$CH_2$ | 1,2-Ph | CH=CH | 2-thienyl | 20 |
| 2-naphthyl | S(O) | 1,2-Ph | CH=CH | 2-thienyl | 21 |

TABLE I-continued $$R^1R^2R^3\text{—HET} \overset{A}{\underset{X\text{—}B}{\diagdown}} \overset{O}{\underset{}{\diagdown}} NHSO_2R^{19}$$

Ia (Compounds 1–323 and 347–454)

| $R^1R^2R^3$—Het | A | X | B | $R^{19}$ | Cpd |
|---|---|---|---|---|---|
| 1-naphthyl | S(O)$_2$ | 1,2-Ph | CH=CH | phenyl | 22 |
| 2-benzofuranyl | CH$_2$ | 1,2-Ph | CH=CH | 2-thienyl | 23 |
| 3,5-dichloro phenyl | CH$_2$ | 1,2-Ph | CH=CH | 2-thienyl | 24 |
| 1-naphthyl | S(O)$_2$ | 1,2-Ph | CH=CH | 3,5-di-(CF$_3$) phenyl | 25 |
| 1-naphthyl | S(O)$_2$ | 1,2-Ph | CH=CH | 2-thienyl | 26 |
| 3-(1,2-(methylene dioxy)benzene) | CH$_2$ | 1,2-Ph | CH=CH | 2-thienyl | 27 |
| 2-naphthyl | O | 1,2-Ph | CH=CH | 2-thienyl | 28 |
| R$^s$-2-phenyl | CH$_2$ | 1,2-Ph | CH$_2$—O | 2-thienyl | 29 |
| R$^s$-2-phenyl | CH$_2$ | 1,2-Ph | CH$_2$—CH$_2$ | 2-thienyl | 30 |
| 2-naphthyl | S(O)$_2$ | 1,2-Ph | CH$_2$—O | 2-thienyl | 31 |
| 3-((2-(Qn)vinyl)) phenyl | CH$_2$ | 1,2-Ph | CH$_2$—O | 2-thienyl | 32 |
| 2-(6-benzyloxy) naphthyl | CH$_2$ | 1,2-Ph | CH=CH | 2-thienyl | 33 |
| 3-((2-(Qn)vinyl)) phenyl | SO | 1,2-Ph | CH$_2$—O | 2-thienyl | 34 |
| 3-((2-(Qn)vinyl)) phenyl | —CHOH— | 1,2-Ph | CH$_2$—O | 2-thienyl | 35 |
| 3-((2-(Qn)vinyl)) phenyl | S(O)$_2$ | 1,2-Ph | CH$_2$—O | phenyl | 36 |
| 3-((2-(Qn)vinyl)) phenyl | O—CH$_2$ | 1,2-Ph | CH$_2$—O | 2-thienyl | 37 |
| 3-tolyl-D-3-phenyl | O—CH$_2$ | 1,2-Ph | CH$_2$—O | 2-thienyl | 38 |
| 3-((2-(Qn)vinyl)) phenyl | CH(OH)—CH$_3$— | 1,2-Ph | CH$_2$—O | phenyl | 39 |
| 3-((2-(Qn)vinyl)) phenyl | S | 1,2-Ph | CH$_2$—O | 2-thienyl | 40 |
| 3-((2-(Qn)vinyl)) phenyl | O | 1,2-Ph | CH$_2$—O | phenyl | 41 |
| 3-((2-(Qn)vinyl)) phenyl | C=O | 1,2-Ph | CH$_2$—O | 2-thienyl | 42 |
| 3-((2-(Qn)vinyl)) phenyl | O | 1,2-Ph | C(CH$_3$)$_2$—O | 2-thienyl | 43 |
| 3-((2-(Qn)vinyl)) phenyl | O | 1,2-Ph | CH$_2$—O | 2-thienyl | 44 |
| 2-naphthyl | CH$_2$ | 1,2-Ph | 1,2-c-propyl | 2-thienyl | 45 |
| 2-(6-benzyloxy) naphthyl | CH$_2$ | 1,2-Ph | CH=CH | 2-methoxy-5-bromophenyl | 46 |
| 2-naphthyl | CH$_2$ | 1,2-Ph | 1,2-c-propyl | 3,4-dichloro phenyl | 47 |
| 2-naphthyl | CH$_2$ | 1,2-Ph | 1,2-c-propyl | 4-fluoro phenyl | 48 |
| 2-naphthyl | CH$_2$ | 1,2-Ph | 1,2-c-propyl | 4-chloro phenyl | 49 |
| 2-naphthyl | CH$_2$ | 1,2-Ph | 1,2-c-propyl | 4-propyl phenyl | 50 |
| 2-naphthyl | CH$_2$ | 1,2-Ph | 1,2-c-propyl | 2,5-dichloro thienyl | 51 |
| 2-naphthyl | CH$_2$ | 1,2-Ph | 1,2-c-propyl | styryl | 52 |
| 2-naphthyl | CH$_2$ | 1,2-Ph | 1,2-c-propyl | 3-chloro-4-fluorophenyl | 53 |
| 2-naphthyl | CH$_2$ | 1,2-Ph | 1,2-c-propyl | 4-methoxy phenyl | 54 |
| 2-naphthyl | CH$_2$ | 1,2-Ph | 1,2-c-propyl | 3-bromo phenyl | 55 |
| 2-naphthyl | CH$_2$ | 1,2-Ph | 1,2-c-propyl | 2,5-dimethyl phenyl | 56 |
| 2-naphthyl | CH$_2$ | 1,2-Ph | 1,2-c-propyl | 2-nitro-4-chloro phenyl | 57 |
| 2-naphthyl | CH$_2$ | 1,2-Ph | 1,2-c-propyl | 2-carbomethoxy phenyl | 58 |
| 2-naphthyl | CH$_2$ | 1,2-Ph | 1,2-c-propyl | 2,4-difluoro phenyl | 59 |
| 2-naphthyl | CH$_2$ | 1,2-Ph | 1,2-c-propyl | 4-butyl-phenyl | 60 |
| 2-naphthyl | CH$_2$ | 1,2-Ph | 1,2-c-propyl | butyl | 61 |

TABLE I-continued $$R^1R^2R^3-HET\underset{X-B}{\overset{A}{\diagdown}}\underset{NHSO_2R^{19}}{\overset{O}{\diagup}}$$

Ia (Compounds 1–323 and 347–454)

| $R^1R^2R^3$—Het | A | X | B | $R^{19}$ | Cpd |
|---|---|---|---|---|---|
| 2-naphthyl | CH$_2$ | 1,2-Ph | 1,2-c-propyl | 2,5-dimethoxy phenyl | 62 |
| 2-naphthyl | CH$_2$ | 1,2-Ph | 1,2-c-propyl | 3-trifluoro methylphenyl | 63 |
| 2-naphthyl | CH$_2$ | 1,2-Ph | 1,2-c-propyl | 3,5-difluoro phenyl | 64 |
| 2-naphthyl | CH$_2$ | 1,2-Ph | 1,2-c-propyl | 3,5-dichloro phenyl | 65 |
| 2-naphthyl | CH$_2$ | 1,2-Ph | 1,2-c-propyl | 4-((1-hydroxy-1-methyl)ethyl) phenyl | 66 |
| 2-naphthyl | CH$_2$ | 1,2-Ph | 1,2-c-propyl | 4-(hydroxy methyl)phenyl | 67 |
| 2-naphthyl | CH$_2$ | 1,2-Ph | 1,2-c-propyl | 3-(hydroxy methyl)phenyl | 68 |
| 2-naphthyl | CH$_2$ | 1,2-Ph | 1,2-c-propyl | 4-(methyl sulfonyl)phenyl | 69 |
| 2-naphthyl | CH$_2$ | 1,2-Ph | 1,2-c-propyl | 3-(methyl sulfonyl)phenyl | 70 |
| 2-naphthyl | CH$_2$ | 1,2-Ph | 1,2-c-propyl | 4-(propyl sulfonyl)phenyl | 71 |
| 2-naphthyl | CH$_2$ | 1,2-Ph | 1,2-c-propyl | 4-((bis-trifluoro-methyl)-hydroxy methyl)phenyl | 72 |
| 2-naphthyl | CH$_2$ | 1,2-Ph | 1,2-c-propyl | 4-(benzyloxy) phenyl | 73 |
| 2-naphthyl | CH$_2$ | 1,2-Ph | 1,2-c-propyl | 4-((1-methoxy-1-methyl) ethyl)phenyl | 74 |
| 2-naphthyl | CH$_2$ | 1,2-Ph | 1,2-c-propyl | 4-dimethyl aminophenyl | 75 |
| 2-naphthyl | CH$_2$ | 1,2-Ph | 1,2-c-propyl | cyclohexyl | 76 |
| 2-naphthyl | CH$_2$ | 1,2-Ph | 1,2-c-propyl | cyclopentyl | 77 |
| 2-naphthyl | CH$_2$ | 1,2-Ph | 1,2-c-propyl | 4-morpholinYL | 78 |
| 2-naphthyl | CH$_2$ | 1,2-Ph | 1,2-c-propyl | 2-naphthyl | 79 |
| 2-naphthyl | CH$_2$ | 1,2-Ph | 1,2-c-propyl | 2-thiazolyl | 80 |
| 2-naphthyl | CH$_2$ | 1,2-Ph | 1,2-c-propyl | 1-imidazolyl | 81 |
| 2-naphthyl | CH$_2$ | 1,2-Ph | 1,2-c-propyl | 2-furanyl | 82 |
| 2-naphthyl | CH$_2$ | 1,2-Ph | 1,2-c-propyl | 3-(2-chloro)-furanyl | 83 |
| 2-naphthyl | CH$_2$ | 1,2-Ph | 1,2-c-propyl | 2-pyridinyl | 84 |
| 2-naphthyl | CH$_2$ | 1,2-Ph | 1,2-c-propyl | 2-(4-chloro) pyridinyl | 85 |
| 2-naphthyl | CH$_2$ | 1,2-Ph | 1,2-c-propyl | 3-indolyl | 86 |
| 2-naphthyl | CH$_2$ | 1,2-Ph | 1,2-c-propyl | 4-nitrophenyl | 87 |
| 2-naphthyl | CH$_2$ | 1,2-Ph | 1,2-c-propyl | 4-cyanophenyl | 88 |
| 2-naphthyl | S(O)$_2$ | 1,2-Ph | 1,2-c-propyl | 4-((1-hydroxy-1-methyl)ethyl) phenyl | 89 |
| 2-naphthyl | S(O)$_2$ | 1,2-Ph | 1,2-c-propyl | 4-(hydroxy methyl)phenyl | 90 |
| 2-naphthyl | S(O)$_2$ | 1,2-Ph | 1,2-c-propyl | 3-(hydroxy methyl)phenyl | 91 |
| 2-naphthyl | S(O)$_2$ | 1,2-Ph | 1,2-c-propyl | 2,5-dimethyl phenyl | 92 |
| 2-naphthyl | S(O)$_2$ | 1,2-Ph | 1,2-c-propyl | 2-carbomethoxy phenyl | 93 |
| 2-naphthyl | S(O)$_2$ | 1,2-Ph | 1,2-c-propyl | 2,4-difluoro phenyl | 94 |
| 2-naphthyl | S(O)$_2$ | 1,2-Ph | 1,2-c-propyl | 4-(methyl sulfonyl)phenyl | 95 |
| 2-naphthyl | S(O)$_2$ | 1,2-Ph | 1,2-c-propyl | 3-(methyl sulfonyl)phenyl | 96 |
| 2-naphthyl | S(O)$_2$ | 1,2-Ph | 1,2-c-propyl | 4-(propyl sulfonyl)phenyl | 97 |
| 2-naphthyl | S(O)$_2$ | 1,2-Ph | 1,2-c-propyl | 4-butyl-phenyl | 98 |
| 2-naphthyl | S(O)$_2$ | 1,2-Ph | 1,2-c-propyl | 3,5-di-(CF$_3$) phenyl | 99 |

TABLE I-continued $$R^1R^2R^3\text{—HET} \underset{X-B}{\overset{A}{\diagdown}} \overset{O}{\underset{}{\diagup}} NHSO_2R^{19}$$ Ia (Compounds 1–323 and 347–454)

| R¹R²R³—Het | A | X | B | R¹⁹ | Cpd |
|---|---|---|---|---|---|
| 2-naphthyl | S(O)₂ | 1,2-Ph | 1,2-c-propyl | 4-((bis-trifluoro methyl)-hydroxy methyl)phenyl | 100 |
| 2-naphthyl | S(O)₂ | 1,2-Ph | 1,2-c-propyl | 3-bromophenyl | 101 |
| 2-naphthyl | S(O)₂ | 1,2-Ph | 1,2-c-propyl | 4-(benzyloxy) phenyl | 102 |
| 2-naphthyl | S(O)₂ | 1,2-Ph | 1,2-c-propyl | 2-nitro-4-chloro phenyl | 103 |
| 2-naphthyl | S(O)₂ | 1,2-Ph | 1,2-c-propyl | 4-isopropyl phenyl | 104 |
| 2-naphthyl | S(O)₂ | 1,2-Ph | 1,2-c-propyl | 4-((1-methoxy-1-methyl) ethyl)phenyl | 105 |
| 2-naphthyl | S(O)₂ | 1,2-Ph | 1,2-c-propyl | 4-methoxy phenyl | 106 |
| 2-naphthyl | S(O)₂ | 1,2-Ph | 1,2-c-propyl | 4-dimethyl aminophenyl | 107 |
| 2-naphthyl | S(O)₂ | 1,2-Ph | 1,2-c-propyl | 3,4-dichloro phenyl | 108 |
| 2-naphthyl | S(O)₂ | 1,2-Ph | 1,2-c-propyl | 3,4-difluoro phenyl | 109 |
| 2-naphthyl | S(O)₂ | 1,2-Ph | 1,2-c-propyl | 4-fluorophenyl | 110 |
| 2-naphthyl | S(O)₂ | 1,2-Ph | 1,2-c-propyl | cyclohexyl | 111 |
| 2-naphthyl | S(O)₂ | 1,2-Ph | 1,2-c-propyl | cyclopentyl | 112 |
| 2-naphthyl | S(O)₂ | 1,2-Ph | 1,2-c-propyl | 4-morpholinyl | 113 |
| 2-naphthyl | S(O)₂ | 1,2-Ph | 1,2-c-propyl | butyl | 114 |
| 2-naphthyl | S(O)₂ | 1,2-Ph | 1,2-c-propyl | 4-chlorophenyl | 115 |
| 2-naphthyl | S(O)₂ | 1,2-Ph | 1,2-c-propyl | 4-propylphenyl | 116 |
| 2-naphthyl | S(O)₂ | 1,2-Ph | 1,2-c-propyl | 2-naphthyl | 117 |
| 2-naphthyl | S(O)₂ | 1,2-Ph | 1,2-c-propyl | 2-thiazolyl | 118 |
| 2-naphthyl | S(O)₂ | 1,2-Ph | 1,2-c-propyl | 1-imidazolyl | 119 |
| 2-naphthyl | S(O)₂ | 1,2-Ph | 1,2-c-propyl | 2,5-dimethoxy phenyl | 120 |
| 2-naphthyl | S(O)₂ | 1,2-Ph | 1,2-c-propyl | 3-trifluoro methylphenyl | 121 |
| 2-naphthyl | S(O)₂ | 1,2-Ph | 1,2-c-propyl | 2,5-dichloro-3-thienyl | 122 |
| 2-naphthyl | S(O)₂ | 1,2-Ph | 1,2-c-propyl | 2-furanyl | 123 |
| 2-naphthyl | S(O)₂ | 1,2-Ph | 1,2-c-propyl | 3-(2-chloro)-furanyl | 124 |
| 2-naphthyl | S(O)₂ | 1,2-Ph | 1,2-c-propyl | 2-pyridinyl | 125 |
| 2-naphthyl | S(O)₂ | 1,2-Ph | 1,2-c-propyl | 2-styryl | 126 |
| 2-naphthyl | S(O)₂ | 1,2-Ph | 1,2-c-propyl | 3,5-difluoro-phenyl | 127 |
| 2-naphthyl | S(O)₂ | 1,2-Ph | 1,2-c-propyl | 3,5-dichloro-phenyl | 128 |
| 2-naphthyl | S(O)₂ | 1,2-Ph | 1,2-c-propyl | 2-(4-chloro) pyridinyl | 129 |
| 2-naphthyl | S(O)₂ | 1,2-Ph | 1,2-c-propyl | 3-indolyl | 130 |
| 2-naphthyl | S(O)₂ | 1,2-Ph | 1,2-c-propyl | 4-nitrophenyl | 131 |
| 2-naphthyl | S(O)₂ | 1,2-Ph | 1,2-c-propyl | 4-cyanophenyl | 132 |
| 2-naphthyl | S(O)₂ | 1,2-Ph | 1,2-c-propyl | 3-chloro-4-fluorophenyl | 133 |
| 3-methylindol-1-yl | CH₂ | 1,2-Ph | 1,2-c-propyl | 3,5-di-(CF₃)-phenyl | 134 |
| 3-methylindol-1-yl | CH₂ | 1,2-Ph | 1,2-c-propyl | 4-isopropyl phenyl | 135 |
| 3-methylindol-1-yl | CH₂ | 1,2-Ph | 1,2-c-propyl | 3,4-dichloro phenyl | 136 |
| 3-methylindol-1-yl | CH₂ | 1,2-Ph | 1,2-c-propyl | 3,4-difluoro phenyl | 137 |
| 3-methylindol-1-yl | CH₂ | 1,2-Ph | 1,2-c-propyl | 4-fluorophenyl | 138 |
| 3-methylindol-1-yl | CH₂ | 1,2-Ph | 1,2-c-propyl | 4-chlorophenyl | 139 |
| 3-methylindol-1-yl | CH₂ | 1,2-Ph | 1,2-c-propyl | 4-propylphenyl | 140 |
| 3-methylindol- | CH₂ | 1,2-Ph | 1,2-c-propyl | 2,5-dichloro-3- | 141 |

TABLE I-continued $$R^1R^2R^3\text{—HET}\overset{A}{\underset{X\text{—}B}{\diagdown}}\overset{O}{\underset{}{\diagup}}\text{NHSO}_2R^{19} \quad \text{Ia}$$

(Compounds 1–323 and 347–454)

| $R^1R^2R^3$—Het | A | X | B | $R^{19}$ | Cpd |
|---|---|---|---|---|---|
| 3-methylindol-1-yl | CH$_2$ | 1,2-Ph | 1,2-c-propyl | thienyl 2-styryl | 142 |
| 3-methylindol-1-yl | CH$_2$ | 1,2-Ph | 1,2-c-propyl | 3-chloro-4-fluoro phenyl | 143 |
| 3-methylindol-1-yl | CH$_2$ | 1,2-Ph | 1,2-c-propyl | 4-methoxy phenyl | 144 |
| 3-methylindol-1-yl | CH$_2$ | 1,2-Ph | 1,2-c-propyl | 3-bromophenyl | 145 |
| 3-methylindol-1-yl | CH$_2$ | 1,2-Ph | 1,2-c-propyl | 2,5-dimethyl phenyl | 146 |
| 3-methylindol-1-yl | CH$_2$ | 1,2-Ph | 1,2-c-propyl | 2-nitro-4-chloro phenyl | 147 |
| 3-methylindol-1-yl | CH$_2$ | 1,2-Ph | 1,2-c-propyl | 2-carbomethoxy phenyl | 148 |
| 3-methylindol-1-yl | CH$_2$ | 1,2-Ph | 1,2-c-propyl | 2,4-difluoro phenyl | 149 |
| 3-methylindol-1-yl | CH$_2$ | 1,2-Ph | 1,2-c-propyl | 4-butylphenyl | 150 |
| 3-methylindol-1-yl | CH$_2$ | 1,2-Ph | 1,2-c-propyl | n-butyl | 151 |
| 3-methylindol-1-yl | CH$_2$ | 1,2-Ph | 1,2-c-propyl | 2,5-dimethoxy phenyl | 152 |
| 3-methylindol-1-yl | CH$_2$ | 1,2-Ph | 1,2-c-propyl | 3-trifluoro methylphenyl | 153 |
| 3-methylindol-1-yl | CH$_2$ | 1,2-Ph | 1,2-c-propyl | 3,5-difluoro phenyl | 154 |
| 3-methylindol-1-yl | CH$_2$ | 1,2-Ph | 1,2-c-propyl | 3,5-dichloro phenyl | 155 |
| 3-methylindol-1-yl | CH$_2$ | 1,2-Ph | 1,2-c-propyl | 4-((1-hydroxy-1-methyl)ethyl) phenyl | 156 |
| 3-methylindol-1-yl | CH$_2$ | 1,2-Ph | 1,2-c-propyl | 4-(hydroxy methyl)phenyl | 157 |
| 3-methylindol-1-yl | CH$_2$ | 1,2-Ph | 1,2-c-propyl | 3-(hydroxy methyl)phenyl | 158 |
| 3-methylindol-1-yl | CH$_2$ | 1,2-Ph | 1,2-c-propyl | 4-(methyl sulfonyl)phenyl | 159 |
| 3-methylindol-1-yl | CH$_2$ | 1,2-Ph | 1,2-c-propyl | 3-(methyl sulfonyl)phenyl | 160 |
| 3-methylindol-1-yl | CH$_2$ | 1,2-Ph | 1,2-c-propyl | 4-(propyl sulfonyl)phenyl | 161 |
| 3-methylindol-1-yl | CH$_2$ | 1,2-Ph | 1,2-c-propyl | 4-((bis-trifluoro methyl)hydroxy methyl)phenyl | 162 |
| 3-methylindol-1-yl | CH$_2$ | 1,2-Ph | 1,2-c-propyl | 4-(benzyloxy) phenyl | 163 |
| 3-methylindol-1-yl | CH$_2$ | 1,2-Ph | 1,2-c-propyl | 4-((1-methoxy-1-methyl) ethyl)phenyl | 164 |
| 3-methylindol-1-yl | CH$_2$ | 1,2-Ph | 1,2-c-propyl | 4-dimethyl aminophenyl | 165 |
| 3-methylindol-1-yl | CH$_2$ | 1,2-Ph | 1,2-c-propyl | cyclohexyl | 166 |
| 3-methylindol-1-yl | CH$_2$ | 1,2-Ph | 1,2-c-propyl | cyclopentyl | 167 |
| 3-methylindol-1-yl | CH$_2$ | 1,2-Ph | 1,2-c-propyl | 4-morpholinyl | 168 |
| 3-methylindol-1-yl | CH$_2$ | 1,2-Ph | 1,2-c-propyl | 2-naphthyl | 169 |
| 3-methylindol-1-yl | CH$_2$ | 1,2-Ph | 1,2-c-propyl | 2-thiazolyl | 170 |
| 3-methylindol-1-yl | CH$_2$ | 1,2-Ph | 1,2-c-propyl | 1-imidazolyl | 171 |
| 3-methylindol-1-yl | CH$_2$ | 1,2-Ph | 1,2-c-propyl | 2-furanyl | 172 |
| 3-methylindol-1-yl | CH$_2$ | 1,2-Ph | 1,2-c-propyl | 3-(2-chloro)-furanyl | 173 |

TABLE I-continued $$R^1R^2R^3-HET\underset{X-B}{\overset{A}{\diagdown}}\overset{O}{\underset{}{\diagup}}NHSO_2R^{19}$$

Ia (Compounds 1–323 and 347–454)

| $R^1R^2R^3$—Het | A | X | B | $R^{19}$ | Cpd |
|---|---|---|---|---|---|
| 3-methylindol-1-yl | CH$_2$ | 1,2-Ph | 1,2-c-propyl | 2-pyridinyl | 174 |
| 3-methylindol-1-yl | CH$_2$ | 1,2-Ph | 1,2-c-propyl | 2-(4-chloro) pyridinyl | 175 |
| 3-methylindol-1-yl | CH$_2$ | 1,2-Ph | 1,2-c-propyl | 3-indolyl | 176 |
| 3-methylindol-1-yl | CH$_2$ | 1,2-Ph | 1,2-c-propyl | 4-nitrophenyl | 177 |
| 3-methylindol-1-yl | CH$_2$ | 1,2-Ph | 1,2-c-propyl | 4-cyanophenyl | 178 |
| 3-methylindol-1-yl | SO$_2$ | 1,2-Ph | 1,2-c-propyl | 3,5-di-(CF$_3$) phenyl | 179 |
| 3-methylindol-1-yl | SO$_2$ | 1,2-Ph | 1,2-c-propyl | 4-isopropyl phenyl | 180 |
| 3-methylindol-1-yl | SO$_2$ | 1,2-Ph | 1,2-c-propyl | 3,4-dichloro phenyl | 181 |
| 3-methylindol-1-yl | SO$_2$ | 1,2-Ph | 1,2-c-propyl | 3,4-difluoro phenyl | 182 |
| 3-methylindol-1-yl | SO$_2$ | 1,2-Ph | 1,2-c-propyl | 4-fluorophenyl | 183 |
| 3-methylindol-1-yl | SO$_2$ | 1,2-Ph | 1,2-c-propyl | 4-chlorophenyl | 184 |
| 3-methylindol-1-yl | SO$_2$ | 1,2-Ph | 1,2-c-propyl | 4-propylphenyl | 185 |
| 3-methylindol-1-yl | SO$_2$ | 1,2-Ph | 1,2-c-propyl | 2,5-dichloro-3-thienyl | 186 |
| 3-methylindol-1-yl | SO$_2$ | 1,2-Ph | 1,2-c-propyl | 2-styryl | 187 |
| 3-methylindol-1-yl | SO$_2$ | 1,2-Ph | 1,2-c-propyl | 3-chloro-4-fluorophenyl | 188 |
| 3-methylindol-1-yl | SO$_2$ | 1,2-Ph | 1,2-c-propyl | 4-methoxy phenyl | 189 |
| 3-methylindol-1-yl | SO$_2$ | 1,2-Ph | 1,2-c-propyl | 3-bromo phenyl | 190 |
| 3-methylindol-1-yl | SO$_2$ | 1,2-Ph | 1,2-c-propyl | 2,5-dimethyl phenyl | 191 |
| 3-methylindol-1-yl | SO$_2$ | 1,2-Ph | 1,2-c-propyl | 2-nitro-4-chloro phenyl | 192 |
| 3-methylindol-1-yl | SO$_2$ | 1,2-Ph | 1,2-c-propyl | 2-carbomethoxy phenyl | 193 |
| 3-methylindol-1-yl | SO$_2$ | 1,2-Ph | 1,2-c-propyl | 2,4-difluoro phenyl | 194 |
| 3-methylindol-1-yl | SO$_2$ | 1,2-Ph | 1,2-c-propyl | 4-butylphenyl | 195 |
| 3-methylindol-1-yl | SO$_2$ | 1,2-Ph | 1,2-c-propyl | n-butyl | 196 |
| 3-methylindol-1-yl | SO$_2$ | 1,2-Ph | 1,2-c-propyl | 2,5-dimethoxy phenyl | 197 |
| 3-methylindol-1-yl | SO$_2$ | 1,2-Ph | 1,2-c-propyl | 3-trifluoromethyl phenyl | 198 |
| 3-methylindol-1-yl | SO$_2$ | 1,2-Ph | 1,2-c-propyl | 3,5-difluoro phenyl | 199 |
| 1-(3-methyl)indolyl | SO$_2$ | 1,2-Ph | 1,2-c-propyl | 3,5-dichloro phenyl | 200 |
| 3-methylindol-1-yl | SO$_2$ | 1,2-Ph | 1,2-c-propyl | 4-((1-hydroxy-1-methyl)ethyl) phenyl | 201 |
| 3-methylindol-1-yl | SO$_2$ | 1,2-Ph | 1,2-c-propyl | 4-(hydroxy methyl)phenyl | 202 |
| 3-methylindol-1-yl | SO$_2$ | 1,2-Ph | 1,2-c-propyl | 3-(hydroxy methyl)phenyl | 203 |
| 3-methylindol-1-yl | SO$_2$ | 1,2-Ph | 1,2-c-propyl | 4-(methyl sulfonyl)phenyl | 204 |
| 3-methylindol-1-yl | SO$_2$ | 1,2-Ph | 1,2-c-propyl | 3-(methyl sulfonyl)phenyl | 205 |
| 3-methylindol-1-yl | SO$_2$ | 1,2-Ph | 1,2-c-propyl | 4-(propyl sulfonyl)phenyl | 206 |
| 3-methylindol-1-yl | SO$_2$ | 1,2-Ph | 1,2-c-propyl | 4-((bis-trifluoro | 207 |

TABLE I-continued $R^1R^2R^3$—HET—A—X—B—C(=O)—NHSO$_2$R$^{19}$

Ia (Compounds 1–323 and 347–454)

| R$^1$R$^2$R$^3$—Het | A | X | B | R$^{19}$ | Cpd |
|---|---|---|---|---|---|
| 1-yl | | | | methyl)hydroxy methyl)phenyl | |
| 3-methylindol-1-yl | SO$_2$ | 1,2-Ph | 1,2-c-propyl | 4-(benzyloxy)phenyl | 208 |
| 3-methylindol-1-yl | SO$_2$ | 1,2-Ph | 1,2-c-propyl | 4-((1-methoxy-1-methyl)ethyl)-phenyl | 209 |
| 3-methylindol-1-yl | SO$_2$ | 1,2-Ph | 1,2-c-propyl | 4-dimethyl aminophenyl | 210 |
| 3-methylindol-1-yl | SO$_2$ | 1,2-Ph | 1,2-c-propyl | cyclohexyl | 211 |
| 3-methylindol-1-yl | SO$_2$ | 1,2-Ph | 1,2-c-propyl | cyclopentyl | 212 |
| 3-methylindol | SO$_2$ | 1,2-Ph | 1,2-c-propyl | 4-morpholinyl | 213 |
| 3-methylindol-1-yl | SO$_2$ | 1,2-Ph | 1,2-c-propyl | 2-naphthyl | 214 |
| 3-methylindol-1-yl | SO$_2$ | 1,2-Ph | 1,2-c-propyl | 2-thiazolyl | 215 |
| 3-methylindol-1-yl | SO$_2$ | 1,2-Ph | 1,2-c-propyl | 1-imidazolyl | 216 |
| 3-methylindol-1-yl | SO$_2$ | 1,2-Ph | 1,2-c-propyl | 2-furanyl | 217 |
| 3-methylindol-1-yl | SO$_2$ | 1,2-Ph | 1,2-c-propyl | 3-(2-chloro)-furanyl | 218 |
| 3-methylindol-1-yl | SO$_2$ | 1,2-Ph | 1,2-c-propyl | 2-pyridinyl | 219 |
| 3-methylindol-1-yl | SO$_2$ | 1,2-Ph | 1,2-c-propyl | 2-(4-chloro)pyridinyl | 220 |
| 3-methylindol-1-yl | SO$_2$ | 1,2-Ph | 1,2-c-propyl | 3-indolyl | 221 |
| 3-methylindol-1-yl | SO$_2$ | 1,2-Ph | 1,2-c-propyl | 4-nitrophenyl | 222 |
| 3-methylindol-1-yl | SO$_2$ | 1,2-Ph | 1,2-c-propyl | 4-cyanophenyl | 223 |
| 2-naphthyl | CH$_2$ | 1,2-Ph | CH=CH | 3,5-di-(CF$_3$)phenyl | 224 |
| 2-naphthyl | CH$_2$ | 1,2-Ph | CH=CH | 4-isopropyl phenyl | 225 |
| 2-naphthyl | CH$_2$ | 1,2-Ph | CH=CH | 2,3-dichloro phenyl | 226 |
| 2-naphthyl | CH$_2$ | 1,2-Ph | CH=CH | 3,4-difluoro phenyl | 227 |
| 2-naphthyl | CH$_2$ | 1,2-Ph | CH=CH | 4-chlorophenyl | 228 |
| 2-naphthyl | CH$_2$ | 1,2-Ph | CH=CH | 4-fluorophenyl | 229 |
| 2-naphthyl | CH$_2$ | 1,2-Ph | CH=CH | 2,5-dichloro-3-thienyl | 230 |
| 2-naphthyl | CH$_2$ | 1,2-Ph | CH=CH | 3-chloro-4-fluoro phenyl | 231 |
| 2-naphthyl | CH$_2$ | 1,2-Ph | CH=CH | 4-methoxy phenyl | 232 |
| 2-naphthyl | CH$_2$ | 1,2-Ph | CH=CH | butyl | 233 |
| 2-naphthyl | CH$_2$ | 1,2-Ph | CH=CH | 3-trifluoro methylphenyl | 234 |
| 2-naphthyl | CH$_2$ | 1,2-Ph | CH=CH | 4-((1-hydroxy-1-methyl)ethyl)phenyl | 235 |
| 2-naphthyl | CH$_2$ | 1,2-Ph | CH=CH | 4-(methyl sufonyl)phenyl | 236 |
| 2-naphthyl | CH$_2$ | 1,2-Ph | CH=CH | 4-(benzyloxy)phenyl | 237 |
| 2-naphthyl | CH$_2$ | 1,2-Ph | CH=CH | cyclohexyl | 238 |
| 2-naphthyl | CH$_2$ | 1,2-Ph | CH=CH | 4-morpholinyl | 239 |
| 2-naphthyl | CH$_2$ | 1,2-Ph | CH=CH | 2-thiazolyl | 240 |
| 2-naphthyl | CH$_2$ | 1,2-Ph | CH=CH | 2-furanyl | 241 |
| 2-naphthyl | CH$_2$ | 1,2-Ph | CH=CH | 2-pyridinyl | 242 |
| 2-naphthyl | CH$_2$ | 1,2-Ph | CH=CH | 4-cyanophenyl | 243 |
| 2-naphthyl | SO$_2$ | 1,2-Ph | CH=CH | 3,5-di-(CF$_3$)phenyl | 244 |

TABLE I-continued $$R^1R^2R^3-HET-A-X-B-C(=O)-NHSO_2R^{19}$$ Ia (Compounds 1–323 and 347–454)

| $R^1R^2R^3$—Het | A | X | B | $R^{19}$ | Cpd |
|---|---|---|---|---|---|
| 2-naphthyl | SO$_2$ | 1,2-Ph | CH=CH | 4-isopropyl phenyl | 245 |
| 2-naphthyl | SO$_2$ | 1,2-Ph | CH=CH | 2,3-dichloro phenyl | 246 |
| 2-naphthyl | SO$_2$ | 1,2-Ph | CH=CH | 3,4-difluoro phenyl | 247 |
| 2-naphthyl | SO$_2$ | 1,2-Ph | CH=CH | 4-chlorophenyl | 248 |
| 2-naphthyl | SO$_2$ | 1,2-Ph | CH=CH | 4-fluorophenyl | 249 |
| 2-naphthyl | SO$_2$ | 1,2-Ph | CH=CH | 2,5-dichloro-3-thienyl | 250 |
| 2-naphthyl | SO$_2$ | 1,2-Ph | CH=CH | 3-chloro-4-fluorophenyl | 251 |
| 2-naphthyl | SO$_2$ | 1,2-Ph | CH=CH | 4-methoxy phenyl | 252 |
| 2-naphthyl | SO$_2$ | 1,2-Ph | CH=CH | butyl | 253 |
| 2-naphthyl | SO$_2$ | 1,2-Ph | CH=CH | 3-trifluoro methylphenyl | 254 |
| 2-naphthyl | SO$_2$ | 1,2-Ph | CH=CH | 4-((1-hydroxy-1-methyl)ethyl) phenyl | 255 |
| 2-naphthyl | SO$_2$ | 1,2-Ph | CH=CH | 4-(methyl sufonyl)phenyl | 256 |
| 2-naphthyl | SO$_2$ | 1,2-Ph | CH=CH | 4-(benzyloxy) phenyl | 257 |
| 2-naphthyl | SO$_2$ | 1,2-Ph | CH=CH | cyclohexyl | 258 |
| 2-naphthyl | SO$_2$ | 1,2-Ph | CH=CH | 4-morpholinyl | 259 |
| 2-naphthyl | SO$_2$ | 1,2-Ph | CH=CH | 2-thiazolyl | 260 |
| 2-naphthyl | SO$_2$ | 1,2-Ph | CH=CH | 2-furanyl | 261 |
| 2-naphthyl | SO$_2$ | 1,2-Ph | CH=CH | 2-pyridinyl | 262 |
| 2-naphthyl | SO$_2$ | 1,2-Ph | CH=CH | 4-cyanophenyl | 263 |
| 2-naphthyl | CH$_2$—O | 1,2-Ph | CH=CH | 3,5-di-(CF$_3$) phenyl | 264 |
| 2-naphthyl | CH$_2$—O | 1,2-Ph | CH=CH | 4-isopropyl phenyl | 265 |
| 2-naphthyl | CH$_2$—O | 1,2-Ph | CH=CH | 2,3-dichloro phenyl | 266 |
| 2-naphthyl | CH$_2$—O | 1,2-Ph | CH=CH | 3,4-difluoro phenyl | 267 |
| 2-naphthyl | O—CH$_2$ | 1,2-Ph | CH=CH | 3,5-di-(CF$_3$) phenyl | 268 |
| 2-naphthyl | O—CH$_2$ | 1,2-Ph | CH=CH | 4-isopropyl phenyl | 269 |
| 2-naphthyl | O—CH$_2$ | 1,2-Ph | CH=CH | 2,3-dichloro phenyl | 270 |
| 2-naphthyl | O—CH$_2$ | 1,2-Ph | CH=CH | 3,4-difluoro phenyl | 271 |
| 2-naphthyl | S | 1,2-Ph | CH=CH | 3,5-di-(CF$_3$) phenyl | 272 |
| 2-naphthyl | S | 1,2-Ph | CH=CH | 4-isopropyl phenyl | 273 |
| 2-naphthyl | S | 1,2-Ph | CH=CH | 2,3-dichloro phenyl | 274 |
| 2-naphthyl | S | 1,2-Ph | CH=CH | 3,4-difluoro phenyl | 275 |
| 2-(6-benzyloxy) naphthyl | SO$_2$ | 1,2-Ph | CH=CH | 2-thienyl | 276 |
| 2-(6-benzyloxy) naphthyl | S | 1,2-Ph | CH=CH | 2-thienyl | 277 |
| 2-(6-benzyloxy) naphthyl | SO$_2$ | 1,2-Ph | 1,2-c-propyl | 2-thienyl | 278 |
| 2-(6-benzyloxy) naphthyl | S | 1,2-Ph | 1,2-c-propyl | 2-thienyl | 279 |
| 2-(5-benzyloxy) naphthyl | SO$_2$ | 1,2-Ph | CH=CH | 2-thienyl | 280 |
| 2-(5-benzyloxy) naphthyl | S | 1,2-Ph | CH=CH | 2-thienyl | 281 |
| 2-(5-benzyloxy) naphthyl | SO$_2$ | 1,2-Ph | 1,2-c-propyl | 2-thienyl | 282 |

TABLE I-continued $$R^1R^2R^3\text{—HET}\underset{X\text{—}B}{\overset{A}{\diagdown}}\underset{}{\overset{O}{\underset{}{\parallel}}}\text{NHSO}_2R^{19}$$

Ia (Compounds 1–323 and 347–454)

| $R^1R^2R^3$—Het | A | X | B | $R^{19}$ | Cpd |
|---|---|---|---|---|---|
| 2-(5-benzyloxy)naphthyl | S | 1,2-Ph | 1,2-c-propyl | 2-thienyl | 283 |
| 2-(6-(4-trifluoromethyl)benzyloxy))naphthyl | SO$_2$ | 1,2-Ph | CH=CH | 2-thienyl | 284 |
| 2-(6-(4-trifluoromethyl)benzyloxy))naphthyl | CH$_2$ | 1,2-Ph | CH=CH | 2-thienyl | 285 |
| 2-(6-(4-trifluoromethyl)benzyloxy))naphthyl | CH$_2$ | 1,2-Ph | 1,2-c-propyl | 2-thienyl | 286 |
| 2-(6-(4-trifluoromethyl)benzyloxy))naphthyl | CH$_2$ | 1,2-Ph | 1,2-c-propyl | 2-thienyl | 287 |
| 1-(6-benzyloxy)naphthyl | SO$_2$ | 1,2-Ph | CH=CH | 2-thienyl | 288 |
| 1-(6-benzyloxy)naphthyl | CH$_2$ | 1,2-Ph | CH=CH | 2-thienyl | 289 |
| 2-(6-(3,4-difluorobenzyloxy))naphthyl | SO$_2$ | 1,2-Ph | CH=CH | 2-thienyl | 290 |
| 2-(6-(3,4-difluorobenzyloxy))naphthyl | CH$_2$ | 1,2-Ph | CH=CH | 2-thienyl | 291 |
| 2-(6-(4-fluorobenzyloxy))naphthyl | CH$_2$ | 1,2-Ph | 1,2-c-propyl | 2-thienyl | 292 |
| 2-(7-benzyloxy)naphthyl | SO$_2$ | 1,2-Ph | CH=CH | 2-thienyl | 293 |
| 2-(6-(3,4-difluorobenzyloxy))naphthyl | SO$_2$ | 1,2-Ph | CH=CH | 3,4-difluorophenyl | 294 |
| 2-(6-(3,4-difluorobenzyloxy))naphthyl | CH$_2$ | 1,2-Ph | CH=CH | 3,4-difluorophenyl | 295 |
| 2-(6-(4-fluorobenzyloxy))naphthyl | CH$_2$ | 1,2-Ph | 1,2-c-propyl | 3,4-difluorophenyl | 296 |
| 2-(7-benzyloxy)naphthyl | SO$_2$ | 1,2-Ph | CH=CH | 3,5-di-(CF$_3$)phenyl | 297 |
| 2-(6-(3,4-difluorobenzyloxy))naphthyl | SO$_2$ | 1,2-Ph | CH=CH | 3,5-di-(CF$_3$)phenyl | 298 |
| 2-(6-(3,4-difluorobenzyloxy))naphthyl | CH$_2$ | 1,2-Ph | CH=CH | 3,5-di-(CF$_3$)phenyl | 299 |
| 2-(7-benzyloxy)naphthyl | SO$_2$ | 1,2-Ph | 1,2-c-propyl | 3,4-difluorophenyl | 300 |
| 2-naphthyl | CH$_2$ | 1,2-Ph | CH=CH | 2-methoxy-5-bromophenyl | 301 |
| 2-naphthyl | CH$_2$ | 4-Cl-1,2-Ph | CH=CH | 2-methoxy-5-bromophenyl | 302 |
| 2-naphthyl | CH$_2$ | 4-Cl-1,2-Ph | CH=CH | 2-thienyl | 303 |
| 2-naphthyl | SO | 1,2-Ph | CH=CH | 2-methoxy-5-bromophenyl | 304 |
| 2-naphthyl | SO$_2$ | 1,2-Ph | CH=CH | 2-methoxy-5-bromophenyl | 305 |
| 2-naphthyl | O | 1,2-Ph | CH=CH | 2-methoxy-5-bromophenyl | 306 |
| 2-(5-benzyloxy)naphthyl | CH$_2$ | 1,2-Ph | CH=CH | 2-methoxy-5-bromophenyl | 307 |
| 2-(5-benzyloxy)naphthyl | SO$_2$ | 1,2-Ph | CH=CH | 2-methoxy-5-bromophenyl | 308 |
| 2-(5-benzyloxy)naphthyl | S | 1,2-Ph | CH=CH | 2-methoxy-5-bromophenyl | 309 |
| 2-naphthyl | CH$_2$ | 1,2-Ph | 1,2-c-propyl | 2-methoxy-5-bromophenyl | 310 |
| 1,2-Ph | SO$_2$ | 1,2-Ph | 1,2-c-propyl | 2-methoxy-5- | 311 |

TABLE I-continued $$R^1R^2R^3-HET\underset{X-B}{\overset{A}{\diagdown}}\underset{NHSO_2R^{19}}{\overset{O}{\diagup}}$$ Ia (Compounds 1–323 and 347–454)

| R¹R²R³—Het | A | X | B | R¹⁹ | Cpd |
|---|---|---|---|---|---|
| 2-naphthyl | S | 1,2-Ph | 1,2-c-propyl | 2-methoxy-5-bromophenyl | 312 |
| 2-naphthyl | CH₂—O | 1,2-Ph | CH=CH | 2-methoxy-5-bromophenyl | 313 |
| 2-naphthyl | S | 1,2-Ph | CH=CH | 2-methoxy-5-bromophenyl | 314 |
| 3-methyl indol-1-yl | SO₂ | 1,2-Ph | 1,2-c-propyl | 2-methoxy-5-bromophenyl | 315 |
| 3-methyl indol-1-yl | S | 1,2-Ph | 1,2-c-propyl | 2-methoxy-5-bromophenyl | 316 |
| 3-methyl indol-1-yl | CH₂—O | 1,2-Ph | CH=CH | 2-methoxy-5-bromophenyl | 317 |
| 3-methyl indol-1-yl | S | 1,2-Ph | CH=CH | 2-methoxy-5-bromophenyl | 318 |
| 3-methyl indol-1-yl | O—CH₂ | 1,2-Ph | 1,2-c-propyl | 2-methoxy-5-bromophenyl | 319 |
| 3-methyl indol-1-yl | SO | 1,2-Ph | 1,2-c-propyl | 2-methoxy-5-bromophenyl | 320 |
| 3-methyl indol-1-yl | CH₂—O | 4-Cl-1,2-Ph | CH=CH | 2-methoxy-5-bromophenyl | 321 |
| 3-methyl indol-1-yl | S | 4-Cl-1,2-Ph | CH=CH | 2-methoxy-5-bromophenyl | 322 |
| 3-methyl indol-1-yl | SO₂ | 4-Cl-1,2-Ph | 1,2-c-propyl | 2-methoxy-5-bromophenyl | 323 |
| 2-(7-fluoro) naphthyl | SO₂ | 4-Cl-1,2-Ph | CH=CH | 2-thienyl | 347 |
| 2-(7-fluoro) naphthyl | O | 4-Cl-1,2-Ph | CH=CH | 2-thienyl | 348 |
| 2-(7-fluoro) naphthyl | S | 4-Cl-1,2-Ph | CH=CH | 2-thienyl | 349 |
| 2-(7-fluoro) naphthyl | CH₂ | 4-Cl-1,2-Ph | CH=CH | 2-thienyl | 350 |
| 2-(7-fluoro) naphthyl | CH₂ | 6-Cl-1,2-Ph | CH=CH | 2-thienyl | 351 |
| 2-(7-fluoro) naphthyl | CH₂ | 4-Cl-1,2-Ph | 1,2-c-Pr | 2-thienyl | 352 |
| 2-(7-fluoro) naphthyl | CH₂ | 3-Cl-1,2-Ph | CH=CH | 2-thienyl | 353 |
| 2-(7-fluoro) naphthyl | SO₂ | 4-Cl-1,2-Ph | CH=CH | 2-methoxy-5-bromophenyl | 354 |
| 2-(7-fluoro) naphthyl | O | 4-Cl-1,2-Ph | CH=CH | 2-methoxy-5-bromophenyl | 355 |
| 2-(7-fluoro) naphthyl | S | 4-Cl-1,2-Ph | CH=CH | 2-methoxy-5-bromophenyl | 356 |
| 2-naphthyl | CH₂ | 4,5-Cl₂-1,2-Ph | CH=CH | 2-methoxy-5-bromophenyl | 357 |
| 2-(7-fluoro) naphthyl | CH₂ | 6-Cl-1,2-Ph | CH=CH | 2-methoxy-5-bromophenyl | 358 |
| 2-(7-fluoro) naphthyl | CH₂ | 4-Cl-1,2-Ph | 1,2-c-Pr | 2-methoxy-5-bromophenyl | 359 |
| 2-(7-fluoro) naphthyl | CH₂ | 3-Cl-1,2-Ph | CH=CH | 2-methoxy-5-bromophenyl | 360 |
| 2-(7-fluoro) naphthyl | SO₂ | 4-Cl-1,2-Ph | CH=CH | 2-trifluoro methoxy-5-chlorophenyl | 361 |
| 2-(7-fluoro) naphthyl | O | 4-Cl-1,2-Ph | CH=CH | 2-trifluoro methoxy-5-chlorophenyl | 362 |
| 2-(7-fluoro) naphthyl | S | 4-Cl-1,2-Ph | CH=CH | 2-trifluoro methoxy-5-chlorophenyl | 363 |
| 2-(7-fluoro) naphthyl | CH₂ | 4-Cl-1,2-Ph | CH=CH | 2-trifluoro methoxy-5-chlorophenyl | 364 |
| 2-(7-fluoro) naphthyl | CH₂ | 6-Cl-1,2-Ph | CH=CH | 2-trifluoro methoxy-5-chlorophenyl | 365 |

TABLE I-continued $$R^1R^2R^3-HET-A-X-B-C(=O)-NHSO_2R^{19}$$ Ia (Compounds 1–323 and 347–454)

| R¹R²R³—Het | A | X | B | R¹⁹ | Cpd |
|---|---|---|---|---|---|
| 2-(7-fluoro)naphthyl | CH₂ | 4-Cl-1,2-Ph | 1,2-c-Pr | 2-trifluoromethoxy-5-chlorophenyl | 366 |
| 2-(7-fluoro)naphthyl | CH₂ | 3-Cl-1,2-Ph | CH=CH | 2-trifluoromethoxy-5-chlorophenyl | 367 |
| 2-(7-fluoro)naphthyl | SO₂ | 4-Cl-1,2-Ph | CH=CH | 2-thienyl | 368 |
| 2-(7-fluoro)naphthyl | O | 4-Cl-1,2-Ph | CH=CH | 2-thienyl | 369 |
| 2-(7-fluoro)naphthyl | S | 4-Cl-1,2-Ph | CH=CH | 2-thienyl | 370 |
| 2-(7-fluoro)naphthyl | CH₂ | 4-Cl-1,2-Ph | CH=CH | 2-thienyl | 371 |
| 2-(7-fluoro)naphthyl | CH₂ | 6-Cl-1,2-Ph | CH=CH | 2-thienyl | 372 |
| 2-(7-fluoro)naphthyl | CH₂ | 4-Cl-1,2-Ph | 1,2-c-Pr | 2-thienyl | 373 |
| 2-(7-fluoro)naphthyl | CH₂ | 3-Cl-1,2-Ph | CH=CH | 2-thienyl | 374 |
| 2-(7-fluoro)naphthyl | SO₂ | 4-Cl-1,2-Ph | CH=CH | 2-methoxy-5-bromophenyl | 375 |
| 2-(6-fluoro)naphthyl | O | 4-Cl-1,2-Ph | CH=CH | 2-methoxy-5-bromophenyl | 376 |
| 2-(6-fluoro)naphthyl | S | 4-Cl-1,2-Ph | CH=CH | 2-methoxy-5-bromophenyl | 377 |
| 2-(6-fluoro)naphthyl | CH₂ | 4-Cl-1,2-Ph | CH=CH | 2-methoxy-5-bromophenyl | 378 |
| 2-(6-fluoro)naphthyl | CH₂ | 6-Cl-1,2-Ph | CH=CH | 2-methoxy-5-bromophenyl | 379 |
| 2-(6-fluoro)naphthyl | CH₂ | 4-Cl-1,2-Ph | 1,2-c-Pr | 2-methoxy-5-bromophenyl | 380 |
| 2-(6-fluoro)naphthyl | CH₂ | 3-Cl-1,2-Ph | CH=CH | 2-methoxy-5-bromophenyl | 381 |
| 2-(7-chloro)naphthyl | SO₂ | 4-Cl-1,2-Ph | CH=CH | 2-thienyl | 382 |
| 2-(7-chloro)naphthyl | O | 4-Cl-1,2-Ph | CH=CH | 2-thienyl | 383 |
| 2-(7-chloro)naphthyl | S | 4-Cl-1,2-Ph | CH=CH | 2-thienyl | 384 |
| 2-(7-chloro)naphthyl | CH₂ | 4-Cl-1,2-Ph | CH=CH | 2-thienyl | 385 |
| 2-(7-chloro)naphthyl | CH₂ | 6-Cl-1,2-Ph | CH=CH | 2-thienyl | 386 |
| 2-(7-chloro)naphthyl | CH₂ | 4-Cl-1,2-Ph | 1,2-c-Pr | 2-thienyl | 387 |
| 2-(7-chloro)naphthyl | CH₂ | 3-Cl-1,2-Ph | CH=CH | 2-thienyl | 388 |
| 2-(6,7-difluoro)naphthyl | SO₂ | 4-Cl-1,2-Ph | CH=CH | 2-thienyl | 389 |
| 2-(6,7-difluoro)naphthyl | O | 4-Cl-1,2-Ph | CH=CH | 2-thienyl | 390 |
| 2-(6,7-difluoro)naphthyl | S | 4-Cl-1,2-Ph | CH=CH | 2-thienyl | 391 |
| 2-(6,7-difluoro)naphthyl | CH₂ | 4-Cl-1,2-Ph | CH=CH | 2-thienyl | 392 |
| 2-(6,7-difluoro)naphthyl | CH₂ | 6-Cl-1,2-Ph | CH=CH | 2-thienyl | 393 |
| 2-(6,7-difluoro)naphthyl | CH₂ | 4-Cl-1,2-Ph | 1,2-c-Pr | 2-thienyl | 394 |
| 2-(6,7-difluoro)naphthyl | CH₂ | 3-Cl-1,2-Ph | CH=CH | 2-thienyl | 395 |
| 2-(6,7-difluoro)naphthyl | SO₂ | 4-Cl-1,2-Ph | CH=CH | 2-methoxy-5-bromophenyl | 396 |
| 2-(6,7-difluoro)naphthyl | O | 4-Cl-1,2-Ph | CH=CH | 2-methoxy-5-bromophenyl | 397 |
| 2-(6,7-difluoro)naphthyl | S | 4-Cl-1,2-Ph | CH=CH | 2-methoxy-5-bromophenyl | 398 |

TABLE I-continued $$R^1R^2R^3-HET-\underset{X-B}{\overset{A}{\underset{|}{C}}}-\underset{NHSO_2R^{19}}{\overset{O}{\parallel}}$$ Ia (Compounds 1–323 and 347–454)

| R¹R²R³—Het | A | X | B | R¹⁹ | Cpd |
|---|---|---|---|---|---|
| 2-(6,7-difluoro)naphthyl | CH₂ | 4-Cl-1,2-Ph | CH=CH | 2-methoxy-5-bromophenyl | 399 |
| 2-(6,7-difluoro)naphthyl | CH₂ | 6-Cl-1,2-Ph | CH=CH | 2-methoxy-5-bromophenyl | 400 |
| 2-(6,7-difluoro)naphthyl | CH₂ | 4-Cl-1,2-Ph | 1,2-c-Pr | 2-methoxy-5-bromophenyl | 401 |
| 2-(6,7-difluoro)naphthyl | CH₂ | 3-Cl-1,2-Ph | CH=CH | 2-methoxy-5-bromophenyl | 402 |
| 2-(5,7-difluoro)naphthyl | CH₂ | 4-Cl-1,2-Ph | CH=CH | 2-methoxy-5-bromophenyl | 403 |
| 2-(5,7-difluoro)naphthyl | S | 4-Cl-1,2-Ph | CH=CH | 2-methoxy-5-bromophenyl | 404 |
| 2-(5,7-difluoro)naphthyl | O | 4-Cl-1,2-Ph | CH=CH | 2-methoxy-5-bromophenyl | 405 |
| 2-(5,7-difluoro)naphthyl | SO₂ | 4-Cl-1,2-Ph | CH=CH | 2-methoxy-5-bromophenyl | 406 |
| 2-(6-fluoro)quinolinyl | SO₂ | 4-Cl-1,2-Ph | CH=CH | 2-methoxy-5-bromophenyl | 407 |
| 2-(6-fluoro)quinolinyl | S | 4-Cl-1,2-Ph | CH=CH | 2-methoxy-5-bromophenyl | 408 |
| 2-(6-fluoro)quinolinyl | CH₂ | 4-Cl-1,2-Ph | CH=CH | 2-methoxy-5-bromophenyl | 409 |
| 2-(6-fluoro)quinolinyl | CH₂ | 1,2-Ph | CH=CH | 2-methoxy-5-bromophenyl | 410 |
| 2-(6-fluoro)quinolinyl | O | 4-Cl-1,2-Ph | CH=CH | 2-methoxy-5-bromophenyl | 411 |
| 2-(6-fluoro)quinolinyl | CH₂ | 4-Cl-1,2-Ph | 1,2-c-Pr | 2-methoxy-5-bromophenyl | 412 |
| 2-(5,7-difluoro)-quinolinyl | SO₂ | 4-Cl-1,2-Ph | CH=CH | 2-methoxy-5-bromophenyl | 413 |
| 2-(5,7-difluoro)-quinolinyl | S | 4-Cl-1,2-Ph | CH=CH | 2-methoxy-5-bromophenyl | 414 |
| 2-(5,7-difluoro)-quinolinyl | CH₂ | 4-Cl-1,2-Ph | CH=CH | 2-methoxy-5-bromophenyl | 415 |
| 2-(5,7-difluoro)-quinolinyl | CH₂ | 1,2-Ph | CH=CH | 2-methoxy-5-bromophenyl | 416 |
| 2-(5,7-difluoro)-quinolinyl | O | 4-Cl-1,2-Ph | CH=CH | 2-methoxy-5-bromophenyl | 417 |
| 2-(5,7-difluoro)-quinolinyl | CH₂ | 4-Cl-1,2-Ph | 1,2-c-Pr | 2-methoxy-5-bromophenyl | 418 |
| 3,4-dichlorophenyl | SO₂ | 4-Cl-1,2-Ph | CH=CH | 2-methoxy-5-bromophenyl | 419 |
| 3,4-dichlorophenyl | S | 4-Cl-1,2-Ph | CH=CH | 2-methoxy-5-bromophenyl | 420 |
| 3,4-dichlorophenyl | CH₂ | 4-Cl-1,2-Ph | CH=CH | 2-methoxy-5-bromophenyl | 421 |
| 3,4-dichlorophenyl | CH₂ | 1,2-Ph | CH=CH | 2-methoxy-5-bromophenyl | 422 |
| 3,4-dichlorophenyl | O | 4-Cl-1,2-Ph | CH=CH | 2-methoxy-5-bromophenyl | 423 |
| 3,4-dichlorophenyl | CH₂ | 4-Cl-1,2-Ph | 1,2-c-Pr | 2-methoxy-5-bromophenyl | 424 |
| 3,4-dichlorophenyl | CH₂ | 5-Cl-1,2-Ph | CH=CH | 2-methoxy-5-bromophenyl | 425 |
| 4-chlorophenyl | SO₂ | 4-Cl-1,2-Ph | CH=CH | 2-methoxy-5-bromophenyl | 426 |
| 4-chlorophenyl | S | 4-Cl-1,2-Ph | CH=CH | 2-methoxy-5-bromophenyl | 427 |
| 4-chlorophenyl | CH₂ | 4-Cl-1,2-Ph | CH=CH | 2-methoxy-5-bromophenyl | 428 |
| 4-chlorophenyl | CH₂ | 1,2-Ph | CH=CH | 2-methoxy-5-bromophenyl | 429 |
| 4-chlorophenyl | O | 4-Cl-1,2-Ph | CH=CH | 2-methoxy-5-bromophenyl | 430 |
| 4-chlorophenyl | CH₂ | 4-Cl-1,2-Ph | 1,2-c-Pr | 2-methoxy-5-bromophenyl | 431 |
| 4-chlorophenyl | CH₂ | 4-Cl-1,2-Ph | CH=CH | 2-methoxy-5-bromophenyl | 432 |

TABLE I-continued $$R^1R^2R^3-HET\overset{A}{\underset{X-B}{|}}\overset{O}{\underset{NHSO_2R^{19}}{||}}$$ Ia (Compounds 1–323 and 347–454)

| R¹R²R³—Het | A | X | B | R¹⁹ | Cpd |
|---|---|---|---|---|---|
| 3,4-dichloro phenyl | SO₂ | 4-Cl-1,2-Ph | CH=CH | 2-thienyl | 433 |
| 3,4-dichloro phenyl | S | 4-Cl-1,2-Ph | CH=CH | 2-thienyl | 434 |
| 3,4-dichloro phenyl | CH₂ | 4-Cl-1,2-Ph | CH=CH | 2-thienyl | 435 |
| 3,4-dichloro phenyl | CH₂ | 1,2-Ph | CH=CH | 2-thienyl | 436 |
| 3,4-dichloro phenyl | O | 4-Cl-1,2-Ph | CH=CH | 2-thienyl | 437 |
| 3,4-dichloro phenyl | CH₂ | 4-Cl-1,2-Ph | CH=CH | 2-thienyl | 438 |
| 3,4-dichloro phenyl | CH₂ | 5-Cl-1,2-Ph | CH=CH | 2-thienyl | 439 |
| 4-chloro phenyl | SO₂ | 4-Cl-1,2-Ph | CH=CH | 2-thienyl | 440 |
| 4-chloro phenyl | S | 4-Cl-1,2-Ph | CH=CH | 2-thienyl | 441 |
| 4-chloro phenyl | CH₂ | 4-Cl-1,2-Ph | CH=CH | 2-thienyl | 442 |
| 4-chloro phenyl | CH₂ | 1,2-Ph | CH=CH | 2-thienyl | 443 |
| 1-(5-chloro) indolyl | CH₂ | 3,2-Pyr | CH=CH | 2,4-(Me)₂-thiazol-5-yl | 444 |
| 1-(5-chloro) indolyl | CH₂ | 3,2-Pyr | CH=CH | 2-thienyl | 445 |
| 1-(6-(4-chloro) phenyl)indolyl | CH₂ | 4-F-1,2-Ph | CH=CH | 3-chloro-4-fluorophenyl | 446 |
| 2-(6-difluoro methoxy) naphthyl | CH₂ | 4-Cl-1,2-Ph | CH=CH | 2-methoxy-5-bromophenyl | 447 |
| 2-naphthyl | CH₂ | 4-MeO-1,2-Ph | CH=CH | 2-methoxy-5-bromophenyl | 448 |
| 2-naphthyl | CH₂ | 5-Cl-1,2-Ph | CH=CH | 2-methoxy-5-bromophenyl | 449 |
| 2-(6-chloro naphthyl) | CH₂ | 4-Cl-1,2-Ph | CH=CH | 2-methoxy-5-bromophenyl | 450 |
| 1-(5-phenyl methoxy) indolyl | CH₂ | 4-F-1,2-Ph | CH=CH | 2-methoxy-5-bromophenyl | 451 |
| 2-(benzo[b] thiophenyl | CH₂ | 4-F-1,2-Ph | CH=CH | 2-methoxy-5-bromophenyl | 452 |
| 5-(1-benzyl) indolyl | CH₂ | 4-F-1,2-Ph | CH=CH | 2-methoxy-5-bromophenyl | 453 |
| 1-(6-(4-chloro) phenyl)indolyl | CH₂ | 4-F-1,2-Ph | CH=CH | 2-methoxy-5-bromophenyl | 454 |

TABLE II $$R^1R^2R^3-HET\overset{A}{\underset{X-B}{|}}\overset{O}{\underset{OH}{||}}$$ I-b (Compounds 324–346 and 455–542)

| R¹R²R³—Het | A | X | B | Cpd |
|---|---|---|---|---|
| 2-naphthyl | S(O)₂ | 1,2-phenyl | CH=CH | 324 |
| 2-naphthyl | S | 1,2-phenyl | CH=CH | 325 |
| 4-methylthiophenyl | CH₂ | 1,2-phenyl | CH=CH | 326 |
| 3-methylindol-1-yl | CH₂ | 1,2-phenyl | CH=CH | 327 |
| 3-chloro-4-fluorophenyl | CH₂ | 1,2-phenyl | CH=CH | 328 |
| 4-chlorophenyl | CH₂ | 1,2-phenyl | CH=CH | 329 |
| 2-naphthyl | CH₂ | 1,2-phenyl | CH=CH | 330 |

TABLE II-continued

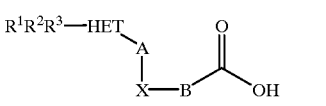

(Compounds 324–346 and 455–542)

| $R^1R^2R^3$—Het | A | X | B | Cpd |
|---|---|---|---|---|
| 2-naphthyl | $S(O)_2$ | 1,2-phenyl | 1,2-c-propyl | 331 |
| 2-naphthyl | $S(O)_2$ | 1,2-phenyl | $CH_2$—$CH_2$ | 332 |
| 2-naphthyl | S | 1,2-phenyl | CH=CH | 333 |
| 3,4-dichlorophenyl | $S(O)_2$ | 1,2-phenyl | $CH_2$—$CH_2$ | 334 |
| 3,4-dichlorophenyl | $CH_2$ | 1,2-phenyl | CH=CH | 335 |
| 2-(6-benzyloxy)naphthyl | $CH_2$ | 1,2-phenyl | CH=CH | 336 |
| 2-(6-benzyloxy)naphthyl | $CH_2$ | 1,2-phenyl | 1,2-c-propyl | 337 |
| 2-(6-benzyloxy)naphthyl | $SO_2$ | 1,2-phenyl | 1,2-c-propyl | 338 |
| 2-(6-benzyloxy)naphthyl | $CH_2$—O | 1,2-phenyl | 1,2-c-propyl | 339 |
| 2-(6-benzyloxy)naphthyl | O—$CH_2$ | 1,2-phenyl | 1,2-c-propyl | 340 |
| 2-(6-benzyloxy)naphthyl | $SO_2$ | 1,2-phenyl | CH=CH | 341 |
| 2-(6-benzyloxy)naphthyl | $CH_2$—O | 1,2-phenyl | CH=CH | 342 |
| 2-(6-benzyloxy)naphthyl | O—$CH_2$ | 1,2-phenyl | CH=CH | 343 |
| 2-(6-benzyloxy)naphthyl | S | 1,2-phenyl | CH=CH | 344 |
| 2-(7-benzyloxy)naphthyl | $SO_2$ | 1,2-phenyl | CH=CH | 345 |
| 2-(6-(4-trifluoromethyl) benzyloxy))naphthyl | $CH_2$ | 1,2-phenyl | CH=CH | 346 |
| 2-(6-fluoro)naphthyl | $SO_2$ | 4-Cl-1,2-Ph | CH=CH | 455 |
| 2-(6-fluoro)naphthyl | S | 4-Cl-1,2-Ph | CH=CH | 456 |
| 2-(6-fluoro)naphthyl | $CH_2$ | 4-Cl-1,2-Ph | CH=CH | 457 |
| 2-(6-fluoro)naphthyl | $CH_2$ | 1,2-Ph | CH=CH | 458 |
| 2-(6-fluoro)naphthyl | O | 4-Cl-1,2-Ph | CH=CH | 459 |
| 2-(6-fluoro)naphthyl | $CH_2$ | 4-Cl-1,2-Ph | 1,2-c-Pr | 460 |
| 2-(7-fluoro)naphthyl | $SO_2$ | 4-Cl-1,2-Ph | CH=CH | 461 |
| 2-(7-fluoro)naphthyl | S | 4-Cl-1,2-Ph | CH=CH | 462 |
| 2-(7-fluoro)naphthyl | $CH_2$ | 4-Cl-1,2-Ph | CH=CH | 463 |
| 2-(7-fluoro)naphthyl | $CH_2$ | 1,2--Ph | CH=CH | 464 |
| 2-(7-fluoro)naphthyl | O | 4-Cl-1,2-Ph | CH=CH | 465 |
| 2-(7-fluoro)naphthyl | $CH_2$ | 4-Cl-1,2-Ph | 1,2-c-Pr | 466 |
| 2-(6-chloro)naphthyl | $SO_2$ | 4-Cl-1,2-Ph | CH=CH | 467 |
| 2-(6-chloro)naphthyl | S | 4-Cl-1,2-Ph | CH=CH | 468 |
| 2-(6-chloro)naphthyl | $CH_2$ | 4-Cl-1,2-Ph | CH=CH | 469 |
| 2-(6-chloro)naphthyl | $CH_2$ | 1,2-Ph | CH=CH | 470 |
| 2-(6-chloro)naphthyl | O | 4-Cl-1,2-Ph | CH=CH | 471 |
| 2-(6-chloro)naphthyl | $CH_2$ | 4-Cl-1,2-Ph | 1,2-c-Pr | 472 |
| 2-(7-chloro)naphthyl | $SO_2$ | 4-Cl-1,2-Ph | CH=CH | 473 |
| 2-(7-chloro)naphthyl | S | 4-Cl-1,2-Ph | CH=CH | 474 |
| 2-(7-chloro)naphthyl | $CH_2$ | 4-Cl-1,2-Ph | CH=CH | 475 |
| 2-(7-chloro)naphthyl | $CH_2$ | 4-Cl-1,2-Ph | CH=CH | 476 |
| 2-(7-chloro)naphthyl | $CH_2$ | 4-Cl-1,2-Ph | CH=CH | 477 |
| 2-(7-chloro)naphthyl | $CH_2$ | 4-Cl-1,2-Ph | CH=CH | 478 |
| 2-(6,7-difluoro)naphthyl | $SO_2$ | 4-Cl-1,2-Ph | CH=CH | 479 |
| 2-(6,7-difluoro)naphthyl | S | 4-Cl-1,2-Ph | CH=CH | 480 |
| 2-(6,7-difluoro)naphthyl | $CH_2$ | 4-Cl-1,2-Ph | CH=CH | 481 |
| 2-(6,7-difluoro)naphthyl | $CH_2$ | 4-Cl-1,2-Ph | CH=CH | 482 |
| 2-(6,7-difluoro)naphthyl | $CH_2$ | 4-Cl-1,2-Ph | CH=CH | 483 |
| 2-(6,7-difluoro)naphthyl | $CH_2$ | 4-Cl-1,2-Ph | 1,2-c-Pr | 484 |
| 2-(6,7-difluoro)naphthyl | $CH_2$ | 4-Cl-1,2-Ph | CH=CH | 485 |
| 2-(6,7-difluoro)naphthyl | $CH_2$ | 4-Cl-1,2-Ph | CH=CH | 486 |
| 2-(6,7-difluoro)naphthyl | $CH_2$ | 4-Cl-1,2-Ph | CH=CH | 487 |
| 2-(6,7-difluoro)naphthyl | $CH_2$ | 1,2-Ph | CH=CH | 488 |
| 2-(6,7-difluoro)naphthyl | $CH_2$ | 4-Cl-1,2-Ph | CH=CH | 489 |
| 2-(6,7-difluoro)naphthyl | $CH_2$ | 4-Cl-1,2-Ph | 1,2-c-Pr | 490 |
| 3-methyl-5-fluoro indol-1-yl | $SO_2$ | 4-Cl-1,2-Ph | CH=CH | 491 |
| 3-methyl-5-fluoro indol-1-yl | S | 4-Cl-1,2-Ph | CH=CH | 492 |
| 3-methyl-5-fluoro indol-1-yl | $CH_2$ | 4-Cl-1,2-Ph | CH=CH | 493 |
| 3-methyl-5-fluoro indol-1-yl | $CH_2$ | 1,2-Ph | CH=CH | 494 |
| 3-methyl-5-fluoro indol-1-yl | $CH_2$ | 4-Cl-1,2-Ph | CH=CH | 495 |
| 3-methyl-5-fluoro indol-1-yl | $CH_2$ | 4-Cl-1,2-Ph | CH=CH | 496 |
| 2-(6-fluoro)quinolinyl | $SO_2$ | 4-Cl-1,2-Ph | CH=CH | 497 |
| 2-(6-fluoro)quinolinyl | S | 4-Cl-1,2-Ph | CH=CH | 498 |
| 2-(6-fluoro)quinolinyl | $CH_2$ | 4-Cl-1,2-Ph | CH=CH | 499 |
| 2-(6-fluoro)quinolinyl | $CH_2$ | 4-Cl-1,2-Ph | CH=CH | 500 |

TABLE II-continued

I-b $R^1R^2R^3$—HET—A—X—B—C(=O)OH (Compounds 324–346 and 455–542)

| $R^1R^2R^3$—Het | A | X | B | Cpd |
|---|---|---|---|---|
| 2-(6-fluoro)quinolinyl | O | 4-Cl-1,2-Ph | CH=CH | 501 |
| 2-(6-fluoro)quinolinyl | $CH_2$ | 4-Cl-1,2-Ph | CH=CH | 502 |
| 2-(6-difluoromethoxy)-naphthyl | $SO_2$ | 4-Cl-1,2-Ph | CH=CH | 503 |
| 2-(6-difluoromethoxy)-naphthyl | $SO_2$ | 4-Cl-1,2-Ph | CH=CH | 504 |
| 2-(6-difluoromethoxy)-naphthyl | $SO_2$ | 4-Cl-1,2-Ph | CH=CH | 505 |
| 2-(6-difluoromethoxy)-naphthyl | $SO_2$ | 4-Cl-1,2-Ph | CH=CH | 506 |
| 2-(6-difluoromethoxy)-naphthyl | $SO_2$ | 4-Cl-1,2-Ph | CH=CH | 507 |
| 2-(6-difluoromethoxy)-naphthyl | $SO_2$ | 4-Cl-1,2-Ph | CH=CH | 508 |
| 2-(7-difluoromethoxy)-naphthyl | $SO_2$ | 4-Cl-1,2-Ph | CH=CH | 509 |
| 2-(7-difluoromethoxy)-naphthyl | S | 4-Cl-1,2-Ph | CH=CH | 510 |
| 2-(7-difluoromethoxy)-naphthyl | $CH_2$ | 4-Cl-1,2-Ph | CH=CH | 511 |
| 2-(7-difluoromethoxy)-naphthyl | $CH_2$ | 4-Cl-1,2-Ph | CH=CH | 512 |
| 2-(7-difluoromethoxy)-aphthyl | O | 4-Cl-1,2-Ph | CH=CH | 513 |
| 2-(7-difluoromethoxy)-naphthyl | $CH_2$ | 4-Cl-1,2-Ph | CH=CH | 514 |
| 2-(6-methoxy)naphthyl | $SO_2$ | 4-Cl-1,2-Ph | CH=CH | 515 |
| 2-(6-methoxy)naphthyl | S | 4-Cl-1,2-Ph | CH=CH | 516 |
| 2-(6-methoxy)naphthyl | $CH_2$ | 4-Cl-1,2-Ph | CH=CH | 517 |
| 2-(6-methoxy)naphthyl | $CH_2$ | 4-Cl-1,2-Ph | CH=CH | 518 |
| 2-(6-methoxy)naphthyl | O | 4-Cl-1,2-Ph | CH=CH | 519 |
| 2-(6-methoxy)naphthyl | $CH_2$ | 4-Cl-1,2-Ph | CH=CH | 520 |
| 2-(6-fluoro)naphthyl | $CH_2$ | 4-Cl-1,2-Ph | CH=CH | 521 |
| 2-(6-fluoro)naphthyl | $CH_2$ | 4-Cl-1,2-Ph | CH=CH | 522 |
| 2-(6-fluoro)naphthyl | $CH_2$ | 4-Cl-1,2-Ph | CH=CH | 523 |
| 2-(6-fluoro)naphthyl | $CH_2$ | 4-Cl-1,2-Ph | CH=CH | 524 |
| 2-(6-fluoro)naphthyl | $CH_2$ | 4-Cl-1,2-Ph | CH=CH | 525 |
| 2-(6-fluoro)naphthyl | $CH_2$ | 4-Cl-1,2-Ph | CH=CH | 526 |
| 2-(7-fluoro)naphthyl | $CH_2$ | 4-Cl-1,2-Ph | CH=CH | 527 |
| 2-(7-fluoro)naphthyl | $CH_2$ | 4-Cl-1,2-Ph | CH=CH | 528 |
| 2-(7-fluoro)naphthyl | $CH_2$ | 4-Cl-1,2-Ph | CH=CH | 529 |
| 2-(7-fluoro)naphthyl | $CH_2$ | 4-Cl-1,2-Ph | CH=CH | 530 |
| 2-(7-fluoro)naphthyl | $CH_2$ | 4-Cl-1,2-Ph | CH=CH | 531 |
| 2-(7-fluoro)naphthyl | $CH_2$ | 4-Cl-1,2-Ph | CH=CH | 532 |
| 2-naphthyl | $CH_2$ | 4,5-$Cl_2$-1,2-Ph | CH=CH | 533 |
| 2-naphthyl | $CH_2$ | 4-Cl-1,2-Ph | CH=CH | 534 |
| 3,4-dichlorophenyl | $CH_2$ | 4-Cl-1,2-Ph | CH=CH | 535 |
| 2-naphthyl | $CH_2$ | 4-Cl-1,2-Ph | CH=CH | 536 |
| 4-chlorophenyl | $CH_2$ | 4-Cl-1,2-Ph | CH=CH | 537 |
| 1-(5-phenylmethoxy)indolyl | $CH_2$ | 4-F-1,2-Ph | CH=CH | 538 |

| $R^1R^2R^3$-Het | A | X | B | Cpd |
|---|---|---|---|---|
| 2-(benzo[b]thiophenyl) | $CH_2$ | 4-F-1,2-Ph | CH = CH | 539 |
| 5-(1-benzyl)indolyl | $CH_2$ | 4-F-1,2-Ph | CH = CH | 540 |
| 1-(6-(4-chloro)phenyl)indolyl | $CH_2$ | 4-F-1,2-Ph | CH = CH | 541 |
| 1-(5-chloro)indolyl | $CH_2$ | 3,2-Pyr | CH = CH | 542 | wherein D=—O($CH_2$)$_3$—O, Qn=7-chloroquinolin-2-yl, 1,2-Ph=1,2-benzenediyl, $R^s$=—$CH_2SCH_2CH_2$Ph, Pyr=pyridinediyl, c-pr=cyclopropyl and Bn=benzyl.

8. A method of treating or preventing a prostaglandin mediated disease which is comprised of administering to a mammalian patient in need of such treatment a compound in accordance with claim 1 in an amount which is effective for treating or preventing a prostaglandin mediated disease.

9. A method in accordance with claim 8 wherein the prostaglandin mediated disease is selected from the group consisting of:
pain, fever or inflammation associated with rheumatic fever, influenza or other viral infections, common cold, low back and neck pain, skeletal pain, post-partum pain, dysmenorrhea, headache, migraine, toothache, sprains and strains, myositis, neuralgia, synovitis, arthritis, including rheumatoid arthritis, degenerative joint diseases (osteoarthritis), gout and ankylosing spondylitis, bursitis, burns including radiation and corrosive chemical injuries, sunburns, pain following surgical and dental procedures, immune and autoimmune diseases;

cellular neoplastic transformations or metastic tumor growth;

diabetic retinopathy, tumor angiogenesis;

prostanoid-induced smooth muscle contraction associated with dysmenorrhea, premature labor, asthma or eosinophil related disorders;

Alzheimer's disease;

glaucoma;

bone loss;

osteoporosis;

promotion of bone formation;

Paget's disease;

cytoprotection in peptic ulcers, gastritis, regional enteritis, ulcerative colitis, diverticulitis or other gastrointestinal lesions; GI bleeding and patients undergoing chemotherapy;

coagulation disorders selected from hypoprothrombinemia, hemophilia and other bleeding problems;

kidney disease;

thrombosis;

occlusive vascular disease;

presurgery;

and anti-coagulation.

10. A method in accordance with claim 8 wherein the prostaglandin mediated disease is selected from the group consisting of: pain, fever or inflammation.

11. A method in accordance with claim 8 wherein the prostaglandin mediated disease is dysmenorrhea.

12. A method in accordance with claim 8, wherein the compound is co-administered with other agents or ingredients.

13. A method in accordance with claim 12 wherein the compound I is co-administered with another agent or ingredient selected from the group consisting of: an analgesic selected from acetaminophen, phenacetin, aspirin, a narcotic;

a COX-2 selective NSAID and a conventional NSAID;

caffeine;

an $H_2$-antagonist;

aluminum or magnesium hydroxide;

simethicone;

a decongestant selected from phenylephrine, phenylpropanolamine, pseudophedrine, oxymetazoline, ephinephrine, naphazoline, xylometazoline, propylhexedrine, or levo-desoxyephedrine;

an antiitussive selected from codeine, hydrocodone, caramiphen, carbetapentane and dextramethorphan;

another prostaglandin ligand selected from misoprostol, enprostil, rioprostil, ornoprostol and rosaprostol; a diuretic; and a sedating or non-sedating antihistamine.

14. A pharmaceutical composition which is comprised of a compound in accordance with claim 1 in combination with a pharmaceutically acceptable carrier.

15. A pharmaceutical composition which is comprised of a compound in accordance with claim 2 in combination with a pharmaceutically acceptable carrier.

16. A method of treating or preventing a prostaglandin mediated disease which is comprised of administering to a mammalian patient in need of such treatment a compound in accordance with claim 2 in an amount which is effective for treating or preventing a prostaglandin mediated disease.

* * * * *